United States Patent
Singh et al.

(10) Patent No.: US 9,845,330 B2
(45) Date of Patent: Dec. 19, 2017

(54) 6-NITRO-2,3-DIHYDROIMIDAZO[2,1-B] OXAZOLES AND A PROCESS FOR THE PREPARATION THEREOF

(71) Applicant: COUNCIL OF SCIENTIFIC & INDUSTRIAL RESEARCH, New Delhi (IN)

(72) Inventors: Parvinder Pal Singh, Jammu (IN); Gurunadham Munagala, Jammu (IN); Reddy Yempalla Kushalava, Jammu (IN); Inshad Ali Khan, Jammu (IN); Nitin Pal Kalia, Jammu (IN); Vikrant Singh Rajput, Jammu (IN); Amit Nargotra, Jammu (IN); Sanghapal Damodhar Sawant, Jammu (IN); Ram Asray Vishwakarma, Jammu (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 0 days.

(21) Appl. No.: 15/027,137

(22) PCT Filed: Mar. 31, 2014

(86) PCT No.: PCT/IN2014/000202
§ 371 (c)(1),
(2) Date: Apr. 4, 2016

(87) PCT Pub. No.: WO2015/049693
PCT Pub. Date: Apr. 9, 2015

(65) Prior Publication Data
US 2016/0244462 A1    Aug. 25, 2016

(30) Foreign Application Priority Data
Oct. 4, 2013    (IN) .......................... 2954/DEL/2013

(51) Int. Cl.
| | |
|---|---|
| *C07D 498/04* | (2006.01) |
| *A61K 31/424* | (2006.01) |
| *A61K 31/4439* | (2006.01) |
| *A61K 31/454* | (2006.01) |
| *A61K 31/496* | (2006.01) |
| *A61K 31/5377* | (2006.01) |
| *A61K 45/06* | (2006.01) |

(52) U.S. Cl.
CPC .......... *C07D 498/04* (2013.01); *A61K 31/424* (2013.01); *A61K 31/4439* (2013.01); *A61K 31/454* (2013.01); *A61K 31/496* (2013.01); *A61K 31/5377* (2013.01); *A61K 45/06* (2013.01)

(58) Field of Classification Search
CPC ......................... C07D 498/04; A61K 31/424
See application file for complete search history.

(56) References Cited

U.S. PATENT DOCUMENTS

| 7,262,212 B2 * | 8/2007 | Tsubouchi | ........... C07D 498/04 514/278 |
| 7,666,864 B2 * | 2/2010 | Ding | .................... C07D 498/04 514/211.1 |
| 8,163,753 B2 * | 4/2012 | Tsubouchi | ........... C07D 498/04 514/252.16 |

FOREIGN PATENT DOCUMENTS

WO    2007/013477 A1    2/2007

OTHER PUBLICATIONS

Nagarajan, Kuppuswamy et al., "Nitroimidazoles XXI** 2,3-dihydro-6-nitroimidazo [2,1-b] oxaoles with antitubercular activity", Eur. J. Med. Chem. 1989, 24, 63.
Ashtekar, D. R. et al., "In Vitro and In Vivo Activities of the Nitroimidazole CGI 17341 against *Mycobacterium tuberculosis*," Antimicrobial Agents and Chemotherapy,1993, 37, 183.
Dye, Christopher et al., "Global Burden of Tuberculosis Estimated Incidence, Prevalence, and Mortality by Country," American Medical Association, 1999, 282, 677.
Stover, Kendall et al., "A Small-molecule nitroimidazopyran drug candidate for the treatment of tuberculosis," Nature, 2000,405, 962.
Bemer-Melchior, Pascale et al., "Comparison of the in vitro activites of rifapentine and rifampicin against *Mycobacterium tuberculosis* complex," Journal of Antimicrobial Chemotherapy, 2000, 46, 571.
Sasaki, Hirofumi et al., "Synthesis and Antituberculosis Activity of a Novel Series of Optically Active 6-Nitro-2,3-dihydroimidazo [2,1-b] oxazoles," J. Med. Chem. 2006, 49, 7854.
Edney, Anna, "J&J Sirturo Winds FDA Approval to Treat Drug-Resistatn TB," Bloomberg, 2013.

* cited by examiner

*Primary Examiner* — Golam M M Shameem
(74) *Attorney, Agent, or Firm* — McDonald Hopkins LLC

(57) ABSTRACT

The present invention relates to newer generation of triazoles, tetrazoles, isoxazoles, urea and sulphonamide functionalities containing 6-nitro-2,3-dihydronitroimidazooxazoles agents of formula 1, their method of preparation, and their use as drugs for treating *Mycobacterium tuberculosis*, MDR-TB and XDR-TB either alone or in combination with other anti-tubercular agents. In the present invention, new generation 6-nitro-2,3-dihydronitroimidazooxazoles agents also show acceptable pharmacokinetic properties and synergistic or additive effects with known anti-tubercular drugs.

General formula 1

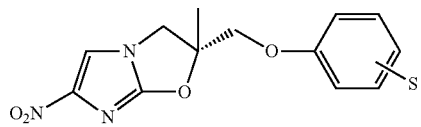

6 Claims, 14 Drawing Sheets

General formula 1

IA

IIA

IB

IIB

IC

IIC

Scheme1:Reagents and conditions: a) HNO₃, ACOH, AC₂O, 5 °C, 2 h, and then at rt, 12 h; b) chloro benzene, 120-125 °C, 50 h; c) con HCl, 90-95 °C, 12 h; d) Et₃N, AcOEt, 60-65 °C, 6 h; e) K₂CO₃, MeOH, rt, 2 h; f) MsCl, pyridine, <15 °C, 2 h; g) DBU, AcOEt, rt, 2 h.

Scheme 2: Reagents and Conditions: a) NaNO$_2$, HCl, 0 °C, 2 h, NaN$_3$, H$_2$O, 2 h; b) CuSO$_4$, $^t$BuOH, H$_2$O, Sodium Ascorbate, rt, 12 h.

Scheme 3: Reagents and Conditions: a) NaNO$_2$, HCl, 0 °C, 2 h, NaN$_3$, H$_2$O, 2 h; b) CuSO$_4$, $^t$BuOH, H$_2$O, Sodium Ascorbate, rt, 12 h.

Scheme 4: Reagents and Conditions: a) NaNO$_2$, HCl, 0 °C, 2 h, NaN$_3$, H$_2$O, 2 h; b) CuSO$_4$, $^t$BuOH, H$_2$O, Sodium Ascorbate, rt, 12 h.

Scheme 5: Reagents and Conditions: a) NaH, DMF, 0 °C to 50 °C, 12 h.

Scheme 6: Reagents and Conditions: a) K$_2$CO$_3$, ACN, rt, 12 h: b) CuSO$_4$, $^t$BuOH, H$_2$O, Sodium Ascorbate, rt, 12 h.

Scheme 7: Reagents and Conditions: a) CuSO$_4$, $^t$BuOH, H$_2$O, Sodium Ascorbate, rt, 12 h.

22(a-d)
22a; FG = 4-OCF₃
22b; FG = 4-F
22c; FG = 4-CF₃
22d; FG = 2-F

25 (a - d) (Fragment B)
25a; FG = 4-OCF₃
25b; FG = 4-F
25c; FG = 4-CF₃
25d; FG = 2-F Scheme 8: Reagents and Conditions: a) CuSO₄, ᵗBuOH, H₂O, Sodium Ascorbate, rt, 12 h.

9 (Fragment A)

(Fragment B)
23 (a - h)
24 (a - f)
25 (a- d)

IA(25- 42)
Given in Table 3

Scheme 9: Reagents and Conditions: a) NaH, DMF, 0 °C to 50 °C, 12 h.

Scheme 10: Reagents and conditions: a) NaN$_3$, HC(OEt)$_3$, CH$_3$CO$_2$H, reflux, 4 h ; b) NBS, benzoyl peroxide (cat.), CCl$_4$, reflux; c) ArB(OH)$_2$, Pd(PPh$_3$)$_4$, Na$_2$CO$_3$, PhMe-H2O-EtOH, 120 °C; d) BBr$_3$, DCM, rt, 12h.

Scheme 11: Reagents and Conditions: a) NaH, DMF, 0 °C to 50 °C, 12 h.

Scheme 12:: Reagents and conditions: a) neat, 100 °C, 2h; b) NaH, DMF, rt, 12 h; c) BBr$_3$, DCM, rt, 12 h.

Scheme 13: Reagents and Conditions: a) NaH, DMF, 0 °C to 50 °C, 12 h.

Scheme 14: Reagents and Conditions: a) NH$_2$OH.HCl, EtOH, NaOH soln, rt, 2 h; b) NCS, DMF, rt, 2 h; c) Et$_3$N, THF, rt, 24 h.

Scheme 15: Reagents and Conditions: a) NaH, DMF, 0 °C to 50 °C, 12 h.

22a; FG = 4-OCF₃
22b; FG = 4-F
22c; FG = 4-CF₃
22d; FG = 2-F
22e; FG = 4-Me
22f ; FG = 4-*iso*-propyl
22g; FG = 4-Et
22h; FG = 4-*sec*-butyl
22i ; FG = H
22j; FG = 2,4-Di-F

42a; FG = 4-OCF₃
42b; FG = 4-F
42c; FG = 4-CF₃
42d; FG = 2-F
42e; FG = 4-Me
42f ; FG = 4-*iso*-propyl
42g; FG = 4-Et
42h; FG = 4-*sec*-butyl
42i ; FG = H
42j; FG = 2,4-Di-F Scheme 16: Reagents and Conditions: a) Et₃N, THF, rt, 24 h.

Scheme 17: Reagents and Conditions: a) NaH, DMF, 0 °C to 50 °C, 12 h.

Scheme 18: Reagents and Conditions : a) DCM, rt, 12 h; b) NaH, DMF, 0 °C, 1 h, 50 °C, 3 h.

Scheme 19: Reagents and Conditions: a) NaH, DMF, 0 °C to 50 °C, 12 h.

Scheme 20: Reagents and Conditions: a) Et$_3$N, DMAP, DCM, overnight, rt; b) BBr$_3$, DCM, overnight, rt.

Scheme 21: Reagents and Conditions: a) NaH, DMF, 0 °C to 50 °C, 12 h.

Scheme 22: Reagents and Conditions: a) Et₃N, DMAP, DCM, overnight, rt; b) BBr₃, DCM, overnight, rt.

Scheme 23: Reagents and Conditions: a) NaH, DMF, 0 °C to 50 °C, 12 h.

6-NITRO-2,3-DIHYDROIMIDAZO[2,1-B] OXAZOLES AND A PROCESS FOR THE PREPARATION THEREOF

CROSS REFERENCE TO RELATED APPLICATIONS

This application is a 35 U.S.C. 371 national stage filing and claims priority to International Application No. PCT/IN2014/000202 filed on Mar. 31, 2016, entitled "6-NITRO-2,3-DIHYDROIMIDAZO[2,1-b]OXAZOLES AND A PROCESS FOR THE PREPARATION THEREOF," which claims the benefit of Indian Patent Application No. 2954/DEL/2013 filed on Oct. 4, 2013, each of which are hereby incorporated herein by reference in their entirety.

FIELD OF THE INVENTION

The present invention relates to the compounds of 6-nitro-2,3-dihydronitroimidazooxazoles scaffolds that have been designed, synthesized and their biological evaluation result for anti-tuberculosis are presented. The field of invention relates to novel compounds of general formula 1, their method of preparations, and their use as drugs for treatment of tuberculosis either alone or in combination with other anti-tubercular treatments.

BACKGROUND OF THE INVENTION

Tuberculosis remains a leading infectious cause of death worldwide and infects about one-third of the world's population. The existing TB treatment needs a cocktail of three or four different drugs (first-line drug regimen such as isoniazide, pyrazinamide, and rifampin and several second line drug regimen including ethionamide, para-aminosalicylic acid, kanamycin, amikacin, capreomycin, ciprofloxacin, streptomycin, etc.) and is exceedingly lengthy therapy which has lead to the emergence of multidrug resistant TB (MDR-TB) and extensively drug resistant TB (XDR-TB), which has further complicated the world situation [BemerMelchior, P.; Bryskier, A.; Drugeon, H. B. *J. Antimicrob. Chemother.* 2000, 46, 571; Abubaker, J.; Schraufnagel, D. *J. Am. Med. Assoc.* 2000, 283, 54; Dye. C.; Scheele, S.; Dolin, P.; Pathania, V.; Raviglione, M. C. *J. Am. Med. Assoc.* 1999, 282, 677]. The World Health Organization (WHO) has estimated that if the present conditions remain unchanged, more than 30 million lives will be claimed by TB between 2000 and 2020. TB has also been declared as a global health emergency because of the increase in secondary infections and/or coinfection in cancer and immunocompromised patients (such as those infected with human immunodeficiency virus). Therefore, the current situation necessitates the development of new and potent anti-tuberculosis agents with low toxicity profiles which are effective against both drug-susceptible and drug-resistant strains of *M. tuberculosis* along with being capable of shortening the current duration of therapy and can be used in conjunction with drugs used for treatment of secondary infections such as cancer and HIV. After four decades, US-FDA recently approved TMC-207 {bedaquiline, a diarylquinone derivative developed by Johnson & Johnson (J&J)}, first drug against MDR-TB which works by inhibiting ATP-synthase and approval of TMC-207 is being seen as a starting point for a new era of TB treatment [Edney, Anna (Dec. 31, 2012). "J&J Sirturo Wins FDA Approval to Treat Drug-Resistant TB". Bloomberg. Retrieved 2013-01-01].

In the last decade, nitroimidazole skelton (A, FIG. 1) developed great interest among the researchers of academic and industrial fields, which lead to the discovery of two anti-TB clinical candidates namely PA-824 (B, FIG. 1), a nitroimidazopyran derivative, developed by PathoGenesis Corporation [US2006087358A (2000); Stover, C. K.; Warrener, P.; VanDevanter, D. R.; Sherman, D. R.; Arain, T. M.; Michael H. Langhorne, M. H.; Anderson, S. W.; Towell, J. A.; Ying Yuan, Y.; McMurray, D. N.; Kreiswirth, B. N.; Barryk, C. E.; Baker, W. R. *Nature* 2000, 405, 962] and OPC-67683 (C, FIG. 1), a 6-nitro-2,3-dihydronitroimidazooxazole derivative, developed by Otsuka Pharmaceuticals Co. Ltd. [WO2004033463A1 (2004), EP1555267A1 (2005), WO2007013477A1 (2007); Sasaki, H.; Haraguchi, Y.; Itotani, M.; Kuroda, H.; Hashizume, H.; Tomishige, T.; Kawasaki, M.; Matsumoto, M.; Komatsu, M.; Tsubouchi, H. *J. Med. Chem.* 2006, 49, 7854]. Initially, researchers at Ciba-Geigy India started a programmne on the nitroimidazole skeleton (A, FIG. 1) to discover novel anti-tuberculosis agent and in 1989 reported a bicyclic nitroimidazooxazole (CGI 17341, D, FIG. 1) which possessed potent in vitro activity and in vivo anti-TB activity [Nagarajan, K.; Shankar, R. G.; Rajappa, S.; Shenoy, S. J.; Costa-Pereira, R. *Eur. J. Med. Chem.* 1989, 24, 631] but later discontinued due to mutagenic property [Ashtekar, D. R.; Costa-Perira, R.; Nagrajan, K.; Vishvanathan, N.; Bhatt, A. D.; Rittel, W. *Antimicrob. Agents Chemother.* 1993, 37, 183].

In present invention, new generation anti-TB molecules based on 6-nitro-2,3-dihydronitroimidazooxazoles as inherent component with triazoles, tetrazoles, isoxazoles, urea and sulphonamide functionalities are designed that may fulfill the challenges of anti-tuberculosis drug discovery such as good stability under various conditions, high oral bioavailability, good elimination half-life, free from genotoxicity/mutagenicity and hERG liabilities and absence of drug-drug interactions which is critical in combination treatments.

OBJECTIVE OF THE INVENTION

The main object of the present invention is to provide newer generation triazoles, tetrazoles, isoxazoles, urea and sulphonamide functionalities containing 6-nitro-2,3-dihydronitroimidazooxazoles agents for treatment of tuberculosis.

Still another object of the present invention is to provide a process for the preparation of triazoles, tetrazoles, isoxazoles, urea and sulphonamide functionalities containing 6-nitro-2,3-dihydronitroimidazooxazoles.

Yet another object of the present invention is to provide the combination therapy for the treatment of tuberculosis.

Still another object of the present invention is to provide treatment against multi-drug resistant (MDR) and extensive drug resistant (XDR) tuberculosis.

SUMMARY OF THE INVENTION

Accordingly the present invention relates to a compound of general formula 1 or pharmaceutically acceptable salts thereof

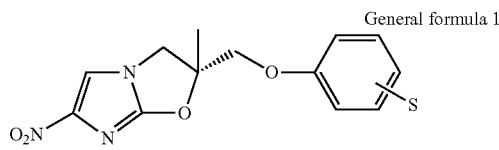

General formula 1 wherein
'S' is selected from the group consisting of formula Ia, Ib, Ic, IIa, IIb and IIc;

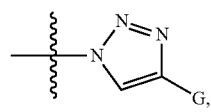
Ia

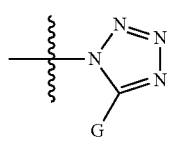
Ib

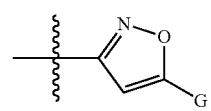
Ic

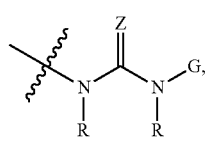
IIa

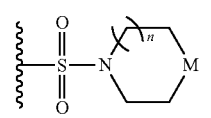
IIb

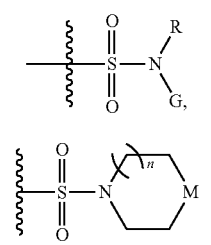
IIc wherein,
- 'G' is selected from the group consisting of H, CH$_2$OR$_1$, OR$_1$ and R$_1$;
- 'Z' is selected from the group consisting of O, S and NR$_2$;
- 'n' is any number from 0 to 2;
- 'M' is selected from the group consisting of O, S, NR$_2$ and CR$_3$R$_4$;
- R, R$_1$, and R$_2$ are each independently selected from the group consisting of H, alkyl, substituted alkyl, aryl, substituted aryl, phenyl, substituted phenyl, heterocyclic and substituted heterocyclic group selected from the group consisting of pyridyl, triazolyl, triazinyl, pyrimidinyl, pyridazinyl, oxazolyl, furanyl, benzofuranyl, thiophenyl, pyrrolyl, imidazoyl, thiazoyl, quinolinyl, isoquinolinyl, benzooxazolyl and benzothiazolyl;
- R$_3$ and R$_4$ are each independently selected from the group consisting of H, alkyl, substituted alkyl, alkoxyl, substituted alkoxyl, phenyl, substituted phenyl, phenoxyl, substituted phenoxyl, heterocyclic and substituted heterocyclic group selected from the group consisting of pyridyl, triazolyl, triazinyl, pyrimidinyl, pyridazinyl, oxazolyl, furanyl, thiophenyl, pyrrolyl, imidazoyl and thiazoyl.

In an embodiment of the present invention, the compound of general formula 1 is selected from the group consisting of compound of formula I and formula II;

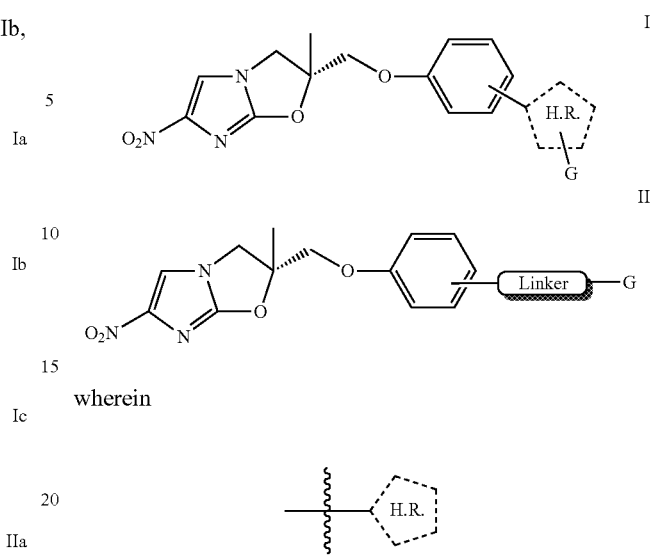

wherein

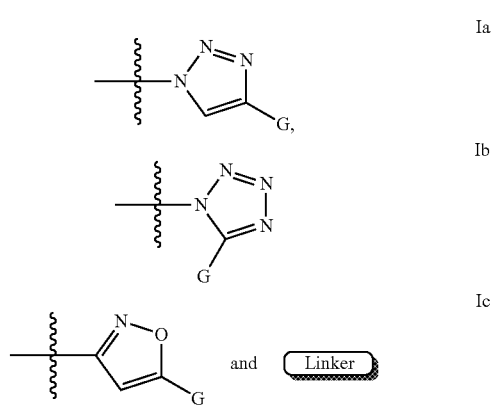

is selected from the group consisting of formula Ia, Ib and Ic;

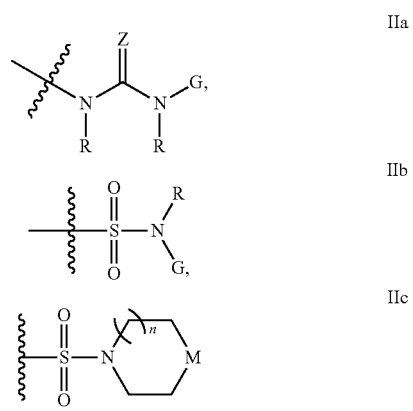

is selected from the group consisting of formula IIa, IIb and IIc;

wherein,
- 'G' is selected from the group consisting of H, CH$_2$OR$_1$, OR$_1$ and R$_1$;

'Z' is selected from the group consisting of O, S and $NR_2$;
'n' is any number from 0 to 2;
'M' is selected from the group consisting of O, S, $NR_2$, and $CR_3R_4$;
R, $R_1$ and $R_2$ are each independently selected from the group consisting of H, alkyl, substituted alkyl, aryl, substituted aryl, phenyl, substituted phenyl, heterocyclic and substituted heterocyclic group selected from the group consisting of pyridyl, triazolyl, triazinyl, pyrimidinyl, pyridazinyl, oxazolyl, furanyl, benzofuranyl, thiophenyl, pyrrolyl, imidazoyl, thiazoyl, quinolinyl, isoquinolinyl, benzooxazolyl, and benzothiazolyl;
$R_3$ and $R_4$ are each independently selected from the group consisting of H, alkyl, substituted alkyl, alkoxyl, substituted alkoxyl, phenyl, substituted phenyl, phenoxyl, substituted phenoxyl, heterocyclic and substituted heterocyclic group selected from the group consisting of pyridyl, triazolyl, triazinyl, pyrimidinyl, pyridazinyl, oxazolyl, furanyl, thiophenyl, pyrrolyl, imidazoyl and thiazoyl.

In still another embodiment of the present invention, the compound of formula I is selected from the group consisting of formula IA, IB and IC,

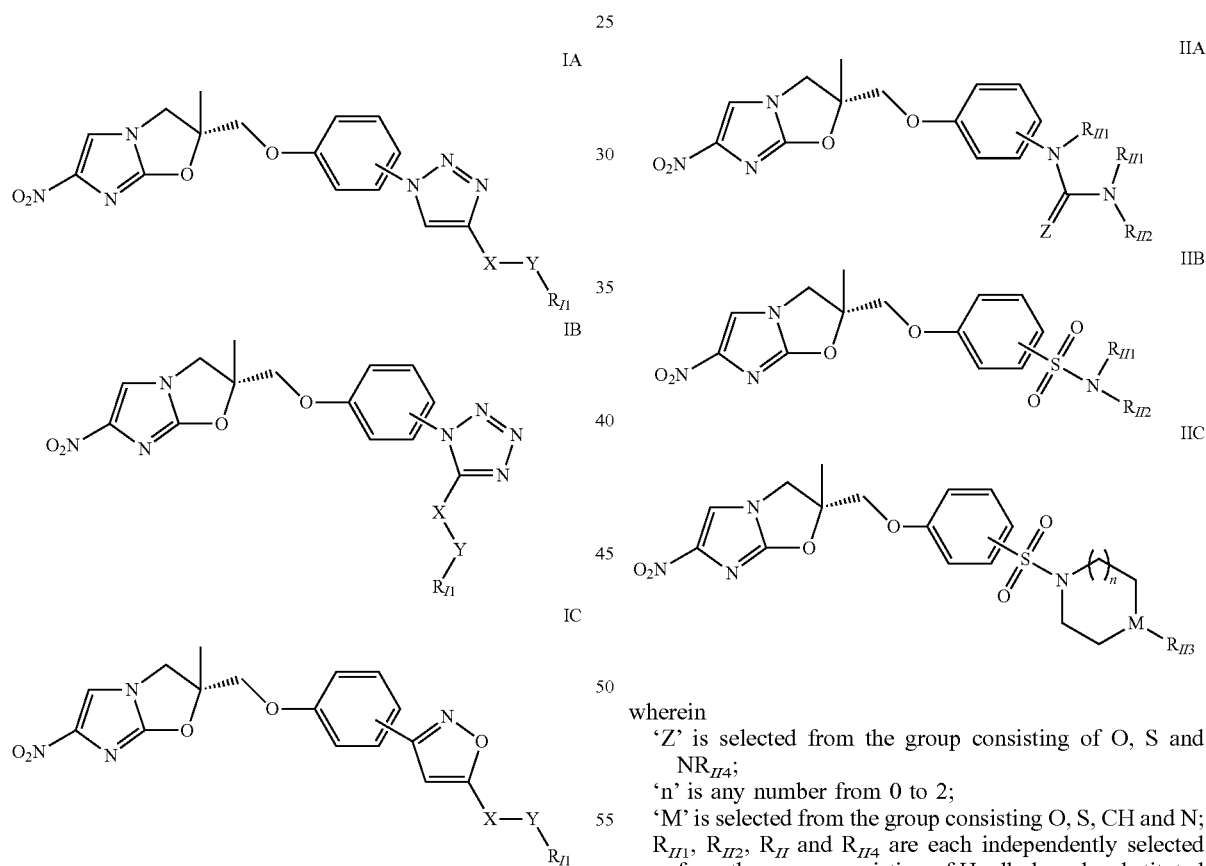

wherein
'X' is $CH_2$ or a direct bond;
'Y' is selected from the group consisting of O, S, and $NR_{I2}$, or a direct bond;
$R_{I1}$ is selected from the group consisting of H, alkyl, aryl, substituted alkyl, substituted aryl, heterocyclic, substituted hetercyclic group selected from the group consisting of pyridyl, triazolyl, triazinyl, pyrimidinyl, pyridazinyl, oxazolyl, furanyl, benzofuranyl, thiophenyl, pyrrolyl, imidazoyl, thiazoyl, quinolinyl, isoquinolinyl, benzooxazolyl, and benzothiazolyl; and substituted aryl is selected from the group consisting of F, Cl, Br, I, $NR_{I3}R_{I4}$, $CF_3$, $OCF_3$, $OR_{I5}$, $NO_2$, $CHR_{I6}R_{I7}$, alkyl group having C1 to C14, $COOR_{I8}$, CHO, and $COR_{I9}$;
$R_{I2}$, $R_{I3}$, $R_{I4}$, $R_{I5}$, $R_{I8}$ and $R_{I9}$ are each independently selected from the group consisting of H, alkyl, alkoxyl, substituted alkoxyl, phenyl, substituted phenyl, phenoxyl, substituted phenoxyl, heterocyclic and substituted heterocyclic group selected from the group consisting of pyridyl, triazolyl, triazinyl, pyrimidinyl, pyridazinyl, oxazolyl, furanyl, thiophenyl, pyrrolyl, imidazoyl and thiazoyl;
$R_{I6}$ and $R_{I7}$ are each independently selected from the group consisting of H, alkyl, phenyl, substituted phenyl, heterocyclic and substituted heterocyclic group selected from the group consisting of pyridyl, triazolyl, triazinyl, pyrimidinyl, pyridazinyl, oxazolyl, furanyl, thiophenyl, pyrrolyl, imidazoyl and thiazoyl.

In yet another embodiment of the present invention, the compound of formula II is selected from the group consisting of compound of formula IIA, IIB and IIC, wherein
'Z' is selected from the group consisting of O, S and $NR_{II4}$;
'n' is any number from 0 to 2;
'M' is selected from the group consisting O, S, CH and N;
$R_{II1}$, $R_{II2}$, $R_{II}$ and $R_{II4}$ are each independently selected from the group consisting of H, alkyl, aryl, substituted alkyl, substituted aryl, heterocyclic and substituted hetercyclic group selected from the group consisting of pyridyl, triazolyl, triazinyl, pyrimidinyl, pyridazinyl, oxazolyl, furanyl, benzofuranyl, thiophenyl, pyrrolyl, imidazoyl, thiazoyl, quinolinyl, isoquinolinyl, benzooxazolyl, and benzothiazolyl; and substituted aryl is selected from the group consisting of F, Cl, Br, I, $NR_{II5}R_{II6}$, $CF_3$, $OCF_3$, $OR_{II7}$, $NO_2$, $CHR_{II8}R_{II9}$, alkyl group having C1 to C14, $COOR_{II10}$, CHO, and $COR_{II11}$;

$R_{H5}$, $R_{H6}$, $R_{H7}$, $R_{H10}$ and $R_{H11}$ are each independently selected from the group consisting of H, alkyl, phenyl, substituted phenyl, heterocyclic and substituted heterocyclic group selected from the group consisting of pyridyl, triazolyl, triazinyl, pyrimidinyl, pyridazinyl, oxazolyl, furanyl, thiophenyl, pyrrolyl, imidazoyl and thiazoyl;

$R_{H8}$ and $R_{H9}$ are each independently selected from the group consisting of H, alkyl, alkoxy, substituted alkoxy, phenyl, substituted phenyl, phenoxy, substituted phenoxy, heterocyclic and substituted heterocyclic group selected from the group consisting of pyridyl, triazolyl, triazinyl, pyrimidinyl, pyridazinyl, oxazolyl, furanyl, thiophenyl, pyrrolyl, imidazoyl and thiazoyl.

In still another embodiment of the present invention, the compounds of general formula 1 are selected from the group consisting of:

(R)-2-{4-(4-phenyl-1H-1,2,3-triazol-1-yl)phenoxy)methyl}-2,3-dihydro-2-methyl-6-nitroimidazo[2,1-b]oxazole (compound IA1), (R)-2-{4-[4-(4-ethylphenyl)-1H-1,2,3-triazol-1-yl]phenoxymethyl}-2,3-dihydro-2-methyl-6-nitroimidazo[2,1-b]oxazole (compound IA2), (R)-2-{4-[4-(4-fluorophenyl)-1H-1,2,3-triazol-1-yl]phenoxymethyl}-2,3-dihydro-2-methyl-6-nitroimidazo[2,1-b]oxazole (compound IA3), (R)-2-{4-[4-(2-fluorophenyl)-1H-1,2,3-triazol-1-yl]phenoxymethyl}-2,3-dihydro-2-methyl-6-nitroimidazo[2,1-b]oxazole (compound IA4), (R)-2-{4-[4-(4-trifluoromethoxyphenyl)-1H-1,2,3-triazol-1-yl]phenoxymethyl}-2,3-dihydro-2-methyl-6-nitroimidazo[2,1-b]oxazole (compound IA5), (R)-2-{4-[4-(2-trifluoromethylphenyl)-1H-1,2,3-triazol-1-yl]phenoxymethyl}-2,3-dihydro-2-methyl-6-nitroimidazo[2,1-b]oxazole (compound IA6), (R)-2-{4-[4-(2,4-difluorophenyl)-1H-1,2,3-triazol-1-yl]phenoxymethyl}-2,3-dihydro-2-methyl-6-nitroimidazo[2,1-b]oxazole (compound IA7), (R)-2-{4-[4-(4-methylphenyl)-1H-1,2,3-triazol-1-yl]phenoxymethyl}-2,3-dihydro-2-methyl-6-nitroimidazo[2,1-b]oxazole (compound IA8), (R)-2-{4-[4-(4-isopropylphenyl)-1H-1,2,3-triazol-1-yl]phenoxymethyl}-2,3-dihydro-2-methyl-6-nitroimidazo[2,1-b]oxazole (compound IA9), (R)-2-{4-[4-(3-fluorophenyl)-1H-1,2,3-triazol-1-yl]phenoxymethyl}-2,3-dihydro-2-methyl-6-nitroimidazo[2,1-b]oxazole (compound IA10), (R)-2-{4-[4-(4-methoxyphenyl)-1H-1,2,3-triazol-1-yl]phenoxymethyl}-2,3-dihydro-2-methyl-6-nitroimidazo[2,1-b]oxazole (compound IA11), (R)-2-{4-[4-(3-trifluoromethoxyphenyl)-1H-1,2,3-triazol-1-yl]phenoxymethyl}-2,3-dihydro-2-methyl-6-nitroimidazo[2,1-b]oxazole (compound IA12), (R)-2-{4-[4-(3-trifluoromethylphenyl)-1H-1,2,3-triazol-1-yl]phenoxymethyl}-2,3-dihydro-2-methyl-6-nitroimidazo[2,1-b]oxazole (compound IA13), (R)-2-{4-[4-(4-pyridin-2-yl)-1H-1,2,3-triazol-1-yl]phenoxymethyl}-2,3-dihydro-2-methyl-6-nitroimidazo[2,1-b]oxazole (compound IA14), (R)-2-{4-[4-pentyl-1H-1,2,3-triazol-1-yl]phenoxymethyl}-2,3-dihydro-2-methyl-6-nitroimidazo[2,1-b]oxazole (compound IA15), (R)-2-{4-[4-heptyl-1H-1,2,3-triazol-1-yl]phenoxymethyl}-2,3-dihydro-2-methyl-6-nitroimidazo[2,1-b]oxazole (compound IA16), (R)-2-{3-[4-(4-fluorophenyl)-1H-1,2,3-triazol-1-yl]phenoxymethyl}-2,3-dihydro-2-methyl-6-nitroimidazo[2,1-b]oxazole (compound IA17), (R)-2-{3-[4-(4-trifluoromethylphenyl)-1H-1,2,3-triazol-1-yl]phenoxymethyl}-2,3-dihydro-2-methyl-6-nitroimidazo[2,1-b]oxazole (compound IA18), (R)-2-{3-[4-(4-trifluoromethoxyphenyl)-1H-1,2,3-triazol-1-yl]phenoxymethyl}-2,3-dihydro-2-methyl-6-nitroimidazo[2,1-b]oxazole (compound IA19), (R)-2-{3-[4-(2,4-difluorophenyl)-1H-1,2,3-triazol-1-yl]phenoxymethyl}-2,3-dihydro-2-methyl-6-nitroimidazo[2,1-b]oxazole (compound IA20), (R)-2-{2-[4-(4-fluorophenyl)-1H-1,2,3-triazol-1-yl]phenoxymethyl}-2,3-dihydro-2-methyl-6-nitroimidazo[2,1-b]oxazole (compound IA21), (R)-2-{2-[4-(4-trifluoromethylphenyl)-1H-1,2,3-triazol-1-yl]phenoxymethyl}-2,3-dihydro-2-methyl-6-nitroimidazo[2,1-b]oxazole (compound IA22), (R)-2-{2-[4-(4-trifluoromethoxyphenyl)-1H-1,2,3-triazol-1-yl]phenoxymethyl}-2,3-dihydro-2-methyl-6-nitroimidazo[2,1-b]oxazole (compound IA23), (R)-2-{2-[4-(2,4-difluorophenyl)-1H-1,2,3-triazol-1-yl]phenoxymethyl}-2,3-dihydro-2-methyl-6-nitroimidazo[2,1-b]oxazole (compound IA24), (R)-2-{4-[4-(4-trifluoromethoxyphenoxy)methyl)-1H-1,2,3-triazol-1-yl]phenoxymethyl}-2,3-dihydro-2-methyl-6-nitroimidazo[2,1-b]oxazole (compound IA25), (R)-2-{4-[4-(4-fluorophenoxy)methyl)-1H-1,2,3-triazol-1-yl]phenoxymethyl}-2,3-dihydro-2-methyl-6-nitroimidazo[2,1-b]oxazole (compound IA26), (R)-2-{4-[4-(4-trifluoromethylphenoxy)methyl)-1H-1,2,3-triazol-1-yl]phenoxymethyl}-2,3-dihydro-2-methyl-6-nitroimidazo[2,1-b]oxazole (compound IA27), (R)-2-{4-[4-(2-fluorophenoxy)methyl)-1H-1,2,3-triazol-1-yl]phenoxymethyl}-2,3-dihydro-2-methyl-6-nitroimidazo[2,1-b]oxazole (compound IA28), (R)-2-{4-[4-(4-methylphenoxy)methyl)-1H-1,2,3-triazol-1-yl]phenoxymethyl}-2,3-dihydro-2-methyl-6-nitroimidazo[2,1-b]oxazole (compound IA29), (R)-2-{4-[4-(4-isopropylphenoxy)methyl)-1H-1,2,3-triazol-1-yl]phenoxymethyl}-2,3-dihydro-2-methyl-6-nitroimidazo[2,1-b]oxazole (compound IA30), (R)-2-{4-[4-(4-ethylphenoxy)methyl)-1H-1,2,3-triazol-1-yl]phenoxymethyl}-2,3-dihydro-2-methyl-6-nitroimidazo[2,1-b]oxazole (compound IA31), (R)-2-{4-[4-(4-sec-butylphenoxy)methyl)-1H-1,2,3-triazol-1-yl]phenoxymethyl}-2,3-dihydro-2-methyl-6-nitroimidazo[2,1-b]oxazole (compound IA32), (R)-2-{3-[4-(4-trifluoromethoxyphenoxy)methyl)-1H-1,2,3-triazol-1-yl]phenoxymethyl}-2,3-dihydro-2-methyl-6-nitroimidazo[2,1-b]oxazole (compound IA33), (R)-2-{3-[4-(4-fluorophenoxy)methyl)-1H-1,2,3-triazol-1-yl]phenoxymethyl}-2,3-dihydro-2-methyl-6-nitroimidazo[2,1-b]oxazole (compound IA34), (R)-2-{3-[4-(4-trifluoromethylphenoxy)methyl)-1H-1,2,3-triazol-1-yl]phenoxymethyl}-2,3-dihydro-2-methyl-6-nitroimidazo[2,1-b]oxazole (compound IA35), (R)-2-{3-[4-(2-fluorophenoxy)methyl)-1H-1,2,3-triazol-1-yl]phenoxymethyl}-2,3-dihydro-2-methyl-6-nitroimidazo[2,1-b]oxazole (compound IA36), (R)-2-{3-[4-(4-methylphenoxy)methyl)-1H-1,2,3-triazol-1-yl]phenoxymethyl}-2,3-dihydro-2-methyl-6-nitroimidazo[2,1-b]oxazole (compound IA37), (R)-2-{3-[4-(4-isopropylphenoxy)methyl)-1H-1,2,3-triazol-1-yl]phenoxymethyl}-2,3-dihydro-2-methyl-6-nitroimidazo[2,1-b]oxazole (compound IA38), (R)-2-{2-[4-(4-trifluoromethoxyphenoxy)methyl)-1H-1,2,3-triazol-1-yl]phenoxymethyl}-2,3-dihydro-2-methyl-6-nitroimidazo[2,1-b]oxazole (compound IA39),
(R)-2-{2-[4-(4-fluorophenoxy)methyl)-1H-1,2,3-triazol-1-yl]phenoxymethyl}-2,3-dihydro-2-methyl-6-nitroimidazo[2,1-b]oxazole (compound IA40),
(R)-2-{2-[4-(4-trifluoromethylphenoxy)methyl)-1H-1,2,3-triazol-1-yl]phenoxymethyl}-2,3-dihydro-2-methyl-6-nitroimidazo[2,1-b]oxazole (compound IA41),
(R)-2-{2-[4-(2-fluorophenoxy)methyl)-1H-1,2,3-triazol-1-yl]phenoxymethyl}-2,3-dihydro-2-methyl-6-nitroimidazo[2,1-b]oxazole (compound IA42),
(R)-2-{4-[5-phenyl-1H-tetrazol-1-yl]phenoxymethyl}-2,3-dihydro-2-methyl-6-nitroimidazo[2,1-b]oxazole (compound IB1),
(R)-2-{4-[5-(4-trifluoromethoxyphenyl)-1H-tetrazol-1-yl]phenoxymethyl}-2,3-dihydro-2-methyl-6-nitroimidazo[2,1-b]oxazole (compound IB2),
(R)-2-{4-[5-(4-methylphenyl)-1H-tetrazol-1-yl]phenoxymethyl}-2,3-dihydro-2-methyl-6-nitroimidazo[2,1-b]oxazole (compound IB3),
(R)-2-{4-[5-(4-fluorophenyl)-1H-tetrazol-1-yl]phenoxymethyl}-2,3-dihydro-2-methyl-6-nitroimidazo[2,1-b]oxazole (compound IB4),
(R)-2-{4-[5-(4-trifluoromethylphenyl)-1H-tetrazol-1-yl]phenoxymethyl}-2,3-dihydro-2-methyl-6-nitroimidazo[2,1-b]oxazole (compound IB5),
(R)-2-{4-[5-(4-ethylphenyl)-1H-tetrazol-1-yl]phenoxymethyl}-2,3-dihydro-2-methyl-6-nitroimidazo[2,1-b]oxazole (compound IB6),
(R)-2-{4-[5-(4-fluorophenoxy)-1H-tetrazol-1-yl]phenoxymethyl}-2,3-dihydro-2-methyl-6-nitroimidazo[2,1-b]oxazole (compound IB7),
(R)-2-{4-[5-(4-trifluoromethylphenoxy)-1H-tetrazol-1-yl]phenoxymethyl}-2,3-dihydro-2-methyl-6-nitroimidazo[2,1-b]oxazole (compound IB8),
(R)-2-{4-[5-(4-methylphenoxy)-1H-tetrazol-1-yl]phenoxymethyl}-2,3-dihydro-2-methyl-6-nitroimidazo[2,1-b]oxazole (compound IB9),
(R)-2-{4-[5-(4-trifluoromethoxyphenoxy)-1H-tetrazol-1-yl]phenoxymethyl}-2,3-dihydro-2-methyl-6-nitroimidazo[2,1-b]oxazole (compound IB10),
(R)-2-{4-[5-phenylisoxazol-3-yl]phenoxymethyl}-2,3-dihydro-2-methyl-6-nitroimidazo[2,1-b]oxazole (compound IC1),
(R)-2-{4-[5-(4-ethylphenyl)isoxazol-3-yl]phenoxymethyl}-2,3-dihydro-2-methyl-6-nitroimidazo[2,1-b]oxazole (compound IC2),
(R)-2-{4-[5-(2,4-difluorophenyl)isoxazol-3-yl]phenoxymethyl}-2,3-dihydro-2-methyl-6-nitroimidazo[2,1-b]oxazole (compound IC3),
(R)-2-{4-[5-(2-fluorophenyl)isoxazol-3-yl]phenoxymethyl}-2,3-dihydro-2-methyl-6-nitroimidazo[2,1-b]oxazole (compound IC4),
(R)-2-{4-[5-(4-trifluoromethylphenyl)isoxazol-3-yl]phenoxymethyl}-2,3-dihydro-2-methyl-6-nitroimidazo[2,1-b]oxazole (compound IC5),
(R)-2-{4-[5-(4-methylphenyl)isoxazol-3-yl]phenoxymethyl}-2,3-dihydro-2-methyl-6-nitroimidazo[2,1-b]oxazole (compound IC6),
(R)-2-{4-[5-(4-methoxyphenyl)isoxazol-3-yl]phenoxymethyl}-2,3-dihydro-2-methyl-6-nitroimidazo[2,1-b]oxazole (compound IC7),
(R)-2-{4-[5-(3-fluorophenyl)isoxazol-3-yl]phenoxymethyl}-2,3-dihydro-2-methyl-6-nitroimidazo[2,1-b]oxazole (compound IC8),
(R)-2-{4-[5-(pyridin-2-yl)isoxazol-3-yl]phenoxymethyl}-2,3-dihydro-2-methyl-6-nitroimidazo[2,1-b]oxazole (compound IC9),
(R)-2-{4-[5-(4-trifluoromethoxyphenyl)isoxazol-3-yl]phenoxymethyl}-2,3-dihydro-2-methyl-6-nitroimidazo[2,1-b]oxazole (compound IC10),
(R)-2-{4-[5-pentylisoxazol-3-yl]phenoxymethyl}-2,3-dihydro-2-methyl-6-nitroimidazo[2,1-b]oxazole (compound IC11),
(R)-2-{4-[5-heptylisoxazol-3-yl]phenoxymethyl}-2,3-dihydro-2-methyl-6-nitroimidazo[2,1-b]oxazole (compound IC12),
(R)-2-{4-[5-(4-trifluoromethoxyphenoxymethyl)isoxazol-3-yl]phenoxymethyl}-2,3-dihydro-2-methyl-6-nitroimidazo[2,1-b]oxazole (compound IC13),
(R)-2-{4-[5-(4-fluorophenoxymethyl)isoxazol-3-yl]phenoxymethyl}-2,3-dihydro-2-methyl-6-nitroimidazo[2,1-b]oxazole (compound IC14),
(R)-2-{4-[5-(4-trifluoromethylphenoxymethyl)isoxazol-3-yl]phenoxymethyl}-2,3-dihydro-2-methyl-6-nitroimidazo[2,1-b]oxazole (compound IC15),
(R)-2-{4-[5-(2-fluorophenoxymethyl)isoxazol-3-yl]phenoxymethyl}-2,3-dihydro-2-methyl-6-nitroimidazo[2,1-b]oxazole (compound IC16),
(R)-2-{4-[5-(4-methylphenoxymethyl)isoxazol-3-yl]phenoxymethyl}-2,3-dihydro-2-methyl-6-nitroimidazo[2,1-b]oxazole (compound IC17),
(R)-2-{4-[5-(4-isopropylphenoxymethyl)isoxazol-3-yl]phenoxymethyl}-2,3-dihydro-2-methyl-6-nitroimidazo[2,1-b]oxazole (compound IC18),
(R)-2-{4-[5-(4-ethylphenoxymethyl)isoxazol-3-yl]phenoxymethyl}-2,3-dihydro-2-methyl-6-nitroimidazo[2,1-b]oxazole (compound IC19),
(R)-2-{4-[5-(4-sec-butylphenoxymethyl)isoxazol-3-yl]phenoxymethyl}-2,3-dihydro-2-methyl-6-nitroimidazo[2,1-b]oxazole (compound IC20),
(R)-2-{4-[5-(phenoxymethyl)isoxazol-3-yl]phenoxymethyl}-2,3-dihydro-2-methyl-6-nitroimidazo[2,1-b]oxazole (compound IC21),
(R)-2-{4-[5-(2,4-difluorophenoxymethyl)isoxazol-3-yl]phenoxymethyl}-2,3-dihydro-2-methyl-6-nitroimidazo[2,1-b]oxazole (compound IC22),
(R)-1-(4-fluorophenyl)-3-{4-(2-methyl-6-nitro-2,3-dihydroimidazo[2,1-b]oxazol-2-yl)methoxyphenyl}urea (compound IIA1),
(R)-1-(4-ethylphenyl)-3-{4-(2-methyl-6-nitro-2,3-dihydroimidazo[2,1-b]oxazol-2-yl)methoxyphenyl}urea (compound IIA2),
(R)-1-(4-trifluoromethylphenyl)-3-{4-(2-methyl-6-nitro-2,3-dihydroimidazo[2,1-b]oxazol-2-yl)methoxyphenyl}urea (compound IIA3),
(R)-1-(4-methylphenyl)-3-{4-(2-methyl-6-nitro-2,3-dihydroimidazo[2,1-b]oxazol-2-yl)methoxyphenyl}urea (compound IIA4),
(R)-1-(4-methoxyphenyl)-3-{4-(2-methyl-6-nitro-2,3-dihydroimidazo[2,1-b]oxazol-2-yl)methoxyphenyl}urea (compound IIA5),
(R)-1-(4-trifluoromethoxyphenyl)-3-{4-(2-methyl-6-nitro-2,3-dihydroimidazo[2,1-b]oxazol-2-yl)methoxyphenyl}urea (compound IIA6),
(R)-1-(4-methoxyphenyl)-3-{4-(2-methyl-6-nitro-2,3-dihydroimidazo[2,1-b]oxazol-2-yl)methoxyphenyl}thiourea (compound IIA7),
(R)-1-(4-trifluoromethoxyphenyl)-3-{4-(2-methyl-6-nitro-2,3-dihydroimidazo[2,1-b]oxazol-2-yl)methoxyphenyl}thiourea (compound IIA8), (R)-1-(4-fluorophenyl)-3-{4-(2-methyl-6-nitro-2,3-dihydroimidazo[2,1-b]oxazol-2-yl)methoxyphenyl}thiourea (compound IIA9),
(R)-1-(4-trifluoromethylphenyl)-3-{4-(2-methyl-6-nitro-2,3-dihydroimidazo[2,1-b]oxazol-2-yl)methoxyphenyl}thiourea (compound IIA10),
(R)-4-{(2-methyl-6-nitro-2,3-dihydroimidazo[2,1-b]oxazol-2-yl)methoxy}-N-(p-tolyl)benzenesulfonamide (compound IIB1),
(R)-4-{(2-methyl-6-nitro-2,3-dihydroimidazo[2,1-b]oxazol-2-yl)methoxy}-N-(p-trifluoromethoxyphenyl)benzenesulfonamide (compound IIB2),
(R)-4-{(2-methyl-6-nitro-2,3-dihydroimidazo[2,1-b]oxazol-2-yl)methoxy}-N-(p-trifluoromethylphenyl)benzenesulfonamide (compound IIB3),
(R)—N-methyl-4-{(2-methyl-6-nitro-2,3-dihydroimidazo[2,1-b]oxazol-2-yl)methoxy}-N-phenylbenzenesulfonamide (compound IIB4),
(R)—N-methyl-4-{(2-methyl-6-nitro-2,3-dihydroimidazo[2,1-b]oxazol-2-yl)methoxy}-N-(p-tolyl)benzenesulfonamide (compound IIB5),
(R)—N-methyl-4-{(2-methyl-6-nitro-2,3-dihydroimidazo[2,1-b]oxazol-2-yl)methoxy}-N-(p-trifluoromethylphenyl)benzenesulfonamide (compound IIB6),
(R)-2-{4-(4-phenylpiperazin-1-yl)sulfonylphenoxymethyl}-2,3-dihydro-2-methyl-6-nitroimidazo[2,1-b]oxazole (compound IIC1),
(R)-2-{4-[4-(4-fluorophenyl)piperazin-1-yl]sulfonylphenoxymethyl}-2,3-dihydro-2-methyl-6-nitroimidazo[2,1-b]oxazole (compound IIC2),
(R)-2-{4-[4-(3-chlorophenyl)piperazin-1-yl]sulfonylphenoxymethyl}-2,3-dihydro-2-methyl-6-nitroimidazo[2,1-b]oxazole (compound IIC3),
(R)-2-{4-[4-(4-trifluoromethoxyphenyppiperazin-1-yl]sulfonylphenoxymethyl}-2,3-dihydro-2-methyl-6-nitroimidazo[2,1-b]oxazole (compound IIC4),
(R)-ethyl-{4-[4-(2-methyl-6-nitro-2,3-dihydroimidazo[2,1-b]oxazol-2yl)methoxyphenyl]sulfonyl}piperazine-1-carboxylate (compound IIC5),
(R)-{4-[4-(2-methyl-6-nitro-2,3-dihydroimidazo[2,1-b]oxazol-2yl)methoxyphenyl]sulfonyl}piperazine-1-yl(phenyl)methanone (compound IIC6),
(R)-2-{4-(piperidin-1-ylsulfonyl)phenoxymethyl}-2,3-dihydro-2-methyl-6-nitroimidazo[2,1-b]oxazole (compound IIC7),
(R)-2-{4-[(4-phenylpiperidin-1-yl)sulfonyl]phenoxymethyl}-2,3-dihydro-2-methyl-6-nitroimidazo[2,1-b]oxazole (compound IIC8),
(R)-2-{4-(pyrrolidin-1-ylsulfonyl)phenoxymethyl}-2,3-dihydro-2-methyl-6-nitroimidazo[2,1-b]oxazole (compound IIC9) and
(R)-2-{4-(morpholinsulfonyl)phenoxymethyl}-2,3-dihydro-2-methyl-6-nitroimidazo[2,1-b]oxazole (compound IIC10)

In yet another embodiment of the present invention, the compound of general formula 1 is useful in treatment of tuberculosis.

In still another embodiment of the present invention, the compound of general formula 1 exhibits an in vitro anti-tuberculosis activity against H37Rv *Mycobacterium tuberculosis*, MDR (resistant to isoniazid and rifampicin) with MIC values in the range of 0.06 to 32 µg/ml.

In yet another embodiment of present invention, the compound of general formula 1 exhibits an in vitro anti-tuberculosis activity against XDR *Mycobacterium tuberculosis* (resistant to isoniazid, rifampicin, amikacin and moxifloxacin) with MIC values in the range of 0.12 to 32 µg/ml.

In still another embodiment of the present invention, the compound of general formula 1 does not exhibit any cytotoxicity up to 40 µg/ml in macrophage J774 cells line and exhibits safety index more than 10.

In yet another embodiment of the present invention, the compound of general formula 1 shows promising pharmacokinetic properties in mouse model with $C_{max}$ of 1 to 5 µg/ml and $AUC_{0-24}$ of 10 to 50 µg hr/ml at oral dose of 5 mg/kg.

In still another embodiment of the present invention, the compound of general formula 1 exhibits synergistic and additive effect with known anti-tubercular drugs in combination studies.

An embodiment of the present invention provides a process for the preparation of a compound of general formula 1 comprising the steps:
reacting an epoxide (compound 9)

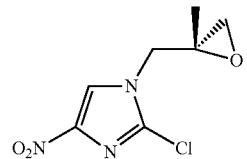

compound 9 with a substituted phenol selected from the group consisting of compounds of formula 13(a-p), 16(a-d), 19(a-d), 23 (a-h), 24(a-f), 25(a-d), 30(a-f), 36(a-d), 41(a-l), 42(a-j), 45(a-j), 49(a-f) and 53(a-j) in an organic solvent selected from the group consisting of N,N-dimethylformamide, DCM, acetonitrile, THF and acetone in presence of a base selected from the group consisting of sodium hydride, cesium carbonate, potassium carbonate and potassium bicarbonate at a temperature in the range of −20° C. to 10° C. and stirring for a period ranging between 1 to 24 hrs at a temperature in the range of 50° C. to 80° C. to obtain the compound of general formula 1.

In yet another embodiment of the present invention, the pharmaceutically acceptable salts are salts of an acid selected from the group consisting of hydrochloric acid, sulfuric acid, phosphoric acid, acetic acid, citric acid, oxalic acid, malonic acid, salicylic acid, malic acid, fumaric acid, succinic acid, ascorbic acid, maleic acid, methanesulfonic acid and isoethonic acid and salts of a base selected from the group consisting of potassium carbonate, sodium hydroxide, potassium hydroxide, ammonia, triethylamine and triethanolamine.

In still another embodiment of the present invention, the process for the preparation of the salt of compound of general formula 1 comprising the steps:
mixing a compound of general formula 1 with an acid or a base in the ratio of 1:1 by weight wherein, said acid is selected from the group consisting of hydrochloric acid, sulfuric acid, phosphoric acid, acetic acid, citric acid, oxalic acid, malonic acid, salicylic acid, malic acid, fumaric acid, succinic acid, ascorbic acid, maleic acid and methanesulfonic acid and said base is selected from the group consisting of sodium hydroxide, potassium hydroxide and ammonium hydroxide, in water to obtain a reaction mixture;
stirring said reaction mixture for 1-2 hrs followed by evaporating water to obtain the salt of compound of formula 1.

An embodiment of the present invention provides a pharmaceutical composition for treatment of tuberculosis comprising an effective amount of a compound of general formula 1 or a combination of a compound of general formula 1 and an anti-tubercular drug, optionally along with pharmaceutically acceptable diluents, excipients or carriers.

In still another embodiment of the present invention, the ratio of compound of formula 1 and an anti-tubercular drug in the pharmaceutical composition is in the range of 0.1% to 50% by weight.

In yet another embodiment of the present invention, the anti-tubercular drug used in the pharmaceutical composition is selected from the group consisting of ethambutal, INH, rifampicin, pyrazinamide, streptomycin, capreomycin, viomycin, enviomycin, kanamycin, amikacin, ethionamide, prothionamide, p-amino salicylic acid, closerine, ciprofloxacin, levoflaxacin and moxiflaxacin.

An embodiment of the present invention provides a method of treating tuberculosis comprising administering to a subject, an effective amount of a compound of general formula 1 or a combination of a compound of general formula 1 and an anti-tubercular drug, optionally along with pharmaceutically acceptable diluents, excipients or carriers.

In an embodiment of the present invention, there is provided a method for treating tuberculosis, wherein the subject is a human.

In another embodiment of the present invention, there is provided a method for treating tuberculosis, wherein the anti-tubercular drug used in combination with the compound of formula 1 is selected from the group consisting of ethambutal, INH, rifampicin, pyrazinamide, streptomycin, capreomycin, viomycin, enviomycin, kanamycin, amikacin, ethionamide, prothionamide, p-amino salicylic acid, closerine, ciprofloxacin, levoflaxacin and moxiflaxacin.

BRIEF DESCRIPTION OF THE TABLES

Figure 8:
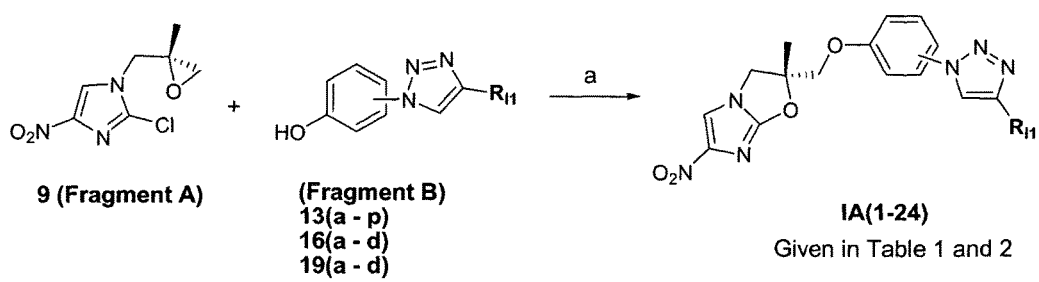
FIG. 8 shows the synthetic scheme (Scheme 5) for coupling of A (compound 9) with B [compound 13(a-p), 16(a-d), 19(a-d)] to generate the representing compounds of formula IA of general formula 1.

Table 1 shows the structure of representative compounds IA1-IA16 belonging to formula IA and synthesized as per scheme 5 provided in FIG. 8.

Table 2 shows the structure of representative compounds IA17-IA24 belonging to formula IA and synthesized as per scheme 5 provided in FIG. 8.

Figure 12:
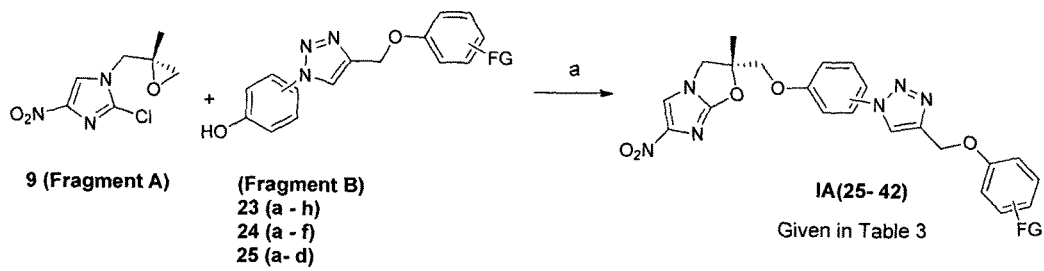
FIG. 12 shows the synthetic scheme (Scheme 9) for coupling of A (compound 9) with B [compound 23(a-h), 24(a-f), 25(a-d)] to generate the representing compounds of formula IA of general formula 1.

Table 3 shows the structure of representative compounds IA25-IA42 belonging to formula IA and synthesized as per scheme 9 provided in FIG. 12.

Figure 14:
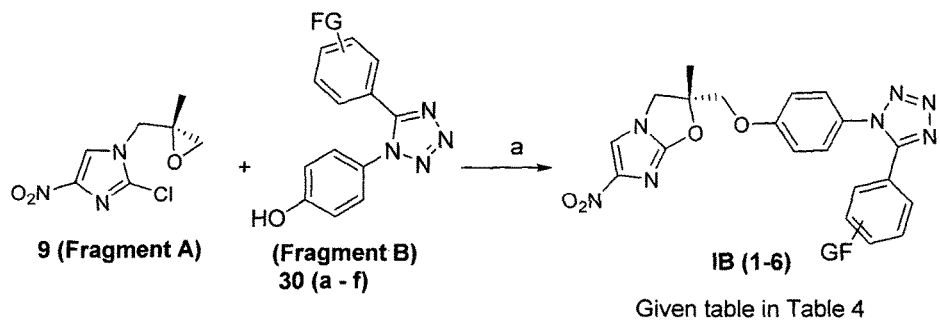
FIG. 14 shows the synthetic scheme (Scheme 11) for coupling of A (compound 9) with B [compound 30(a-f)] to generate the representing compounds of formula IB of general formula 1.
Figure 16:
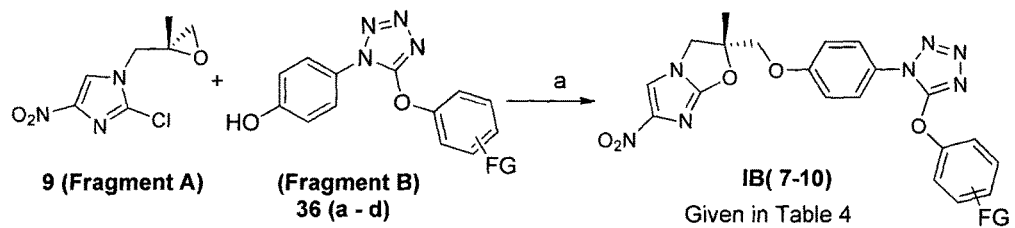
FIG. 16 shows the synthetic scheme (Scheme 13) for coupling of A (compound 9) with B [compound 36(a-d)] to generate the representing compounds of formula IB of general formula 1.

Table 4 shows the structure of representative compounds IB1-IB10 belonging to formula IB and synthesized as per scheme 11 and scheme 13 provided in FIG. 14 and FIG. 16, respectively.

Figure 18:
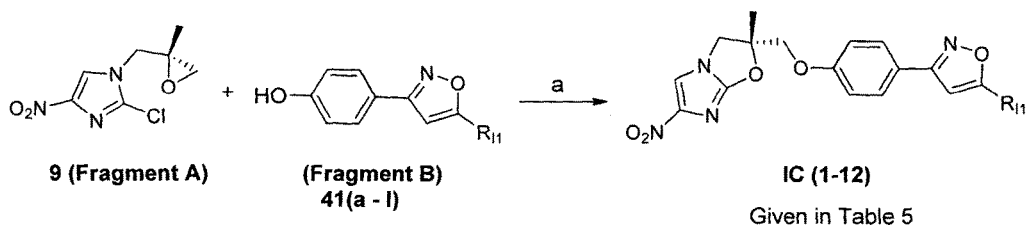
FIG. 18 shows the synthetic scheme (Scheme 15) for coupling of A (compound 9) with B [compound 41(a-l)] to generate the representing compounds of formula IC of general formula 1.
Figure 20:
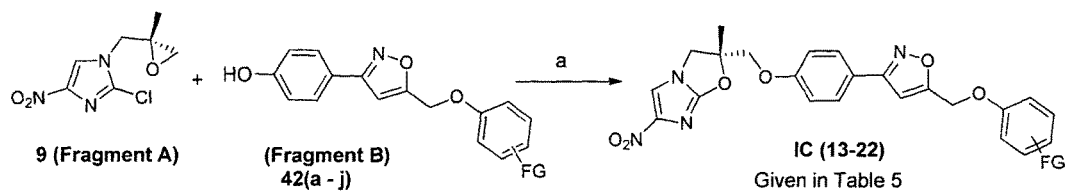
FIG. 20 shows the synthetic scheme (Scheme 17) for coupling of A (compound 9) with B [compound 42(a-j)] to generate the representing compounds of formula IC of general formula 1.

Table 5 shows the structure of representative compounds IC1-IC22 belonging to formula IC and synthesized as per scheme 15 and scheme 17 provided in FIG. 18 and FIG. 20, respectively.

Figure 22:
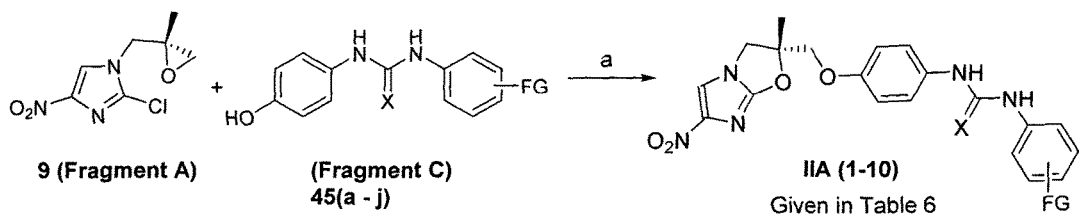
FIG. 22 shows the synthetic scheme (Scheme 19) for coupling of A (compound 9) with C [compound 45(a-j)] to generate the representing compounds of formula IIA of general formula 1.

Table 6 shows the structure of representative compounds IIA1-IIA10 belonging to formula IIA and synthesized as per scheme 19 provided in FIG. 22.

Figure 24:
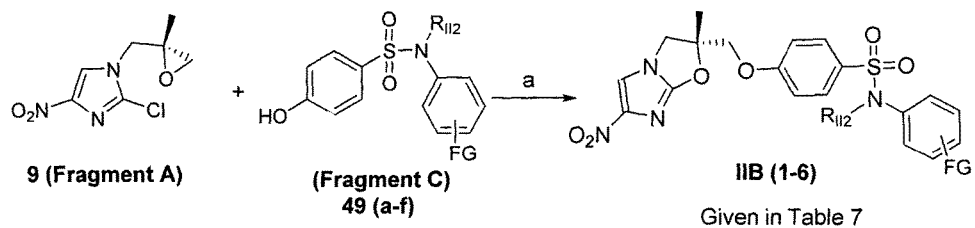
FIG. 24 shows the synthetic scheme (Scheme 21) for coupling of A (compound 9) with C [compound 49(a-f)] to generate the representing compounds of formula IIB of general formula 1.

Table 7 shows the structure of representative compounds IIB1-IIB6 belonging to formula JIB and synthesized as per scheme 21 provided in FIG. 24.

Figure 26:
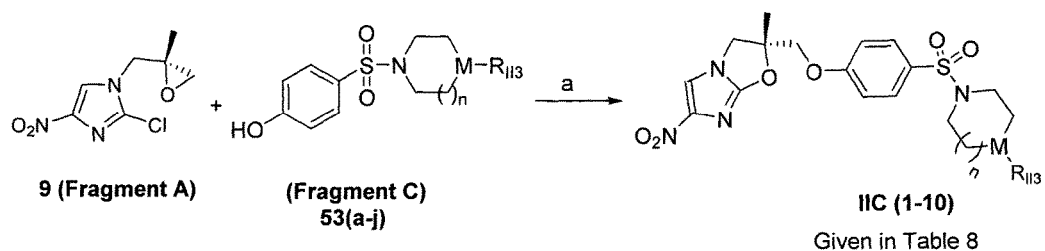
FIG. 26 shows the synthetic scheme (Scheme 23) for coupling of A (compound 9) with C [compound 53(a-j)] to generate the representing compounds of formula IIC of general formula 1.

Table 8 shows the structure of representative compounds IIC1-IIC10 belonging to formula IIC and synthesized as per scheme 23 provided in FIG. 26.

Table 9 shows the physico-chemical properties, anti-tuberculosis activity and cytotoxicity of representative compound shown in tables 1 to 8.

Table 10 shows the combination studies results of OPC-67683 and selected compounds of general formula 1 (IA25 and IIA3) with rifampicine, INH and ethambutol against *M. tuberculosis* H37Rv.

Table 11 shows the In vivo pharmacokinetic properties of OPC-67683, and selected compounds of general formula 1 (IA25, IA33, IC13 and IC14).

ABBREVIATION USED

H.R.: Heterocyclic Ring

DETAILED DESCRIPTION OF THE INVENTION

The present invention relates to new generation of triazoles, tetrazoles, isoxazoles, urea and sulphonamide functionalities containing 6-nitro-2,3-dihydronitroimidazooxazoles agents, their method of preparation, and their use as drugs for treatment of tuberculosis either alone or in combination with other anti-tubercular agents.

The present invention describes a compound having a general formula 1

General formula 1

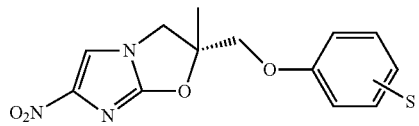

wherein substituent 'S' is selected from the group consisting of formula Ia, Ib, Ic, IIa, IIb and IIc;

Ia
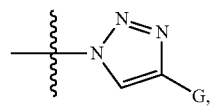

Ib
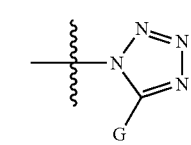

Ic
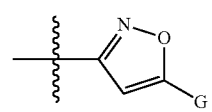

IIa
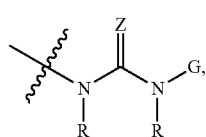

IIb
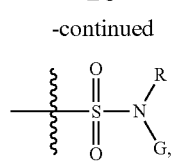

IIc
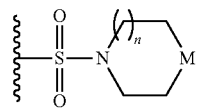

wherein,

'G' is selected from the group consisting of H, CH$_2$OR$_1$, OR$_1$ and R$_1$;

'Z' is selected from the group consisting of O, S and NR$_2$;

'n' is any number from 0 to 2;

'M' is selected from the group consisting of O, S, NR$_2$ and CR$_3$R$_4$;

R, R$_1$ and R$_2$ are each independently selected from the group consisting of H, alkyl, substituted alkyl, aryl, substituted aryl, phenyl, substituted phenyl, heterocyclic and substituted heterocyclic group selected from the group consisting of pyridyl, triazolyl, triazinyl, pyrimidinyl, pyridazinyl, oxazolyl, furanyl, benzofuranyl, thiophenyl, pyrrolyl, imidazoyl, thiazoyl, quinolinyl, isoquinolinyl, benzooxazolyl and benzothiazolyl;

R$_3$ and R$_4$ are each independently selected from the group consisting of H, alkyl, substituted alkyl, alkoxyl, substituted alkoxyl, phenyl, substituted phenyl, phenoxyl, substituted phenoxyl, heterocyclic and substituted heterocyclic group selected from the group consisting of pyridyl, triazolyl, triazinyl, pyrimidinyl, pyridazinyl, oxazolyl, furanyl, thiophenyl, pyrrolyl, imidazoyl and thiazoyl.

The compound of general formula 1 is selected from the group consisting of compound of formula I and formula II, I
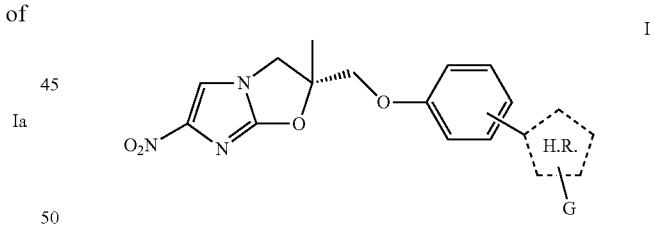

II
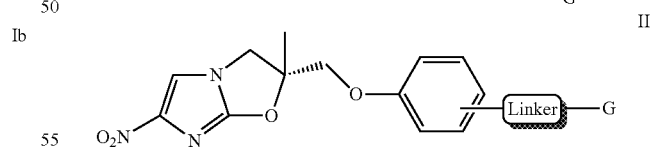

wherein

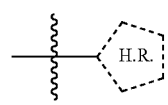

is selected from the group consisting of formula Ia, Ib and Ic;

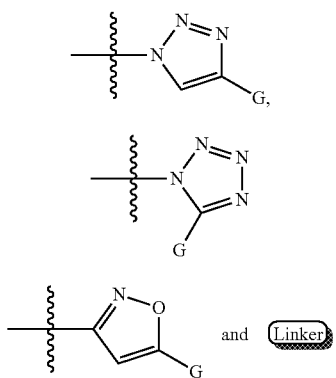

is selected from the group consisting of formula IIa, IIb and IIc;

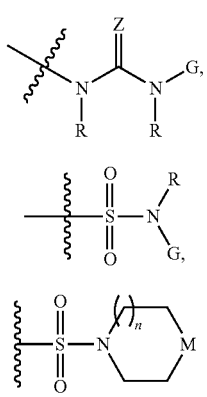

wherein,
- 'G' is selected from the group consisting of H, $CH_2OR_1$, $OR_1$ and $R_1$;
- 'Z' is selected from the group consisting of O, S and $NR_2$;
- 'n' is any number from 0 to 2; and
- 'M' is selected from the group consisting of O, S, $NR_2$ and $CR_3R_4$;
- R, $R_1$ and $R_2$ are each independently selected from the group consisting of H, alkyl, substituted alkyl, aryl, substituted aryl, phenyl, substituted phenyl, heterocyclic and substituted heterocyclic group selected from the group consisting of pyridyl, triazolyl, triazinyl, pyrimidinyl, pyridazinyl, oxazolyl, furanyl, benzofuranyl, thiophenyl, pyrrolyl, imidazoyl, thiazoyl, quinolinyl, isoquinolinyl, benzooxazolyl and benzothiazolyl;
- $R_3$ and $R_4$ are each independently selected from the group consisting of H, alkyl, substituted alkyl, alkoxyl, substituted alkoxyl, phenyl, substituted phenyl, phenoxyl, substituted phenoxyl, heterocyclic and substituted heterocyclic group selected from the group consisting of pyridyl, triazolyl, triazinyl, pyrimidinyl, pyridazinyl, oxazolyl, furanyl, thiophenyl, pyrrolyl, imidazoyl and thiazoyl.

In another aspect of the present invention, a preferred subclass of compound of general formula 1 is selected from the group consisting of compound of formula IA, IB and IC;

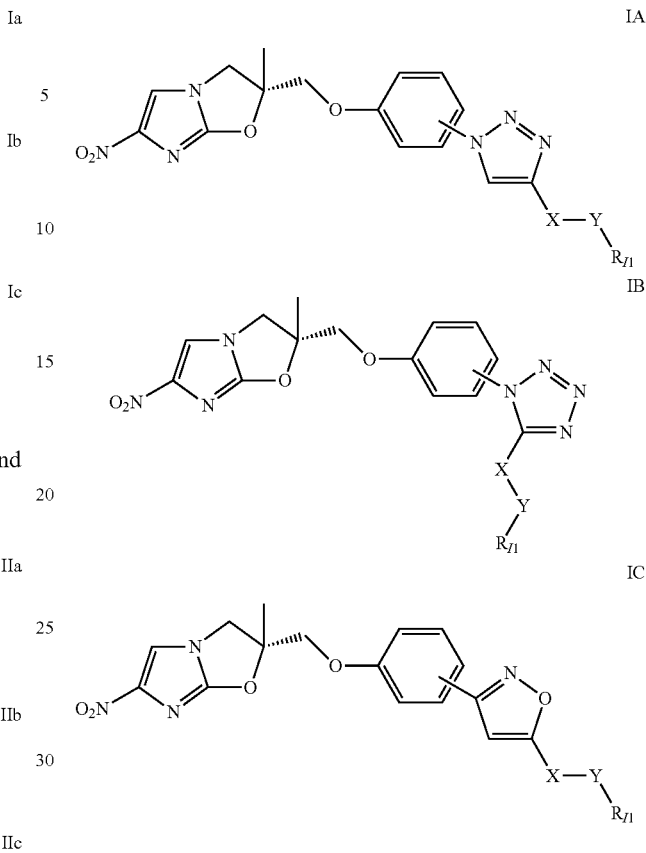

wherein
- 'X' is $CH_2$ or a direct bond;
- 'Y' is selected from the group consisting of O, S and $NR_{J2}$, or a direct bond;
- $R_{J1}$ is selected from the group consisting of H, alkyl, aryl, substituted alkyl, substituted aryl, heterocyclic, substituted hetercocyclic group selected from the group consisting of pyridyl, triazolyl, triazinyl, pyrimidinyl, pyridazinyl, oxazolyl, furanyl, benzofuranyl, thiophenyl, pyrrolyl, imidazoyl, thiazoyl, quinolinyl, isoquinolinyl, benzooxazolyl and benzothiazolyl; and substituted aryl is selected from the group consisting of F, Cl, Br, I, $NR_{J3}R_{J4}$, $CF_3$, $OCF_3$, $OR_{J5}$, $NO_2$, $CHR_{J6}R_{J7}$, alkyl group having C1 to C14, $COOR_{J8}$, CHO and $COR_{J9}$;
- $R_{J2}$, $R_{J3}$, $R_{J4}$, $R_{J5}$, $R_{J8}$ and $R_{J9}$ are each independently selected from the group consisting of H, alkyl, alkoxyl, substituted alkoxyl, phenyl, substituted phenyl, phenoxyl, substituted phenoxyl, heterocyclic and substituted heterocyclic group selected from the group consisting of pyridyl, triazolyl, triazinyl, pyrimidinyl, pyridazinyl, oxazolyl, furanyl, thiophenyl, pyrrolyl, imidazoyl and thiazoyl;
- $R_{J6}$ and $R_{J7}$ are each independently selected from the group consisting of H, alkyl, phenyl, substituted phenyl, heterocyclic and substituted heterocyclic group selected from the group consisting of pyridyl, triazolyl, triazinyl, pyrimidinyl, pyridazinyl, oxazolyl, furanyl, thiophenyl, pyrrolyl, imidazoyl and thiazoyl.

In another aspect of the present invention, another preferred subclass of compound of general formula 1 is selected from the group consisting of compound of formula IIA, IIB and IIC;

IIA

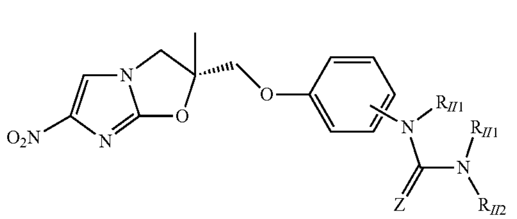

IIB

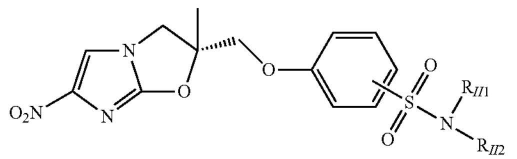

IIC

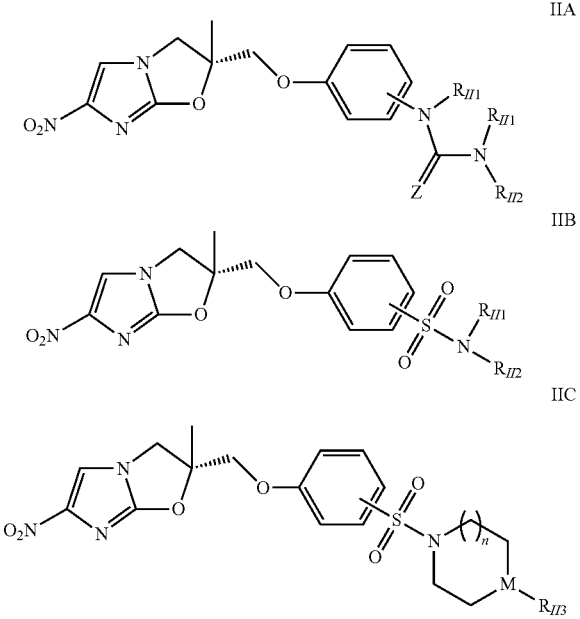

wherein

'Z' is selected from the group consisting of O, S and $NR_{II4}$;

'n' is any number from 0 to 2; and
'M' is selected from the group consisting of O, S, CH and N;

$R_{II1}$, $R_{II2}$, $R_{II3}$ and $R_{II4}$ are each independently selected from the group consisting of H, alkyl, aryl, substituted alkyl, substituted aryl, heterocyclic and substituted heterocyclic group selected from the group consisting of pyridyl, triazolyl, triazinyl, pyrimidinyl, pyridazinyl, oxazolyl, furanyl, benzofuranyl, thiophenyl, pyrrolyl, imidazoyl, thiazoyl, quinolinyl, isoquinolinyl, benzooxazolyl and benzothiazolyl; and substituted aryl is selected from the group consisting of F, Cl, Br, I, $NR_{II5}R_{II6}$, $CF_3$, $OCF_3$, $OR_{II7}$, $NO_2$, $CHR_{II8}R_{II9}$, alkyl group having C1 to C14, $COOR_{II10}$, CHO, and $COR_{II11}$;

$R_{II5}$, $R_{II6}$, $R_{II7}$, $R_{II10}$ and $R_{II11}$ are each independently selected from the group consisting of H, alkyl, phenyl, substituted phenyl, heterocyclic and substituted heterocyclic group selected from the group consisting of pyridyl, triazolyl, triazinyl, pyrimidinyl, pyridazinyl, oxazolyl, furanyl, thiophenyl, pyrrolyl, imidazoyl and thiazoyl;

$R_{II8}$ and $R_{II9}$ are each independently selected from the group consisting of H, alkyl, alkoxy, substituted alkoxy, phenyl, substituted phenyl, phenoxy, substituted phenoxy, heterocyclic and substituted heterocyclic group selected from the group consisting of pyridyl, triazolyl, triazinyl, pyrimidinyl, pyridazinyl, oxazolyl, furanyl, thiophenyl, pyrrolyl, imidazoyl and thiazoyl.

The compound of general formula 1 is useful in treatment of tuberculosis.

The compound of general formula 1 exhibits potent minimum inhibitory concentration (MIC) against H37Rv *Mycobacterium tuberculosis*, MDR-TB (resistant to isoniazid and rifampicin) in the range of 0.06 to 32 μg/ml.

The compound of general formula 1 exhibits MIC against XDR *Mycobacterium tuberculosis* (resistant to isoniazid, rifampicin, amikacin and moxifloxacin) in the range of 0.12 to 32 μg/ml.

The compound of general formula 1 does not exhibit any cytotoxicity up to 40 μg/ml in macrophage J774 cells line and exhibits safety index more than 10.

The compound of general formula 1, wherein one of the representing compound exhibits promising and better pharmacokinetic properties in mouse model with $C_{max}$ of 1 to 5 μg/ml and $AUC_{0-24}$ of 10 to 50 μg*hr/ml at an oral dose of 5 mg/kg.

The compounds of general formula 1 exhibit synergistic and additive effects with other known anti-tubercular drugs such as rafamicin, isoniazid and ethambutol in combination studies.

The compound of formula IA of general formula 1 is prepared by reacting an epoxide (compound 9) with a substituted phenol selected from the group consisting of compounds of formula 13(a-p), 16(a-d), 19(a-d), 23(a-h), 24(a-f) and 25 (a-d) in an organic solvent selected from the group consisting of N,N-dimethylformamide, DCM, acetonitrile, THF and acetone in presence of a base selected from the group consisting of cesium carbonate, potassium carbonate, potassium bicarbonate and sodium hydride at a temperature in the range of −20° C. to 10° C. and stirring for 1 to 24 hrs at a temperature in the range of 50° C. to 80° C.

The compound of formula IB of general formula 1 is prepared by reacting the epoxide (compound 9) with a substituted phenol selected from the group consisting of compounds of formula 30(a-f) and 36(a-d) in an organic solvent selected from the group consisting of DCM, acetonitrile, THF, acetoneand N, N-dimethylformamide in presence of a base selected from the group consisting of cesium carbonate, potassium carbonate, potassium bicarbonate and sodium hydride at a temperature in the range of −20° C. to 10° C. and stirring for 1 to 24 hrs at a temperature in the range of 50° C. to 80° C.

The compound of formula IC of general formula 1 is prepared by reacting an epoxide (compound 9) with a substituted phenol selected from the group consisting of compounds of formula 41(a-l) and 42(a-j) in an organic solvent selected from the group consisting of DCM, acetonitrile, THF, acetone and N, N-dimethylformamide in presence of a base selected from the group consisting of cesium carbonate, potassium carbonate, potassium bicarbonate and sodium hydride at a temperature in the range of −20° C. to 10° C. and stirring for 1 to 24 hrs at a temperature in the range of 50° C. to 80° C.

The compound of formula IIA of general formula 1 is prepared by reacting an epoxide (compound 9) with a substituted phenol selected from the group consisting of compounds of formula 45(a-j) in an organic solvent selected from the group consisting of DCM, acetonitrile, THF, acetone and N,N-dimethylformamide in presence of a base selected from the group consisting of cesium carbonate, potassium carbonate, potassium bicarbonate and sodium hydride at a temperature in the range of −20° C. to 10° C. and stirring for 1 to 24 hrs at a temperature in the range of 50° C. to 80° C.

The compound of formula IIB of general formula 1 is prepared by reacting an epoxide (compound 9) with a substituted phenol selected from the group consisting of compounds of formula 49(a-f) in an organic solvent selected from the group consisting of DCM, acetonitrile, THF, acetone and N,N-dimethylformamide in presence of a base selected from the group consisting of cesium carbonate, potassium carbonate, potassium bicarbonate and sodium hydride at a temperature in the range of −20° C. to 10° C. and stirring for 1 to 24 hrs at a temperature in the range of 50° C. to 80° C.

The compound of formula IIC of general formula 1 is prepared by reacting an epoxide (compound 9) with a substituted phenol selected from the group consisting of compounds of formula 53(a-j) in an organic solvent selected from the group consisting of DCM, acetonitrile, THF, acetone and N,N-dimethylformamide in presence of a base selected from the group consisting of cesium carbonate, potassium carbonate, potassium bicarbonate and sodium hydride at a temperature in the range of −20° C. to 10° C. and stirring for 1 to 24 hrs at a temperature in the range of 50° C. to 80° C.

The compounds of the present invention, combination thereof, isomers, and physiologically functionally salt derivatives are useful for treatment of *Mycobacterium tuberculosis* infection.

In the present invention, the pharmaceutically acceptable salts are salts of an acid selected from the group consisting of hydrochloric acid, sulfuric acid, phosphoric acid, acetic acid, citric acid, oxalic acid, malonic acid, salicylic acid, malic acid, fumaric acid, succinic acid, ascorbic acid, maleic acid, methanesulfonic acid and isoethonic acid or salts of a base selected from the group consisting of potassium carbonate, sodium hydroxide, potassium hydroxide, ammonia, triethylamine and triethanolamine.

The most preferred compounds of formula I and II of general formula 1 are:

(R)-2-{4-(4-phenyl-1H-1,2,3-triazol-1-yl)phenoxy)methyl}-2,3-dihydro-2-methyl-6-nitroimidazo[2,1-b]oxazole (compound IA1), (R)-2-{4-[4-(4-ethylphenyl)-1H-1,2,3-triazol-1-yl]phenoxymethyl}-2,3-dihydro-2-methyl-6-nitroimidazo[2,1-b]oxazole (compound IA2), (R)-2-{4-[4-(4-fluorophenyl)-1H-1,2,3-triazol-1-yl]phenoxymethyl}-2,3-dihydro-2-methyl-6-nitroimidazo[2,1-b]oxazole (compound IA3), (R)-2-{4-[4-(2-fluorophenyl)-1H-1,2,3-triazol-1-yl]phenoxymethyl}-2,3-dihydro-2-methyl-6-nitroimidazo[2,1-b]oxazole (compound IA4), (R)-2-{4-[4-(4-trifluoromethoxyphenyl)-1H-1,2,3-triazol-1-yl]phenoxymethyl}-2,3-dihydro-2-methyl-6-nitroimidazo[2,1-b]oxazole (compound IA5), (R)-2-{4-[4-(2-trifluoromethylphenyl)-1H-1,2,3-triazol-1-yl]phenoxymethyl}-2,3-dihydro-2-methyl-6-nitroimidazo[2,1-b]oxazole (compound IA6), (R)-2-{4-[4-(2,4-difluorophenyl)-1H-1,2,3-triazol-1-yl]phenoxymethyl}-2,3-dihydro-2-methyl-6-nitroimidazo[2,1-b]oxazole (compound IA7), (R)-2-{4-[4-(4-methylphenyl)-1H-1,2,3-triazol-1-yl]phenoxymethyl}-2,3-dihydro-2-methyl-6-nitroimidazo[2,1-b]oxazole (compound IA8), (R)-2-{4-[4-(4-isopropylphenyl)-1H-1,2,3-triazol-1-yl]phenoxymethyl}-2,3-dihydro-2-methyl-6-nitroimidazo[2,1-b]oxazole (compound IA9), (R)-2-{4-[4-(3-fluorophenyl)-1H-1,2,3-triazol-1-yl]phenoxymethyl}-2,3-dihydro-2-methyl-6-nitroimidazo[2,1-b]oxazole (compound IA10), (R)-2-{4-[4-(4-methoxyphenyl)-1H-1,2,3-triazol-1-yl]phenoxymethyl}-2,3-dihydro-2-methyl-6-nitroimidazo[2,1-b]oxazole (compound IA11), (R)-2-{4-[4-(3-trifluoromethoxyphenyl)-1H-1,2,3-triazol-1-yl]phenoxymethyl}-2,3-dihydro-2-methyl-6-nitroimidazo[2,1-b]oxazole (compound IA12), (R)-2-{4-[4-(3-trifluoromethylphenyl)-1H-1,2,3-triazol-1-yl]phenoxymethyl}-2,3-dihydro-2-methyl-6-nitroimidazo[2,1-b]oxazole (compound IA13), (R)-2-{4-[4-(4-pyridin-2-yl)-1H-1,2,3-triazol-1-yl]phenoxymethyl}-2,3-dihydro-2-methyl-6-nitroimidazo[2,1-b]oxazole (compound IA14), (R)-2-{4-[4-pentyl-1H-1,2,3-triazol-1-yl]phenoxymethyl}-2,3-dihydro-2-methyl-6-nitroimidazo[2,1-b]oxazole (compound IA15), (R)-2-{4-[4-heptyl-1H-1,2,3-triazol-1-yl]phenoxymethyl}-2,3-dihydro-2-methyl-6-nitroimidazo[2,1-b]oxazole (compound IA16), (R)-2-{3-[4-(4-fluorophenyl)-1H-1,2,3-triazol-1-yl]phenoxymethyl}-2,3-dihydro-2-methyl-6-nitroimidazo[2,1-b]oxazole (compound IA17), (R)-2-{3-[4-(4-trifluoromethylphenyl)-1H-1,2,3-triazol-1-yl]phenoxymethyl}-2,3-dihydro-2-methyl-6-nitroimidazo[2,1-b]oxazole (compound IA18), (R)-2-{3-[4-(4-trifluoromethoxyphenyl)-1H-1,2,3-triazol-1-yl]phenoxymethyl}-2,3-dihydro-2-methyl-6-nitroimidazo[2,1-b]oxazole (compound IA19), (R)-2-{3-[4-(2,4-difluorophenyl)-1H-1,2,3-triazol-1-yl]phenoxymethyl}-2,3-dihydro-2-methyl-6-nitroimidazo[2,1-b]oxazole (compound IA20), (R)-2-{2-[4-(4-fluorophenyl)-1H-1,2,3-triazol-1-yl]phenoxymethyl}-2,3-dihydro-2-methyl-6-nitroimidazo[2,1-b]oxazole (compound IA21), (R)-2-{2-[4-(4-trifluoromethylphenyl)-1H-1,2,3-triazol-1-yl]phenoxymethyl}-2,3-dihydro-2-methyl-6-nitroimidazo[2,1-b]oxazole (compound IA22), (R)-2-{2-[4-(4-trifluoromethoxyphenyl)-1H-1,2,3-triazol-1-yl]phenoxymethyl}-2,3-dihydro-2-methyl-6-nitroimidazo[2,1-b]oxazole (compound IA23), (R)-2-{2-[4-(2,4-difluorophenyl)-1H-1,2,3-triazol-1-yl]phenoxymethyl}-2,3-dihydro-2-methyl-6-nitroimidazo[2,1-b]oxazole (compound IA24), (R)-2-{4-[4-(4-trifluoromethoxyphenoxy)methyl)-1H-1,2,3-triazol-1-yl]phenoxymethyl}-2,3-dihydro-2-methyl-6-nitroimidazo[2,1-b]oxazole (compound IA25), (R)-2-{4-[4-(4-fluorophenoxy)methyl)-1H-1,2,3-triazol-1-yl]phenoxymethyl}-2,3-dihydro-2-methyl-6-nitroimidazo[2,1-b]oxazole (compound IA26), (R)-2-{4-[4-(4-trifluoromethylphenoxy)methyl)-1H-1,2,3-triazol-1-yl]phenoxymethyl}-2,3-dihydro-2-methyl-6-nitroimidazo[2,1-b]oxazole (compound IA27), (R)-2-{4-[4-(2-fluorophenoxy)methyl)-1H-1,2,3-triazol-1-yl]phenoxymethyl}-2,3-dihydro-2-methyl-6-nitroimidazo[2,1-b]oxazole (compound IA28), (R)-2-{4-[4-(4-methylphenoxy)methyl)-1H-1,2,3-triazol-1-yl]phenoxymethyl}-2,3-dihydro-2-methyl-6-nitroimidazo[2,1-b]oxazole (compound IA29), (R)-2-{4-[4-(4-isopropylphenoxy)methyl)-1H-1,2,3-triazol-1-yl]phenoxymethyl}-2,3-dihydro-2-methyl-6-nitroimidazo[2,1-b]oxazole (compound IA30), (R)-2-{4-[4-(4-ethylphenoxy)methyl)-1H-1,2,3-triazol-1-yl]phenoxymethyl}-2,3-dihydro-2-methyl-6-nitroimidazo[2,1-b]oxazole (compound IA31), (R)-2-{4-[4-(4-sec-butylphenoxy)methyl)-1H-1,2,3-triazol-1-yl]phenoxymethyl}-2,3-dihydro-2-methyl-6-nitroimidazo[2,1-b]oxazole (compound IA32), (R)-2-{3-[4-(4-trifluoromethoxyphenoxy)methyl)-1H-1,2,3-triazol-1-yl]phenoxymethyl}-2,3-dihydro-2-methyl-6-nitroimidazo[2,1-b]oxazole (compound IA33), (R)-2-{3-[4-(4-fluorophenoxy)methyl)-1H-1,2,3-triazol-1-yl]phenoxymethyl}-2,3-dihydro-2-methyl-6-nitroimidazo[2,1-b]oxazole (compound IA34), (R)-2-{3-[4-(4-trifluoromethylphenoxy)methyl)-1H-1,2,3-triazol-1-yl]phenoxymethyl}-2,3-dihydro-2-methyl-6-nitroimidazo[2,1-b]oxazole (compound IA35), (R)-2-{3-[4-(2-fluorophenoxy)methyl)-1H-1,2,3-triazol-1-yl]phenoxymethyl}-2,3-dihydro-2-methyl-6-nitroimidazo[2,1-b]oxazole (compound IA36),
(R)-2-{3-[4-(4-methylphenoxy)methyl)-1H-1,2,3-triazol-1-yl]phenoxymethyl}-2,3-dihydro-2-methyl-6-nitroimidazo[2,1-b]oxazole (compound IA37),
(R)-2-{3-[4-(4-isopropylphenoxy)methyl)-1H-1,2,3-triazol-1-yl]phenoxymethyl}-2,3-dihydro-2-methyl-6-nitroimidazo[2,1-b]oxazole (compound IA38),
(R)-2-{2-[4-(4-trifluoromethoxyphenoxy)methyl)-1H-1,2,3-triazol-1-yl]phenoxymethyl}-2,3-dihydro-2-methyl-6-nitroimidazo[2,1-b]oxazole (compound IA39),
(R)-2-{2-[4-(4-fluorophenoxy)methyl)-1H-1,2,3-triazol-1-yl]phenoxymethyl}-2,3-dihydro-2-methyl-6-nitroirnidazo[2,1-b]oxazole (compound IA40),
(R)-2-{2-[4-(4-trifluoromethylphenoxy)methyl)-1H-1,2,3-triazol-1-yl]phenoxymethyl}-2,3-dihydro-2-methyl-6-nitroimidazo[2,1-b]oxazole (compound IA41),
(R)-2-{2-[4-(2-fluorophenoxy)methyl)-1H-1,2,3-triazol-1-yl]phenoxymethyl}-2,3-dihydro-2-methyl-6-nitroimidazo[2,1-b]oxazole (compound IA42),
(R)-2-{4-[5-phenyl-1H-tetrazol-1-yl]phenoxymethyl}-2,3-dihydro-2-methyl-6-nitroimidazo[2,1-b]oxazole (compound IB1),
(R)-2-{4-[5-(4-trifluoromethoxyphenyl)-1H-tetrazol-1-yl]phenoxymethyl}-2,3-dihydro-2-methyl-6-nitroimidazo[2,1-b]oxazole (compound IB2),
(R)-2-{4-[5-(4-methylphenyl)-1H-tetrazol-1-yl]phenoxymethyl}-2,3-dihydro-2-methyl-6-nitroimidazo[2,1-b]oxazole (compound IB3),
(R)-2-{4-[5-(4-fluorophenyl)-1H-tetrazol-1-yl]phenoxymethyl}-2,3-dihydro-2-methyl-6-nitroimidazo[2,1-b]oxazole (compound IB4),
(R)-2-{4-[5-(4-trifluoromethylphenyl)-1H-tetrazol-1-yl]phenoxymethyl}-2,3-dihydro-2-methyl-6-nitroimidazo[2,1-b]oxazole (compound IB5),
(R)-2-{4-[5-(4-ethylphenyl)-1H-tetrazol-1-yl]phenoxymethyl}-2,3-dihydro-2-methyl-6-nitroimidazo[2,1-b]oxazole (compound IB6),
(R)-2-{4-[5-(4-fluorophenoxy)-1H-tetrazol-1-yl]phenoxymethyl}-2,3-dihydro-2-methyl-6-nitroimidazo[2,1-b]oxazole (compound IB7),
(R)-2-{4-[5-(4-trifluoromethylphenoxy)-1H-tetrazol-1-yl]phenoxymethyl}-2,3-dihydro-2-methyl-6-nitroimidazo[2,1-b]oxazole (compound IB8),
(R)-2-{4-[5-(4-methylphenoxy)-1H-tetrazol-1-yl]phenoxymethyl}-2,3-dihydro-2-methyl-6-nitroimidazo[2,1-b]oxazole (compound IB9),
(R)-2-{4-[5-(4-trifluoromethoxyphenoxy)-1H-tetrazol-1-yl]phenoxymethyl}-2,3-dihydro-2-methyl-6-nitroimidazo[2,1-b]oxazole (compound IB10),
(R)-2-{4-[5-phenylisoxazol-3-yl]phenoxymethyl}-2,3-dihydro-2-methyl-6-nitroimidazo[2,1-b]oxazole (compound IC1),
(R)-2-{4-[5-(4-ethylphenyl)isoxazol-3-yl]phenoxymethyl}-2,3-dihydro-2-methyl-6-nitroimidazo[2,1-b]oxazole (compound IC2),
(R)-2-{4-[5-(2,4-di fluorophenyl)isoxazol-3-yl]phenoxymethyl}-2,3-dihydro-2-methyl-6-nitroimidazo[2,1-b]oxazole (compound IC3),
(R)-2-{4-[5-(2-fluorophenyl)isoxazol-3-yl]phenoxymethyl}-2,3-dihydro-2-methyl-6-nitroimidazo[2,1-b]oxazole (compound IC4),
(R)-2-{4-[5-(4-trifluoromethylphenyl)isoxazol-3-yl]phenoxymethyl}-2,3-dihydro-2-methyl-6-nitroimidazo[2,1-b]oxazole (compound IC5),
(R)-2-{4-[5-(4-methylphenyl)isoxazol-3-yl]phenoxymethyl}-2,3-dihydro-2-methyl-6-nitroimidazo[2,1-b]oxazole (compound IC6),
(R)-2-{4-[5-(4-methoxyphenyl)isoxazol-3-yl]phenoxymethyl}-2,3-dihydro-2-methyl-6-nitroimidazo[2,1-b]oxazole (compound IC7),
(R)-2-{4-[5-(3-fluorophenyl)isoxazol-3-yl]phenoxymethyl}-2,3-dihydro-2-methyl-6-nitroimidazo[2,1-b]oxazole (compound IC8),
(R)-2-{4-[5-(pyridin-2-yl)isoxazol-3-yl]phenoxymethyl}-2,3-dihydro-2-methyl-6-nitroimidazo[2,1-b]oxazole (compound IC9),
(R)-2-{4-[5-(4-trifluoromethoxyphenyl)isoxazol-3-yl]phenoxymethyl}-2,3-dihydro-2-methyl-6-nitroimidazo[2,1-b]oxazole (compound IC10),
(R)-2-{4-[5-pentylisoxazol-3-yl]phenoxymethyl}-2,3-dihydro-2-methyl-6-nitroimidazo[2,1-b]oxazole (compound IC11),
(R)-2-{4-[5-heptylisoxazol-3-yl]phenoxymethyl}-2,3-dihydro-2-methyl-6-nitroimidazo[2,1-b]oxazole (compound IC12),
(R)-2-{4-[5-(4-trifluoromethoxyphenoxymethyl)isoxazol-3-yl]phenoxymethyl}-2,3-dihydro-2-methyl-6-nitroimidazo[2,1-b]oxazole (compound IC13),
(R)-2-{4-[5-(4-fluorophenoxymethyl)isoxazol-3-yl]phenoxymethyl}-2,3-dihydro-2-methyl-6-nitroimidazo[2,1-b]oxazole (compound IC14),
(R)-2-{4-[5-(4-trifluoromethylphenoxymethyl)isoxazol-3-yl]phenoxymethyl}-2,3-dihydro-2-methyl-6-nitroimidazo[2,1-b]oxazole (compound IC15),
(R)-2-{4-[5-(2-fluorophenoxymethyl)isoxazol-3-yl]phenoxymethyl}-2,3-dihydro-2-methyl-6-nitroimidazo[2,1-b]oxazole (compound IC16),
(R)-2-{4-[5-(4-methylphenoxymethyl)isoxazol-3-yl]phenoxymethyl}-2,3-dihydro-2-methyl-6-nitroimidazo[2,1-b]oxazole (compound IC17),
(R)-2-{4-[5-(4-isopropylphenoxymethyl)isoxazol-3-yl]phenoxymethyl}-2,3-dihydro-2-methyl-6-nitroimidazo[2,1-b]oxazole (compound IC18),
(R)-2-{4-[5-(4-ethylphenoxymethyl)isoxazol-3-yl]phenoxymethyl}-2,3-dihydro-2-methyl-6-nitroimidazo[2,1-b]oxazole (compound IC19),
(R)-2-{4-[5-(4-sec-butylphenoxymethyl)isoxazol-3-yl]phenoxymethyl}-2,3-dihydro-2-methyl-6-nitroimidazo[2,1-b]oxazole (compound IC20),
(R)-2-{4-[5-(phenoxymethyl)isoxazol-3-yl]phenoxymethyl}-2,3-dihydro-2-methyl-6-nitroimidazo[2,1-b]oxazole (compound IC21),
(R)-2-{4-[5-(2,4-difluorophenoxymethyl)isoxazol-3-yl]phenoxymethyl}-2,3-dihydro-2-methyl-6-nitroimidazo[2,1-b]oxazole (compound IC22),
(R)-1-(4-fluorophenyl)-3-{4-(2-methyl-6-nitro-2,3-dihydroimidazo[2,1-b]oxazol-2-yl)methoxyphenyl}urea (compound IIA1),
(R)-1-(4-ethylphenyl)-3-{4-(2-methyl-6-nitro-2,3-dihydroimidazo[2,1-b]oxazol-2-yl)methoxyphenyl}urea (compound IIA2),
(R)-1-(4-trifluoromethylphenyl)-3-{4-(2-methyl-6-nitro-2,3-dihydroimidazo[2,1-b]oxazol-2-yl)methoxyphenyl}urea (compound IIA3),
(R)-1-(4-methylphenyl)-3-{4-(2-methyl-6-nitro-2,3-dihydroimidazo[2,1-b]oxazol-2-yl)methoxyphenyl}urea (compound IIA4),
(R)-1-(4-methoxyphenyl)-3-{4-(2-methyl-6-nitro-2,3-dihydroimidazo[2,1-b]oxazol-2-yl)methoxyphenyl}urea (compound IIA5), (R)-1-(4-trifluoromethoxyphenyl)-3-{4-(2-methyl-6-nitro-2,3-dihydroimidazo[2,1-b]oxazol-2-yl)methoxyphenyl}urea (compound IIA6), (R)-1-(4-methoxyphenyl)-3-{4-(2-methyl-6-nitro-2,3-dihydroimidazo[2,1-b]oxazol-2-yl)methoxyphenyl}thiourea (compound IIA7), (R)-1-(4-trifluoromethoxyphenyl)-3-{4-(2-methyl-6-nitro-2,3-dihydroimidazo[2,1-b]oxazol-2-yl)methoxyphenyl}thiourea (compound IIA8), (R)-1-(4-fluorophenyl)-3-{4-(2-methyl-6-nitro-2,3-dihydroimidazo[2,1-b]oxazol-2-yl)methoxyphenyl}thiourea (compound IIA9), (R)-1-(4-trifluoromethylphenyl)-3-{4-(2-methyl-6-nitro-2,3-dihydro imidazo[2,1-b]oxazol-2-yl)methoxyphenyl}thiourea (compound IIA10), (R)-4-{(2-methyl-6-nitro-2,3-dihydroimidazo[2,1-b]oxazol-2-yl)methoxy}-N-(p-tolyl)benzenesulfonamide (compound IIB1), (R)-4-{(2-methyl-6-nitro-2,3-dihydroimidazo[2,1-b]oxazol-2-yl)methoxy}-N-(p-trifluoromethoxyphenyl)benzenesulfonamide (compound IIB2), (R)-4-{(2-methyl-6-nitro-2,3-dihydroimidazo[2,1-b]oxazol-2-yl)methoxy}-N-(p-trifluoromethylphenyl)benzenesulfonamide (compound IIB3), (R)—N-methyl-4-{(2-methyl-6-nitro-2,3-dihydroimidazo[2,1-b]oxazol-2-yl)methoxy}-N-phenylbenzenesulfonamide (compound IIB4), (R)—N-methyl-4-{(2-methyl-6-nitro-2,3-dihydroimidazo[2,1-b]oxazol-2-yl)methoxy}-N-(p-tolyl)benzenesulfonamide (compound IIB5), (R)—N-methyl-4-{(2-methyl-6-nitro-2,3-dihydro imidazo[2,1-b]oxazol-2-yl)methoxy}-N-(p-trifluoromethylphenyl)benzenesulfonamide (compound IIB6), (R)-2-{4-(4-phenylpiperazin-1-yl)sulfonylphenoxymethyl}-2,3-dihydro-2-methyl-6-nitroimidazo[2,1-b]oxazole (compound IIC1), (R)-2-{4-[4-(4-fluorophenyl)piperazin-1-yl]sulfonylphenoxymethyl}-2,3-dihydro-2-methyl-6-nitroimidazo[2,1-b]oxazole (compound IIC2), (R)-2-{4-[4-(3-chlorophenyl)piperazin-1-yl]sulfonylphenoxymethyl}-2,3-dihydro-2-methyl-6-nitroimidazo[2,1-b]oxazole (compound IIC3), (R)-2-{4-[4-(4-trifluoromethoxyphenyl)piperazin-1-yl]sulfonylphenoxymethyl}-2,3-dihydro-2-methyl-6-nitroimidazo[2,1-b]oxazole (compound IIC4), (R)-ethyl-{4-[4-(2-methyl-6-nitro-2,3-dihydroimidazo[2,1-b]oxazol-2yl)methoxyphenyl]sulfonyl}piperazine-1-carboxylate (compound IIC5), (R)-{4-[4-(2-methyl-6-nitro-2,3-dihydroimidazo[2,1-b]oxazol-2yl)methoxyphenyl]sulfonyl}piperazine-1-yl(phenyl)methanone (compound IIC6), (R)-2-{4-(piperidin-1-ylsulfonyl)phenoxymethyl}-2,3-dihydro-2-methyl-6-nitroimidazo[2,1-b]oxazole (compound IIC7), (R)-2-{4-[(4-phenylpiperidin-1-yl)sulfonyl]phenoxymethyl}-2,3-dihydro-2-methyl-6-nitroimidazo[2,1-b]oxazole (compound IIC8), (R)-2-{4-(pyrrolidin-1-ylsulfonyl)phenoxymethyl}-2,3-dihydro-2-methyl-6-nitroimidazo[2,1-b]oxazole (compound IIC9) and (R)-2-{4-(morpholinsulfonyl)phenoxymethyl}-2,3-dihydro-2-methyl-6-nitroimidazo[2,1-b]oxazole (compound IIC10)

EXAMPLES

Synthesis of Compounds

The following examples are given by way of illustrating the present invention and should not be construed to limit the scope of the invention:

Example 1: Synthesis of Fragment A, an Epoxide (Compound 9)

Figure 1:
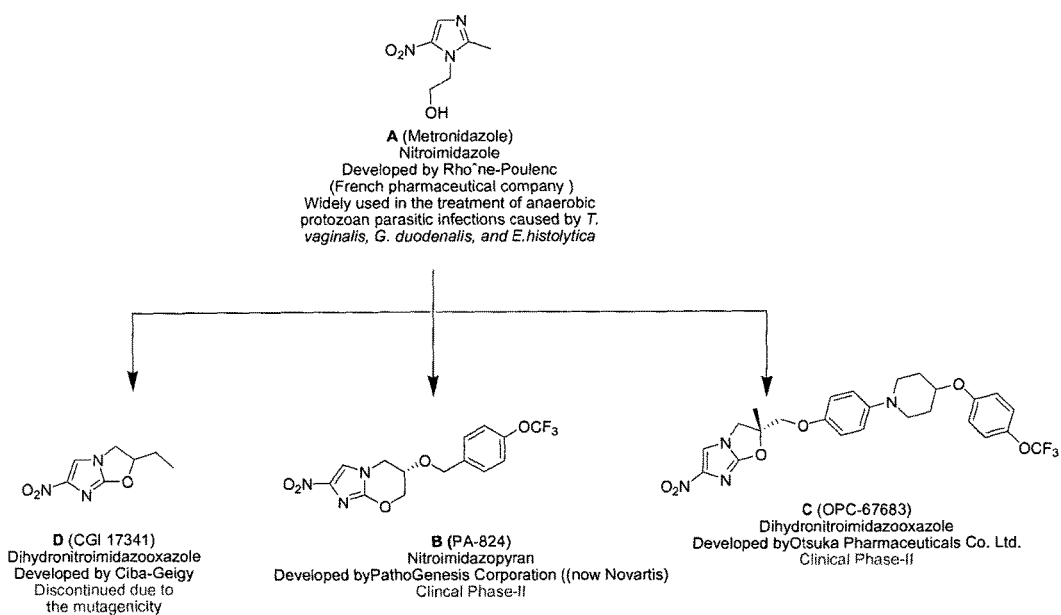
FIG. 1 shows the structure of anti-TB clinical candidates.
Figure 2:
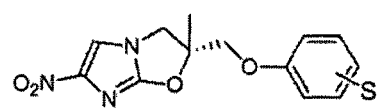
FIG. 2 shows the general structure of representative of compounds referred to in Table 1, 2, 3, 4, 5, 6, 7 and 8.
Figure 2:
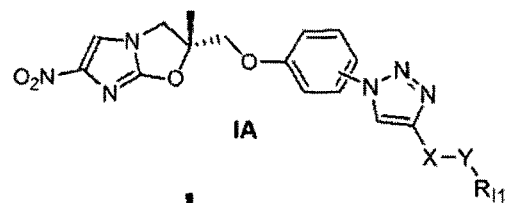
Figure 2:
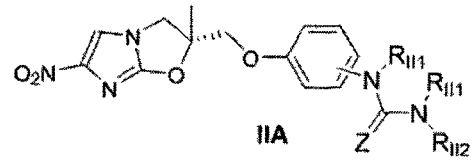
Figure 2:
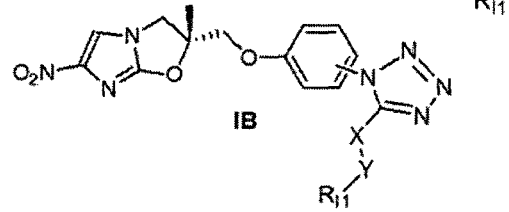
Figure 2:
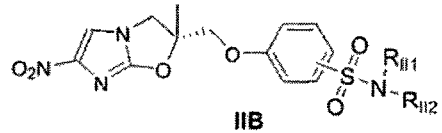
Figure 2:
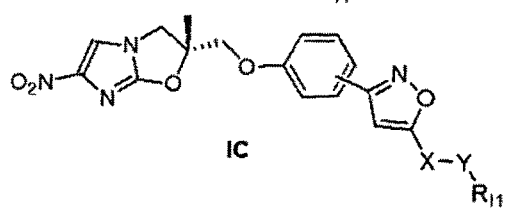
Figure 2:
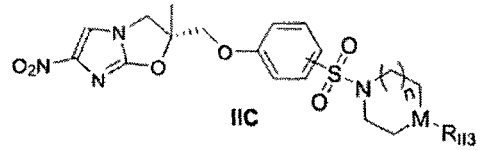
Figure 3:
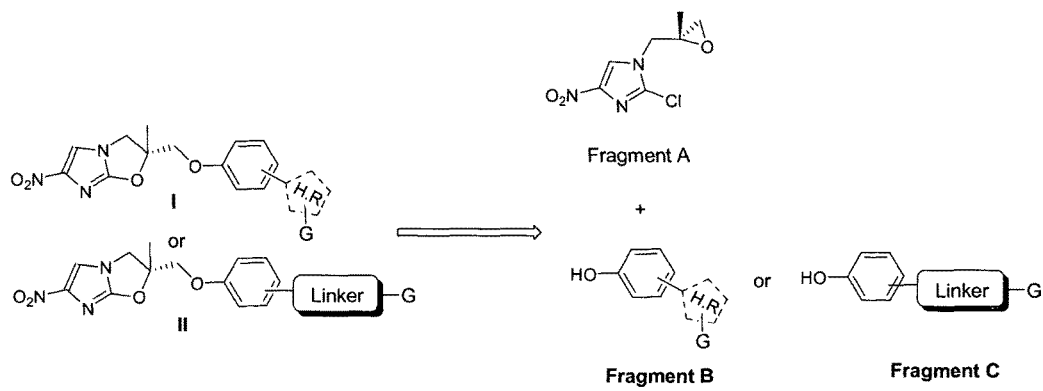
FIG. 3 shows the retro-synthetic approach for the synthesis of compounds of formula I and II of general formula 1.
Figure 4:
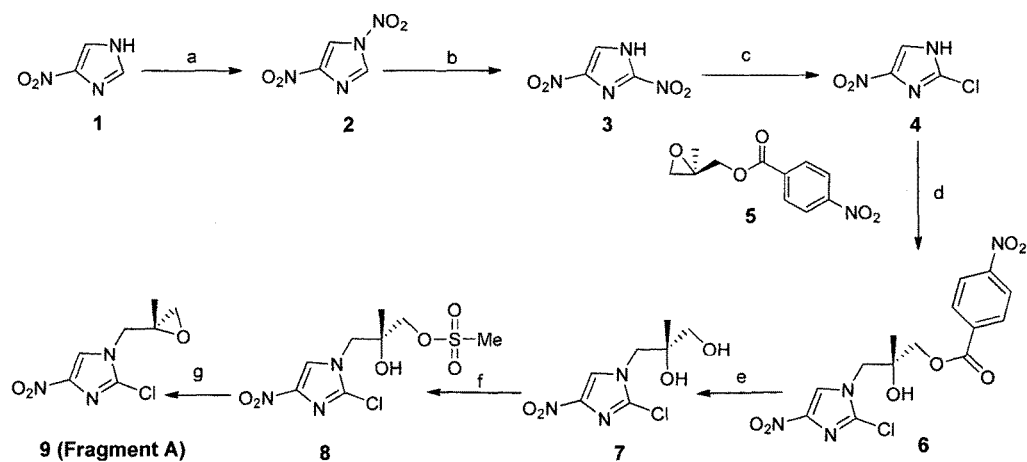
FIG. 4 shows the synthetic scheme (scheme 1) for the synthesis of fragment A (compound 9).

Fragment A (compound 9) was successfully synthesized from a starting material 4-nitroimidiazole 1 as shown in scheme 1 (provided in FIG. 4) by following the known procedure (Sasaki, H.; Haraguchi, Y.; Itotani, M.; Kuroda, H.; Hashizume, H.; Tomishige, T.; Kawasaki, M.; Matsumoto, M.; Komatsu, M.; Tsubouchi, H. *J. Med. Chem.* 2006, 49, 7854)

Example 2: Synthesis of Fragment B

Figure 5:
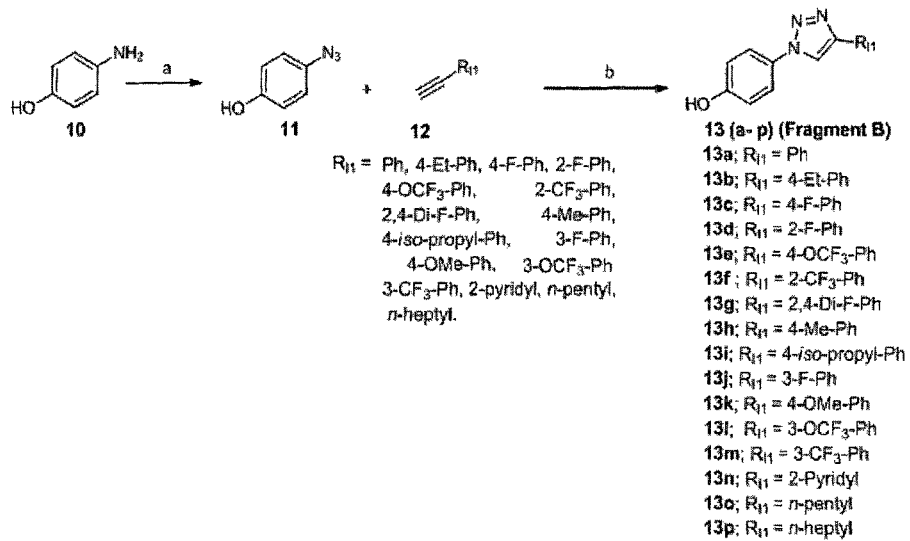
FIG. 5 shows the synthetic scheme (scheme 2) for the synthesis of fragment B [compounds 13(a-p)].
Figure 6:
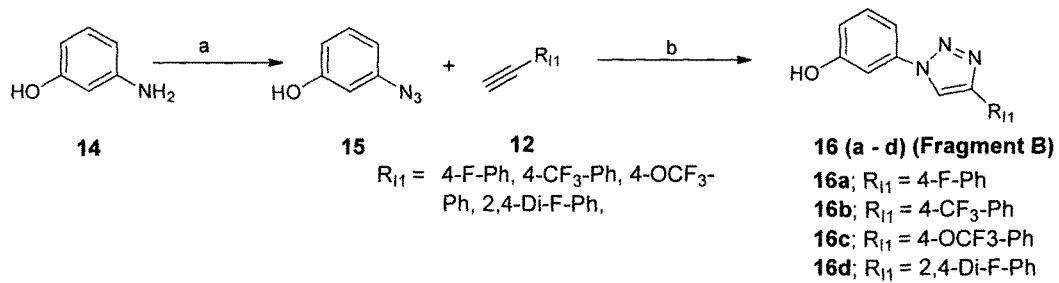
FIG. 6 shows the synthetic scheme (scheme 3) for the synthesis of fragment B [compounds 16(a-d)].
Figure 7:
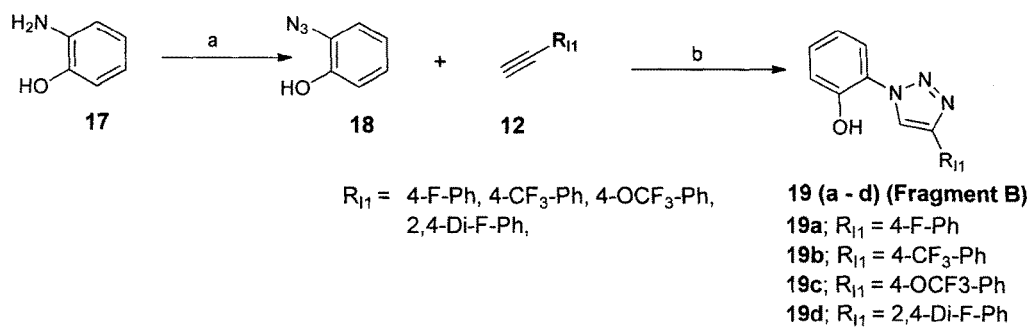
FIG. 7 shows the synthetic scheme (scheme 4) for the synthesis of fragment B [compounds 19(a-d)].
Figure 9:
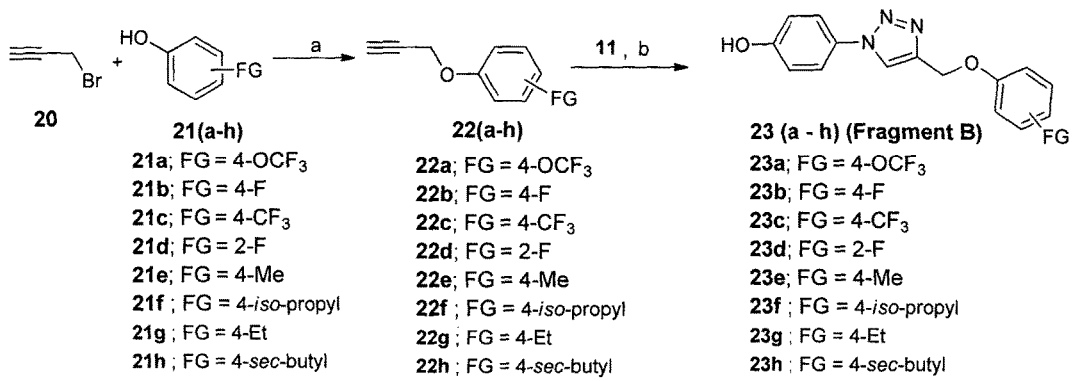
FIG. 9 shows the synthetic scheme (scheme 6) for the synthesis of fragment B [compounds 23(a-h)].
Figure 10:
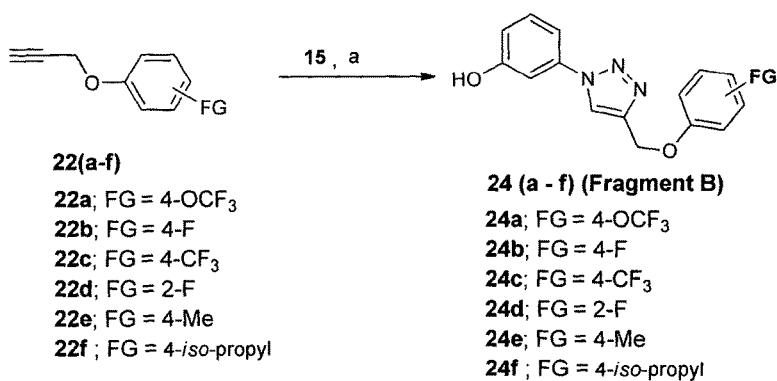
FIG. 10 shows the synthetic scheme (scheme 7) for the synthesis of fragment B [compounds 24(a-f)].
Figure 11:
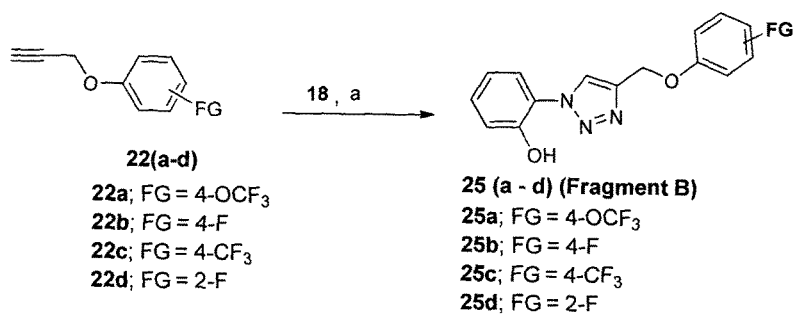
FIG. 11 shows the synthetic scheme (scheme 8) for the synthesis of fragment B [compounds 25(a-d)].
Figure 13:
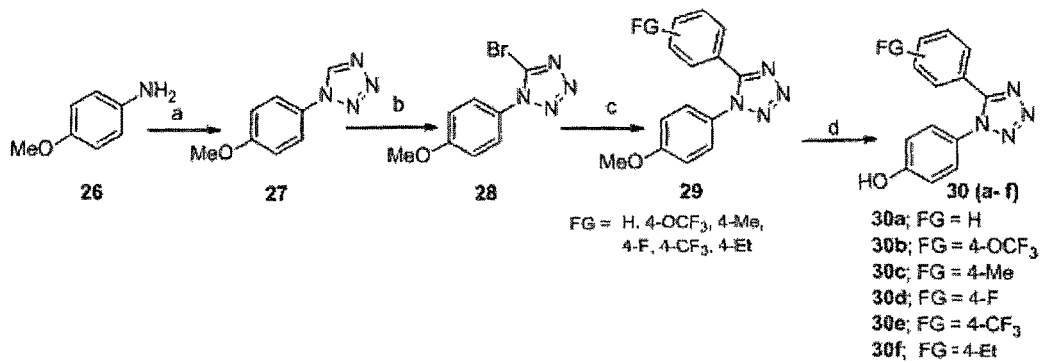
FIG. 13 shows the synthetic scheme (scheme 10) for the synthesis of fragment B [compounds 30(a-f)].
Figure 15:
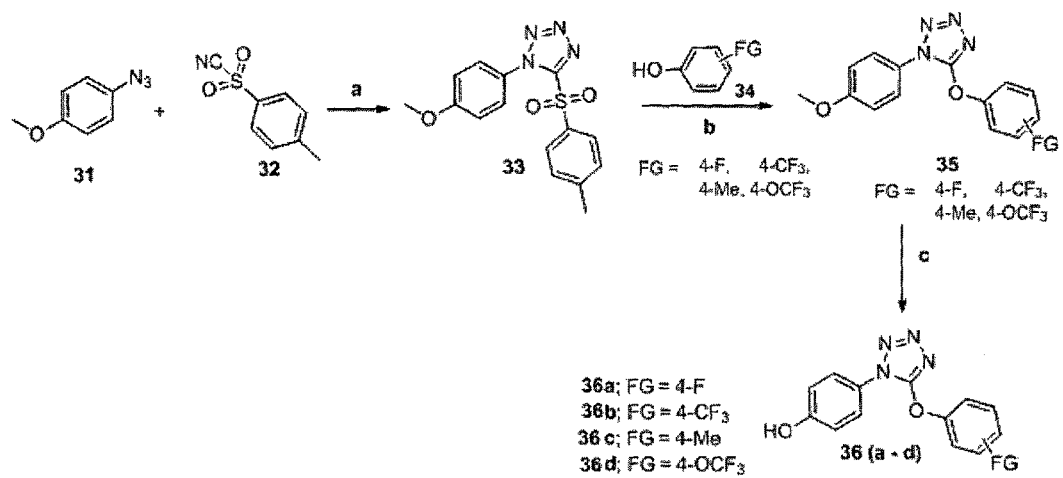
FIG. 15 shows the synthetic scheme (scheme 12) for the synthesis of fragment B [compounds 36(a-d)].
Figure 17:
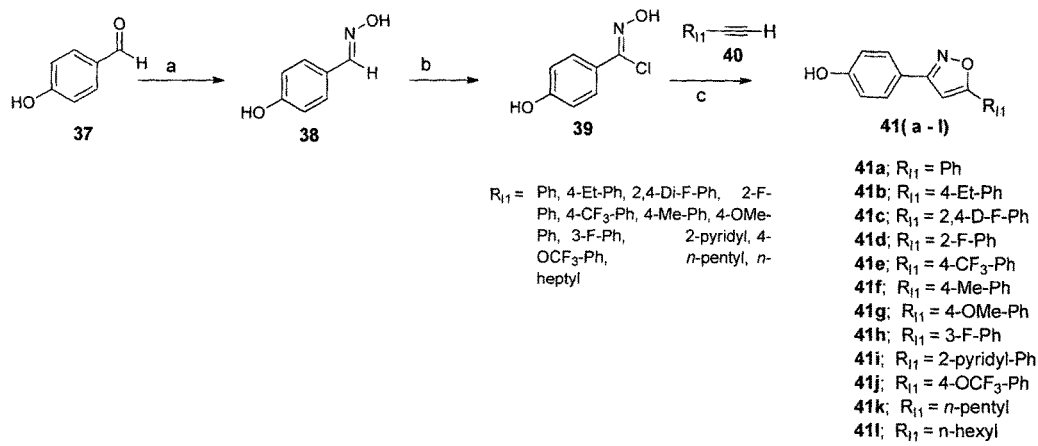
FIG. 17 shows the synthetic scheme (scheme 14) for the synthesis of fragment B [compounds 41(a-l)].
Figure 19:
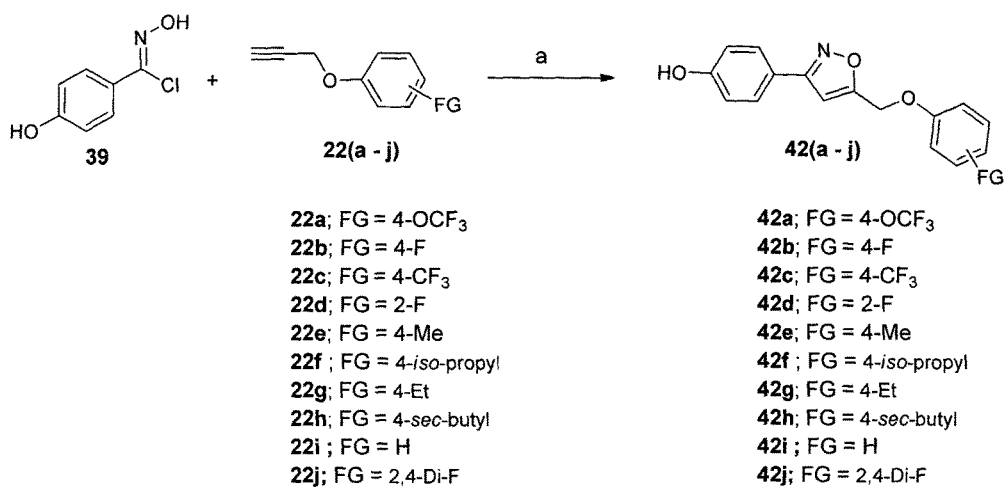
FIG. 19 shows the synthetic scheme (scheme 16) for the synthesis of fragment C (compounds 42 a-j).

Triazolyl based fragment B, that is compounds 13(a-p), 16(a-d), 19(a-d), 23(a-h), 24(a-f) and 25 (a-d) were synthesized by following method reported in the literature (Boechat, N.; Ferreira, V. F.; Ferreira, S. B.; Ferreira, M. L. G.; Silva, F. C.; Bastos, M. M.; Costa, M. S.; Lourenc-o, M. C. S.; Pinto, A. C.; Krettli, A. U.; Aguiar, A. C.; Teixeira, B. M.; Silva, N. V.; Martins, P. R. C.; Bezerra, F. A. F. M.; Camilo, A. L. S.; Silva, G. P.; Costa, C. C. P.; *J. Med. Chem.* 2011, 54, 5988-5999) as shown in the scheme 2 (provided in FIG. 5), in scheme 3 (provided in FIG. 6), in scheme 4 (provided in FIG. 7), in scheme 6 (provided in FIG. 9), in scheme 7 (provided in FIG. 10) and in scheme 8 (provided in FIG. 11), respectively. Tetrazolyl based fragment B, that is compounds 30(a-f) and 36 (a-d) were synthesized by following method reported in literature (Aldhoun, M.; Massi, A.; Dondoni, A.; *J. Org. Chem.* 2008, 73, 9565-9575) as shown in scheme 10 (provided in FIG. 13) and in scheme 12 (provided in FIG. 15), respectively. Similarly, isoxazolyl based fragment B, that is compounds 41(a-l) and 42(a-j) were synthesized from commercially available starting material by following the method reported in the literature (Himo, F.; Lovell, F.; Hilgraf, R.; Rostovtsev, V. V.; Noodleman, L.; Sharpless, K. B.; Fokin, V. V.; *J. Am. Chem. Soc.* 2005, 127, 210-216) as shown in scheme 14 (provided in FIG. 17) and in scheme 16 (provided in FIG. 19), respectively.

Example 3: Synthesis of Fragment C

Figure 21:
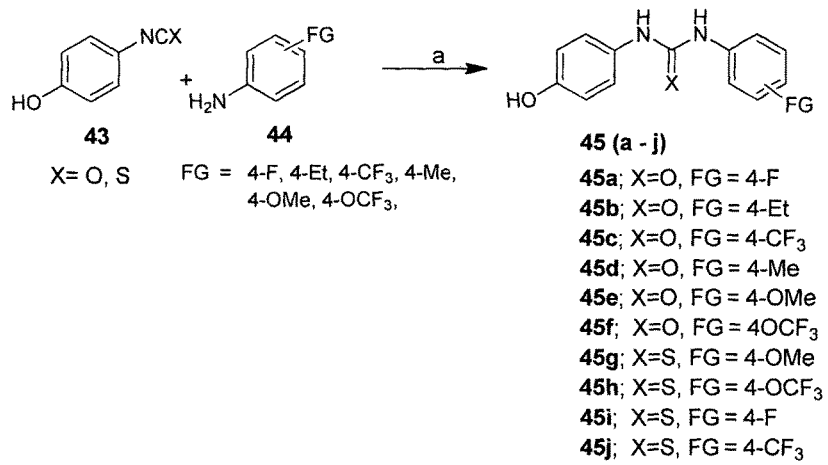
FIG. 21 shows the synthetic scheme (scheme 18) for the synthesis of fragment C [compounds 45(a-j)].
Figure 23:
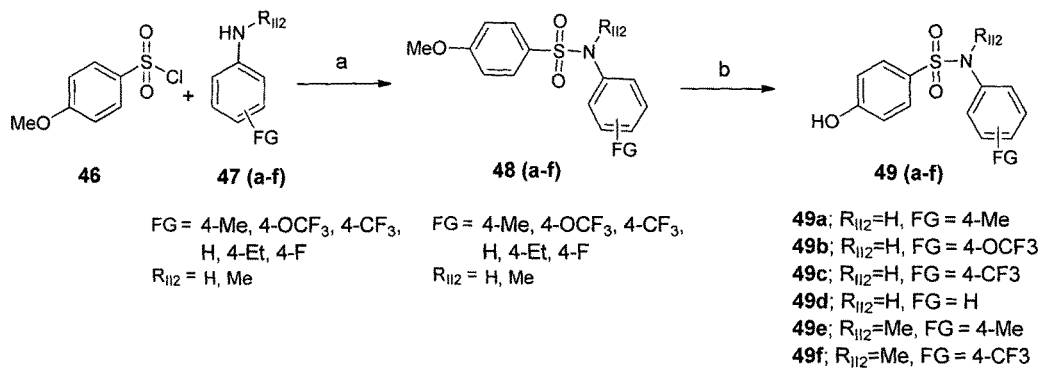
FIG. 23 shows the synthetic scheme (scheme 20) for the synthesis of fragment C [compounds 49(a-f)].
Figure 25:
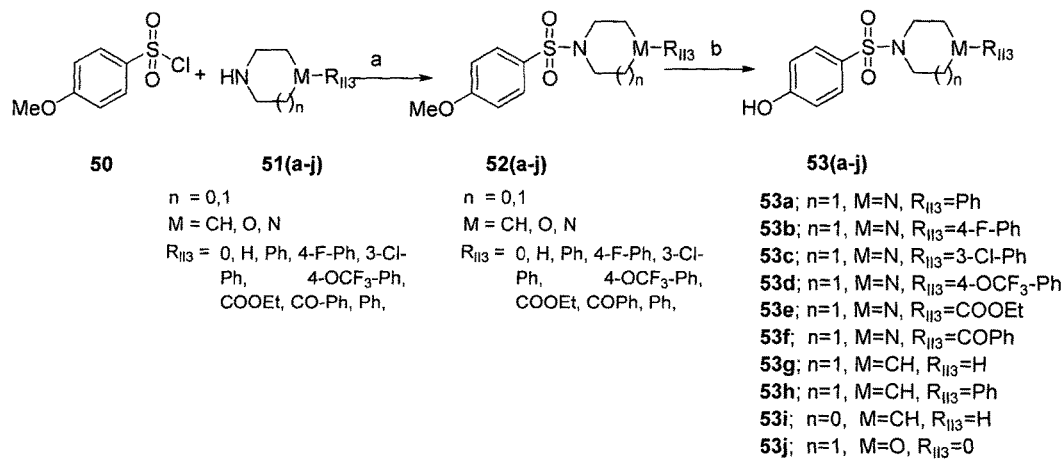
FIG. 25 shows the synthetic scheme (scheme 22) for the synthesis of fragment C [compounds 53(a-j)].

First uridyl based fragment C, that is compound 45(a-j) was synthesized from commercially available starting materials by following the method reported in literature (Valgeirsson, J.; Nielsen, E.; Peters, D.; Varming, T.; Mathiesen, C.; Kristensen, A. S.; Madsen, U.; *J. Med. Chem.* 2003, 46, 5835) as shown in scheme 18 (provided in FIG. 21). Sulphonamide based fragment C, that is compounds 49(a-f) and 53(a-j) were successfully synthesized by following method reported in the literature (Moreno-Diaz, H.; Villalobos-Molina, R.; Ortiz-Andrade, R.; Diaz-Coutin, D.; Medina-Franco, J. L.; Webster, S. P.; Binnie, M.; Estrada-Soto, S.; Ibarra-Barajas, M.; Leon-Rivera, I.; Navarrete-Vazquez, G.; *Bioorg. Med. Chem. Lett.* 2008, 18, 2871-2877) as shown in scheme 20 (provided in FIG. 23) and in scheme 22 (provided in FIG. 25), respectively.

Example 4: Synthesis of Compound of Formula 1

General Procedure for the Preparation of Compounds (IA1-42), (IB1-10), (IC1-22), (IIA1-10), (IIB1-6), (IIC1-10)

To a mixture of compound 9 (0.127 g, 0.586 mmol) and a compound selected from the group consisting of compounds 13(a-p), 16(a-d), 19(a-d), 23 (a-h), 24(a-f), 25(a-d), 30(a-f), 36(a-d), 41(a-l), 42(a-j), 45(a-j), 49(a-f) and 53(a-j) (0.468 mmol) in N,N-dimethylformamide (3 mL), 60% sodium hydride (0.022 g, 0.562 mmol) was added at 0° C. portionwise to obtain a mixture. After the mixture was stirred at 50° C. for 12 hrs under a nitrogen atmosphere, the mixture was cooled in an ice bath and carefully quenched with ethyl acetate (2.3 mL) and ice water (0.5 mL). The thus-obtained mixture was poured into water (30 mL) and extracted with ethylacetate, washed twice with brine solution and dried under vacuum to obtain a crude product. This crude product was purified by silica gel column chromatography using a dichloromethane and ethyl acetate mixture as solvent to obtain compounds (IA1-42), (IB1-10), (IC1-22), (IIA1-10), (IIB1-6) and (IIC1-10).

Example 5: Synthesis of Compound of Formula 1

General Procedure for the Preparation of Compounds (IA1-42), (IB1-10), (IC1-22), (IIA1-10), (IIB1-6), (IIC1-10)

To a mixture of compound 9 (0.127 g, 0.586 mmol) and a compound selected from the group consisting of compounds 13(a-p), 16(a-d), 19(a-d), 23 (a-h), 24(a-f), 25(a-d), 30 (a-f), 36(a-d), 41(a-l), 42(a-j), 45(a-j), 49(a-f) and 53(a-j) (0.468 mmol) in N,N-dimethylformamide (3 mL), cesium carbonate (0.562 mmol) was added at 0° C. portionwise to obtain a mixture. After the mixture was stirred at 80° C. for 12 hrs under a nitrogen atmosphere, the mixture was cooled in an ice bath. The mixture was then poured into ice water (30 mL) and extracted with ethylacetate, washed twice with brine solution and dried under vacuum to obtain a crude product. This crude product was purified by silica gel column chromatography using a dichloromethane and ethyl acetate mixture as solvent to obtain compounds (IA1-42), (IB1-10), (IC1-22), (IIA1-10), (IIB1-6) and (IIC1-10).

Example 6: Synthesis of Compound of Formula 1

General Procedure for the Preparation of Compounds (IA1-42), (IB1-10), (IC1-22), (IIA1-10), (IIB1-6), (IIC1-10)

To a mixture of compound 9 (0.127 g, 0.586 mmol) and a compound selected from the group consisting of compounds 13(a-p), 16(a-d), 19(a-d), 23 (a-h), 24(a-f), 25(a-d), 30(a-f), 36(a-d), 41(a-l), 42(a-j), 45(a-j), 49(a-f) and 53(a-j) (0.468 mmol) in THF (3 mL), 60% sodium hydride (0.022 g, 0.562 mmol) was added at 0° C. portionwise to obtain a mixture. After the mixture was stirred at 80° C. for 24 hrs under a nitrogen atmosphere, the mixture was cooled in an ice bath and carefully quenched with ethyl acetate (2.3 mL) and ice water (0.5 mL). The thus-obtained mixture was poured into water (30 mL) and extracted with ethylacetate, washed twice with brine solution and dried under vacuum to obtain a crude product. This crude product was purified by silica gel column chromatography using a dichloromethane and ethyl acetate mixture as solvent to obtain compounds (IA1-42), (IB1-10), (IC1-22), (IIA1-10), (IIB1-6), (IIC1-10).

Example 7: Synthesis of Compound of Formula 1

General Procedure for the Preparation of Compounds (IA1-42), (IB1-10), (IC1-22), (IIA1-10), (IIB1-6), (IIC1-10)

To a mixture of compound 9 (0.127 g, 0.586 mmol) and a compound selected from the group consisting of compounds 13(a-p), 16(a-d), 19(a-d), 23 (a-h), 24(a-f), 25(a-d), 30(a-f), 36(a-d), 41(a-l), 42(a-j), 45(a-j), 49(a-f) and 53(a-j) (0.468 mmol) in ACN (3 mL), potassium carbonate (0.562 mmol) was added at 0° C. portionwise to obtain a mixture. After the mixture was stirred at 80° C. for 24 hrs under a nitrogen atmosphere, the mixture was cooled in an ice bath. The mixture was poured into water (30 mL) and extracted with ethylacetate, washed twice with brine solution and dried under vacuum to obtain a crude product. This crude product was purified by silica gel column chromatography using a dichloromethane and ethyl acetate mixture as solvent to obtain compounds (IA1-42), (IB1-10), (IC1-22), (IIA1-10), (IIB1-6), (IIC1-10).

Example 8: Synthesis of Compound of Formula 1

General Procedure for the Preparation of Compounds (IA1-42), (IB1-10), (IC1-22), (IIA1-10), (IIB1-6), (IIC1-10)

To a mixture of compound 9 (0.127 g, 0.586 mmol) and a compound selected from the group consisting of compounds 13(a-p), 16(a-d), 19(a-d), 23 (a-h), 24(a-f), 25(a-d), 30(a-f), 36(a-d), 41(a-l), 42(a-j), 45(a-j), 49(a-f) and 53(a-j) (0.468 mmol) in ACN (3 mL), cesium carbonate (0.562 mmol) was added at 0° C. portionwise to obtain a mixture. After the mixture was stirred at 80° C. for 24 hrs under a nitrogen atmosphere, the mixture was cooled in an ice bath. The mixture was poured into water (30 mL) and extracted with ethylacetate, washed twice with brine solution and dried under vacuum to obtain a crude product. This crude product was purified by silica gel column chromatography using a dichloromethane and ethyl acetate mixture as solvent to obtain compounds (IA1-42), (IB1-10), (IC1-22), (IIA1-10), (IIB1-6), (IIC1-10).

Example 9: Synthesis of Compound of Formula 1

General Procedure for the Preparation of Compounds (IA1-42), (IB1-10), (IC1-22), (IIA1-10), (IIB1-6), (IIC1-10)

To a mixture of compound 9 (0.127 g, 0.586 mmol) and a compound selected from the group consisting of compounds 13(a-p), 16(a-d), 19(a-d), 23 (a-h), 24(a-f), 25(a-d), 30(a-f), 36(a-d), 41(a-l), 42(a-j), 45(a-j), 49(a-f) and 53(a-j) (0.468 mmol) in Acetone (3 mL), potassium carbonate (0.562 mmol) was added at 0° C. portionwise to obtain a mixture. After the mixture was stirred at 60° C. for 18 hrs under a nitrogen atmosphere, the mixture was cooled in an ice bath. The mixture was poured into water (30 mL) and extracted with ethylacetate, washed twice with brine solution and dried under vacuum to obtain a crude product. This crude product was purified by silica gel column chromatography using a dichloromethane and ethyl acetate mixture as solvent to obtain compounds (IA1-42), (IB1-10), (IC1-22), (IIA1-10), (IIB1-6), (IIC1-10).

Example 10: Synthesis of the Compound of Formula 1

General Procedure for the Preparation of Compounds (IA1-42), (IB1-10), (IC1-22), (IIA1-10), (IIB1-6), (IIC1-10)

To a mixture of compound 9 (0.127 g, 0.586 mmol) and a compound selected from the group consisting of com pounds 13(a-p), 16(a-d), 19(a-d), 23 (a-h), 24(a-f), 25(a-d), 30(a-f), 36(a-d), 41(a-l), 42(a-j), 45(a-j), 49(a-f) and 53(a-j)(0.468 mmol) in DCM (5 mL), 60% sodium hydride (0.022 g, 0.562 mmol) was added at 0° C. portionwise to obtain a mixture. After the mixture was stirred at 40° C. for 24 hrs under a nitrogen atmosphere, the mixture was cooled in an ice bath and carefully quenched with ethyl acetate (2.3 mL) and ice water (0.5 mL). The thus-obtained mixture was poured into water (30 mL) and extracted with ethylacetate, washed twice with brine solution and dried under vacuum to obtain a crude product. This crude product was purified by silica gel column chromatography using a dichloromethane and ethyl acetate mixture as solvent to obtain (IA1-42), (IB1-10), (IC1-22), (IIA1-10), (IIB1-6), (IIC1-10).

(R)-2-{4-(4-phenyl-1H-1,2,3-triazol-1-yl)phenoxy)methyl}-2,3-dihydro-2-methyl-6-nitroimidazo[2,1-b]oxazole (compound IA1, Table 1, FIG. 8)

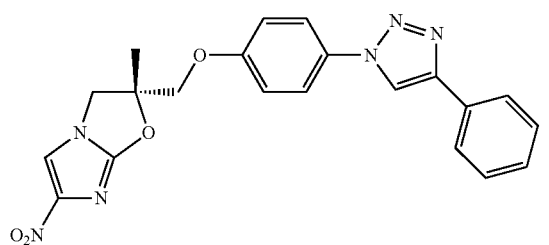 [SMILES: C[C@]1(COc2ccc(-n3cc(-c4ccccc4)nn3)cc2)Cn2cc([N+](=O)[O-])nc2O1]

TLC (DCM: EtOAc 1:9): $R_f$=0.30; $^1$H NMR (400 MHz, Acetone $d_6$): δ1.86 (s, 3H), 4.39 (d, 1H, J=10.8 Hz), 4.50 (dd, 2H, J=21.1, 10.6 Hz), 4.69 (d, 1H, J=10.8 Hz), 6.95 (d, 2H, J=7.5 Hz), 7.41 (m, 1H), 7.45 (d, 2H, J=7.5 Hz), 7.51 (m, 2H), 7.79 (m, 2H), 8.08 (s, 1H), 9.08 (s, 1H); MS (ESI+): m\z 418.14.

(R)-2-{4-[4-(4-ethylphenyl)-1H-1,2,3-triazol-1-yl]phenoxymethyl}-2,3-dihydro-2-methyl-6-nitroimidazo[2,1-b]oxazole (compound IA2, Table 1, FIG. 8)

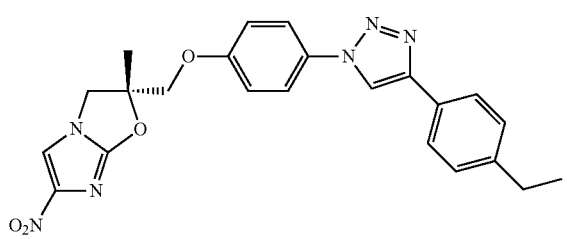 [SMILES: CCc1ccc(-c2cn(-c3ccc(OC[C@@]4(C)Cn5cc([N+](=O)[O-])nc5O4)cc3)nn2)cc1]

TLC (DCM: EtOAc 1:9): $R_f$=0.32; $^1$H NMR (400 MHz, Acetone $d_6$): δ1.25 (t, 3H, J=8), 1.86 (s, 3H), 2.60 (m, 3H), 4.39 (d, 1H, J=10.8 Hz), 4.50 (dd, 2H, J=21.1, 10.6 Hz), 4.69 (d, 1H, J=10.8 Hz), 6.95 (d, 2H, J=7.5 Hz), 7.35 (d, 1H, J=7.8), 7.45 (d, 2H, J=7.5 Hz), 7.74 (d, 2H, J=7.8), 8.09 (s, 1H), 9.10 (s, 1H); MS (ESI+): m\z 446.17.

(R)-2-{4-[4-(4-fluorophenyl)-1H-1,2,3-triazol-1-yl]phenoxymethyl}-2,3-dihydro-2-methyl-6-nitroimidazo[2,1-b]oxazole (compound IA3, Table 1, FIG. 8)

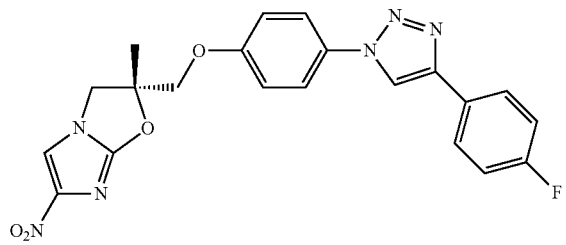 [SMILES: C[C@]1(COc2ccc(-n3cc(-c4ccc(F)cc4)nn3)cc2)Cn2cc([N+](=O)[O-])nc2O1]

TLC (DCM: EtOAc 1:9): $R_f$=0.35; $^1$H NMR (400 MHz, Acetone $d_6$): δ1.86 (s, 3H), 4.39 (d, 1H, J=10.8 Hz), 4.50 (dd, 2H, J=21.1, 10.6 Hz), 4.69 (d, 1H, J=10.8 Hz), 6.97 (d, 2H, J=7.6 Hz), 7.30 (m, 2H), 7.45 (d, 2H, J=7.6 Hz), 8.08 (s, 1H), 8.15 (m, 2H), 9.10 (s, 1H); MS (ESI+): m\z 436.13.

(R)-2-{4-[4-(2-fluorophenyl)-1H-1,2,3-triazol-1-yl]phenoxymethyl}-2,3-dihydro-2-methyl-6-nitroimidazo[2,1-b]oxazole (compound IA4, Table 1, FIG. 8)

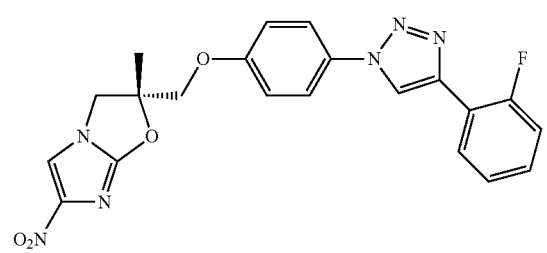 [SMILES: C[C@]1(COc2ccc(-n3cc(-c4ccccc4F)nn3)cc2)Cn2cc([N+](=O)[O-])nc2O1]

TLC (DCM: EtOAc 1:9): $R_f$=0.35; $^1$H NMR (400 MHz, Acetone $d_6$): δ1.86 (s, 3H), 4.39 (d, 1H, J=10.8 Hz), 4.50 (dd, 2H, J=21.1, 10.6 Hz), 4.69 (d, 1H, J=10.8 Hz), 6.95 (d, 2H, J=7.6 Hz), 7.28 (m, 1H), 7.45 (d, 2H, J=7.6 Hz), 7.49 (m, 1H), 7.71-7.77 (m, 2H), 8.08 (s, 1H), 9.10 (s, 1H); MS (ESI+): m\z 436.13.

(R)-2-{4-[4-(4-trifluoromethoxyphenyl)-1H-1,2,3-triazol-1-yl]phenoxymethyl}-2,3-dihydro-2-methyl-6-nitroimidazo[2,1-b]oxazole (compound IA5, Table 1, FIG. 8)

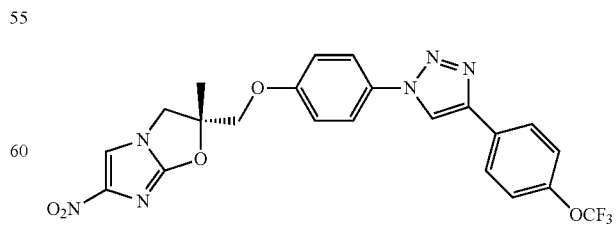

TLC (DCM: EtOAc 1:9): $R_f$=0.40; $^1$H NMR (400 MHz, Acetone $d_6$): δ1.86 (s, 3H), 4.39 (d, 1H, J=10.8 Hz), 4.50 (dd, 2H, J=21.1, 10.6 Hz), 4.69 (d, 1H, J=10.8 Hz), 6.99 (d, 2H, J=7.6 Hz), 7.05 (d, 2H, J=7.8 Hz), 7.45 (d, 2H, J=7.6 Hz), 7.55 (d, 2H, J=7.8 Hz), 8.08 (s, 1H), 8.96 (s, 1H); MS (ESI+): m\z 502.12.

(R)-2-{4-[4-(2-trifluoromethylphenyl)-1H-1,2,3-triazol-1-yl]phenoxymethyl}-2,3-dihydro-2-methyl-6-nitroimidazo[2,1-b]oxazole (compound IA6, Table 1, FIG. 8)

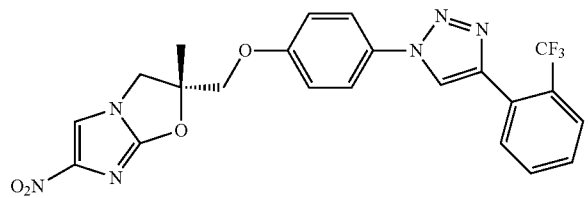 [SMILES: C[C@]1(COc2ccc(-n3cc(-c4ccccc4C(F)(F)F)nn3)cc2)Cn2cc([N+](=O)[O-])nc2O1]

TLC (DCM: EtOAc 1:9): $R_f$=0.40; $^1$H NMR (400 MHz, Acetone d$_6$): δ1.86 (s, 3H), 4.41 (d, 1H, J=10.8 Hz), 4.52 (dd, 2H, J=21.1, 10.6 Hz), 4.70 (d, 1H, J=10.8 Hz), 6.97 (d, 2H, J=7.6 Hz), 7.45 (d, 2H, J=7.6 Hz), 7.68 (d, 2H, J=7.9 Hz), 7.72 (d, 2H, J=7.9 Hz), 8.08 (s, 1H), 9.10 (s, 1H); MS (ESI+): m\z 486.13.

(R)-2-{4-[4-(2,4-difluorophenyl)-1H-1,2,3-triazol-1-yl]phenoxymethyl}-2,3-dihydro-2-methyl-6-nitroimidazo[2,1-b]oxazole (compound IA7, Table 1, FIG. 8)

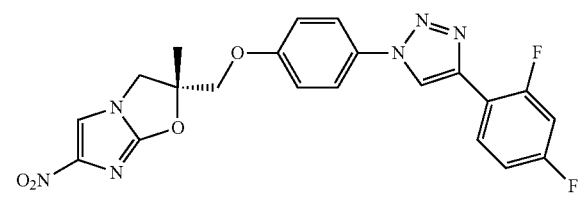 [SMILES: C[C@]1(COc2ccc(-n3cc(-c4ccc(F)cc4F)nn3)cc2)Cn2cc([N+](=O)[O-])nc2O1]

TLC (DCM: EtOAc 1:9): $R_f$=0.40; $^1$H NMR (400 MHz, Acetone d$_6$): δ1.80 (s, 3H), 4.45 (d, 1H, J=10.8 Hz), 4.56 (dd, 2H, J=21.1, 10.6 Hz), 4.72 (d, 1H, J=10.8 Hz), 6.79 (m, 1H), 6.95 (d, 2H, J=7.6 Hz), 7.07 (m, 2H, J=7.9 Hz), 7.45 (d, 2H, J=7.6 Hz), 7.75 (d, 2H, J=7.9 Hz), 8.08 (s, 1H), 9.09 (s, 1H); MS (ESI+): m\z 454.12.

(R)-2-{4-[4-(4-methylphenyl)-1H-1,2,3-triazol-1-yl]phenoxymethyl}-2,3-dihydro-2-methyl-6-nitroimidazo[2,1-b]oxazole (compound IA8, Table 1, FIG. 8)

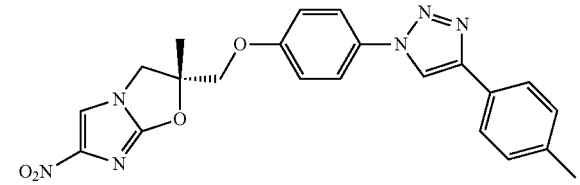 [SMILES: Cc1ccc(-c2cn(-c3ccc(OC[C@@]4(C)Cn5cc([N+](=O)[O-])nc5O4)cc3)nn2)cc1]

TLC (DCM: EtOAc 1:9): $R_f$=0.30; $^1$H NMR (400 MHz, Acetone d$_6$): δ 1.86 (s, 3H), 2.15 (s, 3H), 4.45 (d, 1H, J=10.8 Hz), 4.56 (dd, 2H, J=21.1, 10.6 Hz), 4.72 (d, 1H, J=10.8 Hz), 6.95 (d, 2H, J=7.6 Hz), 7.30 (d, 2H, J=7.8 Hz), 7.45 (d, 2H, J=7.6 Hz), 7.78 (d, 2H, J=7.8 Hz), 8.15 (s, 1H), 8.99 (s, 1H); MS (ESI+): m\z 432.12.

(R)-2-{4-[4-(4-isopropylphenyl)-1H-1,2,3-triazol-1-yl]phenoxymethyl}-2,3-dihydro-2-methyl-6-nitroimidazo[2,1-b]oxazole (compound IA9, Table 1, FIG. 8)

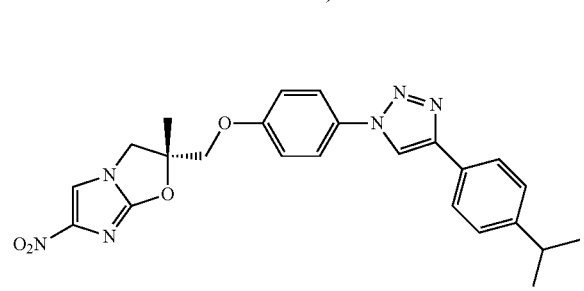

TLC (DCM: EtOAc 1:9): $R_f$=0.40; $^1$H NMR (400 MHz, Acetone d$_6$): δ 1.35 (d, 6H, J=8.5 Hz), 1.86 (s, 3H), 2.15 (m, 1H, J=8.5 Hz), 4.45 (d, 1H, J=10.8 Hz), 4.56 (dd, 2H, J=21.1, 10.6 Hz), 4.72 (d, 1H, J=10.8 Hz), 6.95 (d, 2H, J=7.6 Hz), 7.30 (d, 2H, J=7.8 Hz), 7.45 (d, 2H, J=7.6 Hz), 7.78 (d, 2H, J=7.8 Hz), 8.15 (s, 1H), 8.99 (s, 1H); MS (ESI+): m\z 460.19.

(R)-2-{4-[4-(3-fluorophenyl)-1H-1,2,3-triazol-1-yl]phenoxymethyl}-2,3-dihydro-2-methyl-6-nitroimidazo[2,1-b]oxazole (compound IA10, Table 1, FIG. 8):

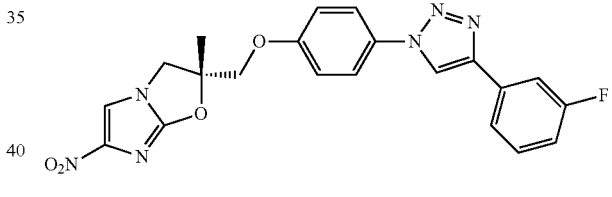

TLC (DCM: EtOAc 1:9): $R_f$=0.35; $^1$H NMR (400 MHz, Acetone d$_6$): δ1.85 (s, 3H), 4.45 (d, 1H, J=10.8 Hz), 4.56 (dd, 2H, J=21.1, 10.6 Hz), 4.72 (d, 1H, J=10.8 Hz), 6.95 (d, 2H, J=7.6 Hz), 7.20 (m, 1H), 7.45 (d, 2H, J=7.6 Hz), 7.49-7.52 (m, 3H), 8.15 (s, 1H), 9.01 (s, 1H); MS (ESI+): m\z 436.13.

(R)-2-{4-[4-(4-methoxyphenyl)-1H-1,2,3-triazol-1-yl]phenoxymethyl}-2,3-dihydro-2-methyl-6-nitroimidazo[2,1-b]oxazole (compound IA11, Table 1, FIG. 8)

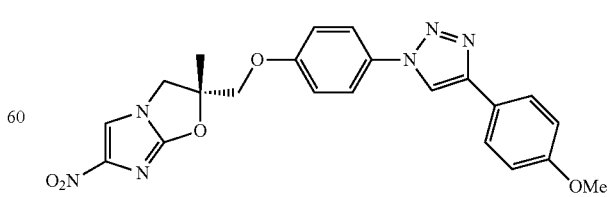

TLC (DCM: EtOAc 1:9): $R_f$=0.35; $^1$H NMR (400 MHz, Acetone d$_6$): δ1.85 (s, 3H), 4.15 (s, 3H), 4.45 (d, 1H, J=10.8 Hz), 4.56 (dd, 2H, J=21.1, 10.6 Hz), 4.72 (d, 1H, J=10.8 Hz), 6.95 (d, 2H, J=7.6 Hz), 7.09 (d, 2H, J=7.75 Hz), 7.45 (d, 2H, J=7.6 Hz), 7.68 (d, 2H, J=7.75 Hz), 8.15 (s, 1H), 8.89 (s, 1H); MS (ESI+): m\z 448.15.

(R)-2-{4-[4-(3-trifluoromethoxyphenyl)-1H-1,2,3-triazol-1-yl]phenoxymethyl}-2,3-dihydro-2-methyl-6-nitroimidazo[2,1-b]oxazole (compound IA12, Table 1, FIG. 8)

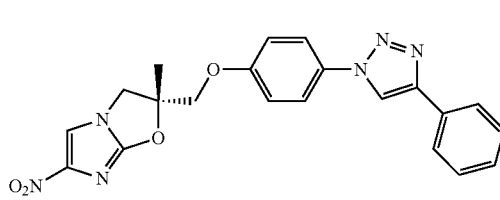

TLC (DCM: EtOAc 1:9): $R_f$=0.40; $^1$H NMR (400 MHz, Acetone $d_6$): δ1.86 (s, 3H), 4.39 (d, 1H, J=10.8 Hz), 4.50 (dd, 2H, J=21.1, 10.6 Hz), 4.69 (d, 1H, J=10.8 Hz), 6.95 (d, 2H, J=7.6 Hz), 7.20 (m, 1H), 7.45 (d, 2H, J=7.6 Hz), 7.45-7.50 (m, 3H), 8.15 (s, 1H), 8.92 (s, 1H); MS (ESI+): m\z 502.12.

(R)-2-{4-[4-(3-trifluoromethoxyphenyl)-1H-1,2,3-triazol-1-yl]phenoxymethyl}-2,3-dihydro-2-methyl-6-nitroimidazo[2,1-b]oxazole (compound IA13, Table 1, FIG. 8)

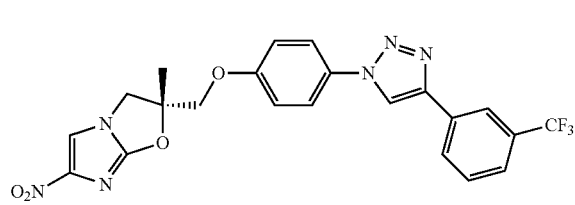 [SMILES: C[C@]1(COc2ccc(-n3cc(-c4cccc(C(F)(F)F)c4)nn3)cc2)Cn2cc([N+](=O)[O-])nc2O1]

TLC (DCM: EtOAc 1:9): $R_f$=0.40; $^1$H NMR (400 MHz, Acetone $d_6$): δ 1.88 (s, 3H), 4.39 (d, 1H, J=10.8 Hz), 4.50 (dd, 2H, J=21.1, 10.6 Hz), 4.69 (d, 1H, J=10.8 Hz), 6.95 (d, 2H, J=7.6 Hz), 7.40 (m, 1H), 7.45 (d, 2H, J=7.6 Hz), 7.47-7.50 (m, 3H), 8.10 (s, 1H), 9.10 (s, 1H); MS (ESI+): m\z 486.13.

(R)-2-{4-[4-(4-(pyridin-2-yl)-1H-1,2,3-triazol-1-yl]phenoxymethyl}-2,3-dihydro-2-methyl-6-nitroimidazo[2,1-b]oxazole (compound IA14, Table 1, FIG. 8)

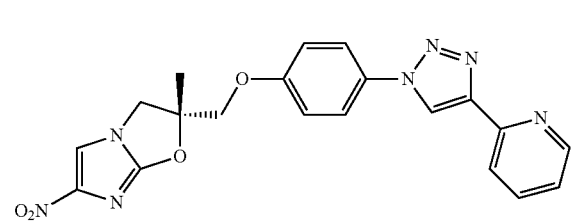 [SMILES: C[C@]1(COc2ccc(-n3cc(-c4ccccn4)nn3)cc2)Cn2cc([N+](=O)[O-])nc2O1]

TLC (DCM: EtOAc 1:9): $R_f$=0.20; $^1$H NMR (400 MHz, Acetone $d_6$): δ 1.89 (s, 3H), 4.39 (d, 1H, J=10.8 Hz), 4.50 (dd, 2H, J=21.1, 10.6 Hz), 4.69 (d, 1H, J=10.8 Hz), 6.95 (d, 2H, J=7.6 Hz), 7.36 (m, 1H), 7.45 (d, 2H, J=7.6 Hz), 7.85 (m, 1H), 8.10 (s, 1H), 8.40 (m, 1H), 8.65 (m, 1H), 9.01 (s, 1H); MS (ESI+): m\z 419.13.

(R)-2-{4-[4-pentyl-1H-1,2,3-triazol-1-yl]phenoxymethyl}-2,3-dihydro-2-methyl-6-nitroimidazo[2,1-b]oxazole (compound IA15, Table 1, FIG. 8)

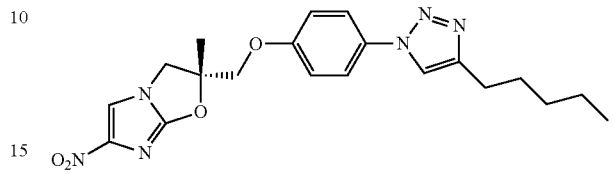

TLC (DCM: EtOAc 1:9): $R_f$=0.45; $^1$H NMR (400 MHz, Acetone $d_6$): δ 0.91 (m, 3H), 1.15 (m, 2H), 1.21 (m, 4H), 1.89 (s, 3H), 2.25 (t, 2H), 4.39 (d, 1H, J=10.8 Hz), 4.50 (dd, 2H, J=21.1, 10.6 Hz), 4.69 (d, 1H, J=10.8 Hz), 6.95 (d, 2H, J=7.6 Hz), 7.45 (d, 2H, J=7.6 Hz), 7.62 (s, 1H), 7.95 (s, 1H); MS (ESI+): m\z 412.19.

(R)-2-{4-[4-heptyl-1H-1,2,3-triazol-1-yl]phenoxymethyl}-2,3-dihydro-2-methyl-6-nitroimidazo[2,1-b]oxazole (compound IA16, Table 1, FIG. 8)

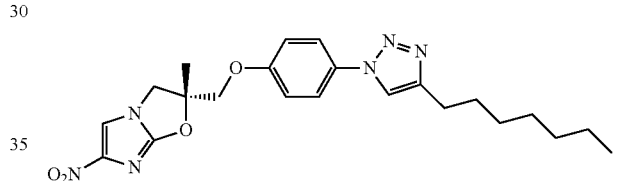

TLC (DCM: EtOAc 1:9): $R_f$=0.50; $^1$H NMR (400 MHz, Acetone $d_6$): δ 1.09 (m, 3H), 1.15 (m, 2H), 1.21-1.24 (m, 8H), 1.89 (s, 3H), 2.25 (t, 2H), 4.39 (d, 1H, J=10.8 Hz), 4.50 (dd, 2H, J=21.1, 10.6 Hz), 4.69 (d, 1H, J=10.8 Hz), 6.95 (d, 2H, J=7.6 Hz), 7.45 (d, 2H, J=7.6 Hz), 7.60 (s, 1H), 7.95 (s, 1H); MS (ESI+): m\z 440.22.

(R)-2-{3-[4-(4-fluorophenyl)-1H-1,2,3-triazol-1-yl]phenoxymethyl}-2,3-dihydro-2-methyl-6-nitroimidazo[2,1-b]oxazole (compound IA17, Table 2, FIG. 8)

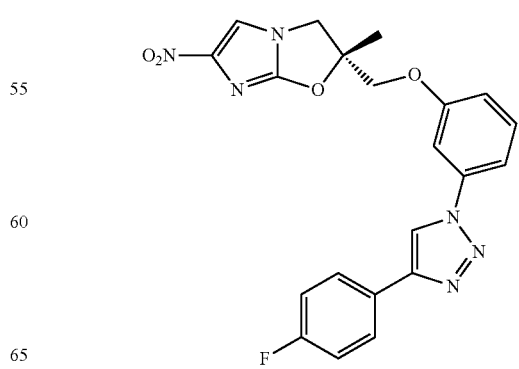

TLC (DCM: EtOAc 1:9): R$_f$=0.30; $^1$H NMR (400 MHz, Acetone d$_6$): δ1.89 (s, 3H), 4.39 (d, 1H, J=10.8 Hz), 4.50 (dd, 2H, J=21.1, 10.6 Hz), 4.69 (d, 1H, J=10.8 Hz), 6.91 (s, 1H), 6.95 (m, 1H), 7.18 (m, 1H), 7.20 (m, 1H), 7.30 (d, 2H, J=7.6 Hz), 8.15 (d, 2H, J=7.6 Hz), 8.18 (s, 1H), 8.98 (s, 1H); MS (ESI+): m\z 436.13.

(R)-2-{3-[4-(4-trifluoromethylphenyl)-1H-1,2,3-triazol-1-yl]phenoxymethyl}-2,3-dihydro-2-methyl-6-nitroimidazo[2,1-b]oxazole (compound IA18, Table 2, FIG. 8)

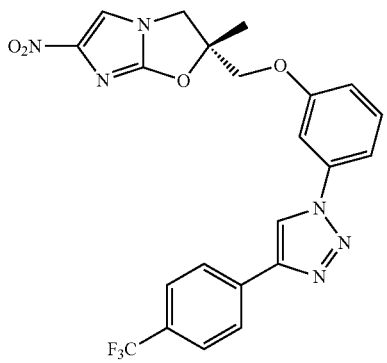 [SMILES: C[C@]1(COc2cccc(-n3cc(-c4ccc(C(F)(F)F)cc4)nn3)c2)Cn2cc([N+](=O)[O-])nc2O1]

TLC (DCM: EtOAc 1:9): R$_f$=0.35; $^1$H NMR (400 MHz, Acetone d$_6$): δ1.89 (s, 3H), 4.39 (d, 1H, J=10.8 Hz), 4.50 (dd, 2H, J=21.1, 10.6 Hz), 4.69 (d, 1H, J=10.8 Hz), 6.91 (s, 1H), 6.95 (m, 1H), 7.18 (m, 1H), 7.20 (m, 1H), 7.45 (d, 2H, J=7.6 Hz), 8.11 (d, 2H, J=7.6 Hz), 8.15 (s, 1H), 9.08 (s, 1H); MS (ESI+): m\z 486.13.

(R)-2-{3-[4-(4-trifluoromethoxyphenyl)-1H-1,2,3-triazol-1-yl]phenoxymethyl}-2,3-dihydro-2-methyl-6-nitroimidazo[2,1-b]oxazole (compound IA19, Table 2, FIG. 8)

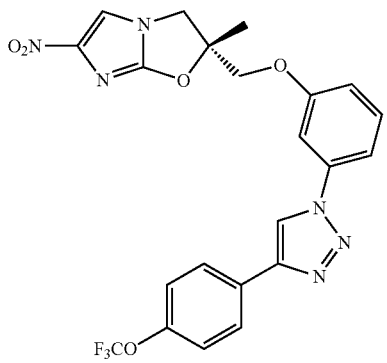 [SMILES: C[C@]1(COc2cccc(-n3cc(-c4ccc(OC(F)(F)F)cc4)nn3)c2)Cn2cc([N+](=O)[O-])nc2O1]

TLC (DCM: EtOAc 1:9): R$_f$=0.40; $^1$H NMR (400 MHz, Acetone d$_6$): δ1.89 (s, 3H), 4.39 (d, 1H, J=10.8 Hz), 4.50 (dd, 2H, J=21.1, 10.6 Hz), 4.69 (d, 1H, J=10.8 Hz), 6.91 (s, 1H), 6.95 (m, 1H), 7.18 (m, 1H), 7.20 (m, 1H), 7.35 (d, 2H, J=7.6 Hz), 7.82 (d, 2H, J=7.6 Hz), 8.05 (s, 1H), 8.89 (s, 1H); MS (ESI+): m\z 502.12.

(R)-2-{3-[4-(2,4-difluorophenyl)-1H-1,2,3-triazol-1-yl]phenoxymethyl}-2,3-dihydro-2-methyl-6-nitroimidazo[2,1-b]oxazole (compound IA20, Table 2, FIG. 8)

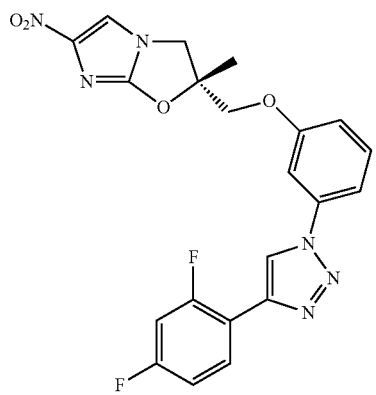

TLC (DCM: EtOAc 1:9): R$_f$=0.40; $^1$H NMR (400 MHz, Acetone d$_6$): δ 1.89 (s, 3H), 4.39 (d, 1H, J=10.8 Hz), 4.50 (dd, 2H, J=21.1, 10.6 Hz), 4.69 (d, 1H, J=10.8 Hz), 6.91 (s, 1H), 6.95 (m, 1H), 7.18 (m, 1H), 7.20 (m, 1H), 7.25 (m, 2H, J=7.9 Hz), 7.45 (d, 2H, J=7.6 Hz), 7.75 (d, 2H, J=7.9 Hz), 8.05 (s, 1H), 8.93 (s, 1H); LC MS (ESI+): m\z 454.12.

(R)-2-{2-[4-(4-fluorophenyl)-1H-1,2,3-triazol-1-yl]phenoxymethyl}-2,3-dihydro-2-methyl-6-nitroimidazo[2,1-b]oxazole (compound IA21, Table 2, FIG. 8)

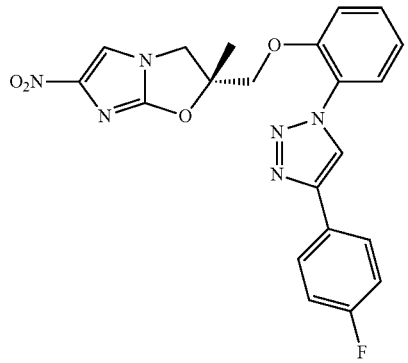 [SMILES: C[C@]1(COc2ccccc2-n2cc(-c3ccc(F)cc3)nn2)Cn2cc([N+](=O)[O-])nc2O1]

TLC (DCM: EtOAc 1:9): R$_f$=0.30; $^1$H NMR (400 MHz, Acetone d$_6$): δ 1.79 (s, 3H), 4.39 (d, 1H, J=10.8 Hz), 4.50 (dd, 2H, J=21.1, 10.6 Hz), 4.69 (d, 1H, J=10.8 Hz), 6.95 (m, 1H), 7.14 (m, 1H), 7.28 (m, 1H), 7.45 (m, 1H), 7.48 (d, 2H, J=7.6 Hz), 8.05 (d, 2H, J=7.6 Hz), 8.12 (s, 1H), 8.98 (s, 1H); MS (ESI+): m\z 436.13.

(R)-2-{2-[4-(4-trifluoromethylphenyl)-1H-1,2,3-triazol-1-yl]phenoxymethyl}-2,3-dihydro-2-methyl-6-nitroimidazo[2,1-b]oxazole (compound IA22, Table 2, FIG. 8)

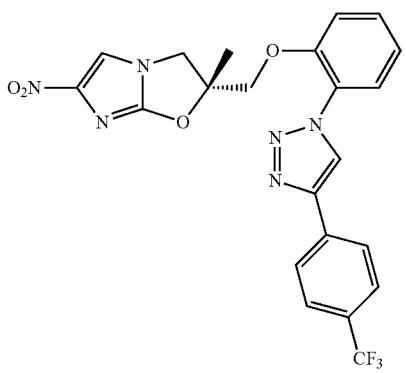 [SMILES: C[C@]1(COc2ccccc2-n2cc(-c3ccc(C(F)(F)F)cc3)nn2)Cn2cc([N+](=O)[O-])nc2O1]

TLC (DCM: EtOAc 1:9): R$_f$=0.35; $^1$H NMR (400 MHz, Acetone d$_6$): δ 1.87. (s, 3H), 4.39 (d, 1H, J=10.8 Hz), 4.50 (dd, 2H, J=21.1, 10.6 Hz), 4.69 (d, 1H, J=10.8 Hz), 6.95 (m, 1H), 7.14 (m, 1H), 7.28 (m, 1H), 7.45 (m, 1H), 7.68 (d, 2H, J=7.6 Hz), 8.05 (d, 2H, J=7.6 Hz), 8.12 (s, 1H), 9.08 (s, 1H); MS (ESI+): m\z 486.13.

(R)-2-{2-[4-(4-trifluoromethoxyphenyl)-1H-1,2,3-triazol-1-yl]phenoxymethyl}-2,3-dihydro-2-methyl-6-nitroimidazo[2,1-b]oxazole (compound IA23, Table 2, FIG. 8)

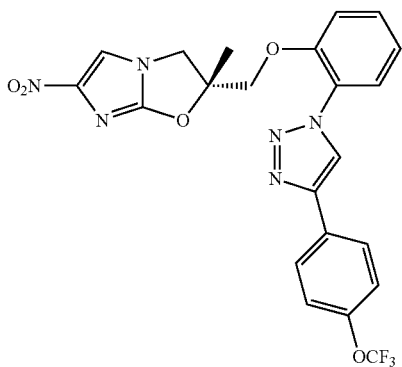 [SMILES: C[C@]1(COc2ccccc2-n2cc(-c3ccc(OC(F)(F)F)cc3)nn2)Cn2cc([N+](=O)[O-])nc2O1]

TLC (DCM: EtOAc 1:9): R$_f$=0.40; $^1$H NMR (400 MHz, Acetone d$_6$): δ 1.85 (s, 3H), 4.37 (d, 1H, J=10.8 Hz), 4.52 (dd, 2H, J=21.1, 10.6 Hz), 4.66 (d, 1H, J=10.8 Hz), 6.97 (m, 1H), 7.14 (m, 1H), 7.28 (m, 1H), 7.45 (m, 1H), 7.34 (d, 2H, J=7.6 Hz), 7.85 (d, 2H, J=7.6 Hz), 8.02 (s, 1H), 8.87 (s, 1H); MS (ESI+): m\z 502.12.

(R)-2-{2-[4-(2,4-difluorophenyl)-1H-1,2,3-triazol-1-yl]phenoxymethyl}-2,3-dihydro-2-methyl-6-nitroimidazo[2,1-b]oxazole (compound IA24, Table 2, FIG. 8)

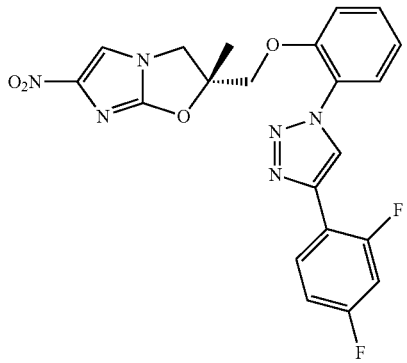 [SMILES: C[C@]1(COc2ccccc2-n2cc(-c3ccc(F)cc3F)nn2)Cn2cc([N+](=O)[O-])nc2O1]

TLC (DCM: EtOAc 1:9): R$_f$=0.40; $^1$H NMR (400 MHz, Acetone d$_6$): δ1.89 (s, 3H), 4.35 (d, 1H, J=10.8 Hz), 4.49 (dd, 2H, J=21.1, 10.6 Hz), 4.66 (d, 1H, J=10.8 Hz), 6.74 (s, 1H), 6.95 (m, 1H), 7.07 (d, 1H, J=8.05 Hz), 7.14 (m, 1H), 7.20 (m, 1H), 7.45 (m, 2H), 7.75 (d, 2H, J=8.05 Hz), 8.05 (s, 1H), 8.90 (s, 1H); MS (ESI+): m\z 454.12.

(R)-2-{4-[4-(4-trifluoromethoxyphenoxy)methyl)-1H-1,2,3-triazol-1-yl]phenoxymethyl}-2,3-dihydro-2-methyl-6-nitroimidazo[2,1-b]oxazole (compound IA25, Table 3, FIG. 12)

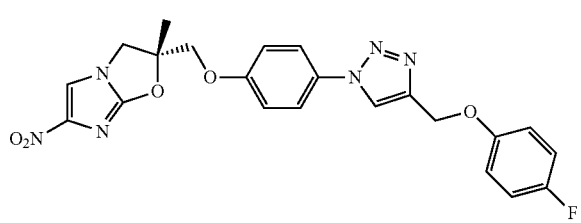 [SMILES: C[C@]1(COc2ccc(-n3cc(COc4ccc(F)cc4)nn3)cc2)Cn2cc([N+](=O)[O-])nc2O1]

TLC (DCM: EtOAc 1:9): R$_f$=0.40; $^1$H NMR (400 MHz, CDCl$_3$): δ 1.82 (s, 3H), 4.09 (d, 1H, J=10.3 Hz), 4.16 (d, 1H, J=10.2 Hz), 4.32 (d, 1H, J=10.3 Hz), 4.53 (d, 1H, J=10.2 Hz), 5.28 (s, 2H), 7.00 (m, 4H), 7.17 (d, 2H, J=8.7 Hz), 7.58 (s, 1H), 7.66 (d, 2H, J=9.0 Hz), 7.99 (s, 1H); MS (ESI+): m\z 532.13.

(R)-2-{4-[4-(4-fluorophenoxy)methyl)-1H-1,2,3-triazol-1-yl]phenoxymethyl}-2,3-dihydro-2-methyl-6-nitroimidazo[2,1-b]oxazole (compound IA26, Table 3, FIG. 12)

TLC (DCM: EtOAc 1:9): $R_f$=0.35; $^1$H NMR (400 MHz, CDCl$_3$): δ 1.82 (s, 3H), 4.09 (d, 1H, J=10.2 Hz), 4.16 (d, 1H, J=10.1 Hz), 4.31 (d, 1H, J=10.1 Hz), 4.53 (d, 1H, J=10.3 Hz), 5.25 (s, 2H), 6.94-7.02 (m, 6H), 7.59 (s, 1H), 7.65 (d, 2H, J=8.8 Hz), 7.98 (s, 1H); MS (ESI+): m\z 466.14.

(R)-2-{4-[4-(4-trifluoromethylphenoxy)methyl)-1H-1,2,3-triazol-1-yl]phenoxymethyl}-2,3-dihydro-2-methyl-6-nitroimidazo[2,1-b]oxazole (compound IA27, Table 3, FIG. 12)

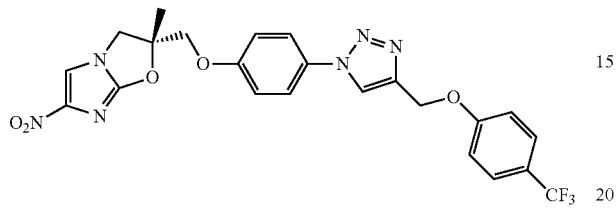

TLC (DCM: EtOAc 1:9): $R_f$=0.40; $^1$H NMR (400 MHz, CDCl$_3$): δ 1.82 (s, 3H), 4.09 (d, 1H, J=10.2 Hz), 4.16 (d, 1H, J=10.2 Hz), 4.31 (d, 1H, J=10.2 Hz), 4.52 (d, 1H, J=10.2 Hz), 5.33 (s, 2H), 6.99 (d, 2H, J=9.0 Hz), 7.10 (d, 2H, J=8.5 Hz), 7.57 (d, 2H, J=7.0 Hz), 7.35 (s, 1H), 7.66 (d, 2H, J=9.0 Hz), 7.99 (s, 1H); MS (ESI+): m\z 516.14.

(R)-2-{4-[4-(2-fluorophenoxy)methyl)-1H-1,2,3-triazol-1-yl]phenoxymethyl}-2,3-dihydro-2-methyl-6-nitroimidazo[2,1-b]oxazole (compound IA28, Table 3, FIG. 12)

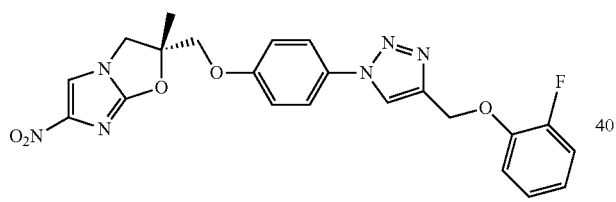

TLC (DCM: EtOAc 1:9): $R_f$=0.35; $^1$H NMR (400 MHz, CDCl$_3$): δ 1.82 (s, 3H), 4.09 (d, 1H, J=11.4 Hz), 4.16 (d, 1H, J=11.1 Hz), 4.31 (d, 1H, J=10.1 Hz), 4.53 (d, 1H, J=10.3 Hz), 5.36 (s, 2H), 6.96-6.92 (m, 1H), 6.99 (d, 2H, J=9.0 Hz), 7.09-7.13 (m, 2H), 7.16 (t, 1H, J=7.9 Hz), 7.59 (s, 1H), 7.66 (d, 2H, J=8.1 Hz), 8.03 (s, 1H); MS (ESI+): m\z 466.14.

(R)-2-{4-[4-(4-methylphenoxy)methyl)-1H-1,2,3-triazol-1-yl]phenoxymethyl}-2,3-dihydro-2-methyl-6-nitroimidazo[2,1-b]oxazole (compound IA29, Table 3, FIG. 12)

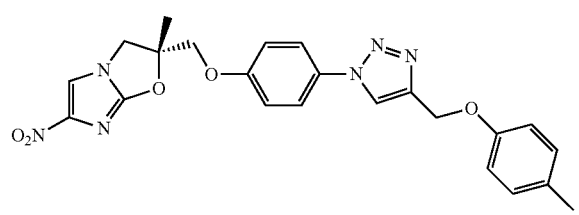 [SMILES: Cc1ccc(OCc2cn(-c3ccc(OC[C@@]4(C)Cn5cc([N+](=O)[O-])nc5O4)cc3)nn2)cc1]

TLC (DCM: EtOAc 1:9): $R_f$=0.30; $^1$H NMR (400 MHz, CDCl$_3$): δ 1.82 (s, 3H), 2.29 (s, 3H), 4.09 (d, 1H, J=10.3 Hz), 4.16 (d, 1H, J=10.2 Hz), 4.32 (d, 1H, J=10.3 Hz), 4.53 (d, 1H, J=10.2 Hz), 5.25 (s, 2H), 6.92 (d, 2H, J=8.5 Hz), 6.98 (d, 2H, J=8.9 Hz), 7.14 (d, 2H, J=8.5 Hz), 7.58 (s, 1H), 7.65 (d, 2H, J=8.9 Hz), 7.98 (s, 1H); MS (ESI+): m\z 462.17.

(R)-2-{4-[4-(4-isopropylphenoxy)methyl)-1H-1,2,3-triazol-1-yl]phenoxymethyl}-2,3-dihydro-2-methyl-6-nitroimidazo[2,1-b]oxazole (compound IA30, Table 3, FIG. 12)

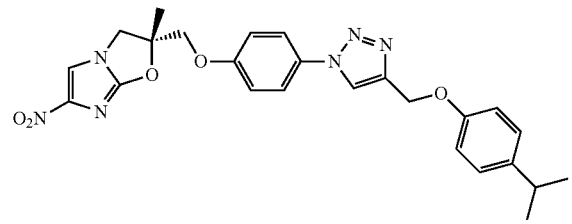 [SMILES: CC(C)c1ccc(OCc2cn(-c3ccc(OC[C@@]4(C)Cn5cc([N+](=O)[O-])nc5O4)cc3)nn2)cc1]

TLC (DCM: EtOAc 1:9): $R_f$=0.30; $^1$H NMR (400 MHz, CDCl$_3$): δ 1.21 (d, 6H, J=8.82 Hz), 1.81 (s, 3H), 2.12 (m, 1H, J=8.82 Hz), 4.09 (d, 1H, J=10.3 Hz), 4.16 (d, 1H, J=10.2 Hz), 4.32 (d, 1H, J=10.3 Hz), 4.53 (d, 1H, J=10.2 Hz), 5.22 (s, 2H), 6.92 (d, 2H, J=8.6 Hz), 6.98 (d, 2H, J=8.8 Hz), 7.17 (d, 2H, J=8.6 Hz), 7.58 (s, 1H), 7.65 (d, 2H, J=8.8 Hz), 7.98 (s, 1H); MS (ESI+): m\z 490.20.

(R)-2-{4-[4-(4-ethylphenoxy)methyl)-1H-1,2,3-triazol-1-yl]phenoxymethyl}-2,3-dihydro-2-methyl-6-nitroimidazo[2,1-b]oxazole (compound IA31, Table 3, FIG. 12)

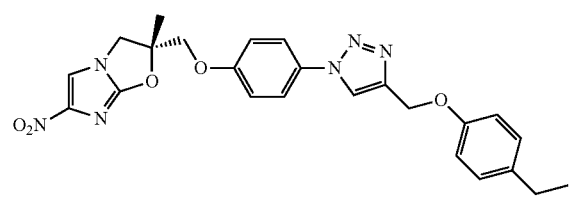 [SMILES: CCc1ccc(OCc2cn(-c3ccc(OC[C@@]4(C)Cn5cc([N+](=O)[O-])nc5O4)cc3)nn2)cc1]

TLC (DCM: EtOAc 1:9): $R_f$=0.35; $^1$H NMR (400 MHz, CDCl$_3$): δ 1.21 (t, 3H, J=7.6 Hz), 1.83 (s, 3H), 2.60 (m, 2H, J=7.6 Hz), 4.09 (d, 1H, J=10.3 Hz), 4.15 (d, 1H, J=10.1 Hz), 4.31 (d, 1H, J=10.1 Hz), 4.53 (d, 1H, J=10.3 Hz), 5.27 (s, 2H), 6.94 (d, 2H, J=8.5 Hz), 6.98 (d, 2H, J=9.0 Hz), 7.14 (d, 2H, J=8.5 Hz), 7.58 (s, 1H), 7.65 (d, 2H, J=9.0 Hz), 7.98 (s, 1H); MS (ESI+): m\z 476.18.

(R)-2-{4-[4-(4-sec-butylphenoxy)methyl)-1H-1,2,3-triazol-1-yl]phenoxymethyl}-2,3-dihydro-2-methyl-6-nitroimidazo[2,1-b]oxazole (compound IA32, Table 3, FIG. 12)

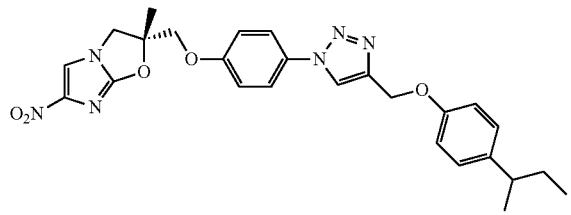 [SMILES: CCC(C)c1ccc(OCc2cn(-c3ccc(OC[C@@]4(C)Cn5cc([N+](=O)[O-])nc5O4)cc3)nn2)cc1]

TLC (DCM: EtOAc 1:9): $R_f$=0.40; $^1$H NMR (400 MHz, CDCl$_3$): δ 0.81 (t, 3H, J=8.85 Hz), 1.21 (d, 2H, J=8.95 Hz), 1.58-1.51 (m, 3H, J=8.85 Hz), 1.82 (s, 3H), 2.61 (m, 1H, J=8.95 Hz), 4.09 (d, 1H, J=10.3 Hz), 4.16 (d, 1H, J=10.2 Hz), 4.32 (d, 1H, J=10.3 Hz), 4.53 (d, 1H, J=10.2 Hz), 5.23 (s, 2H), 6.96 (m, 4H), 7.12 (d, 2H, J=8.6 Hz), 7.58 (s, 1H), 7.65 (d, 2H, J=8.7 Hz), 7.98 (s, 1H); MS (ESI+): m\z 504.21.

(R)-2-{3-[4-(4-trifluoromethoxyphenoxy)methyl)-1H-1,2,3-triazol-1-yl]phenoxymethyl}-2,3-dihydro-2-methyl-6-nitroimidazo[2,1-b]oxazole (compound IA33, Table 3, FIG. 12)

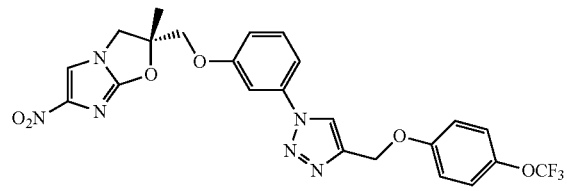 [SMILES: C[C@]1(COc2cccc(-n3cc(COc4ccc(OC(F)(F)F)cc4)nn3)c2)Cn2cc([N+](=O)[O-])nc2O1]

TLC (DCM: EtOAc 1:9): $R_f$=0.40; $^1$H NMR (400 MHz, CDCl$_3$): δ 1.81 (s, 3H), 4.08 (d, 1H, J=10.2 Hz), 4.18 (d, 1H, J=10.2 Hz), 4.34 (d, 1H, J=10.3 Hz), 4.51 (d, 1H, J=10.2 Hz), 5.28 (s, 2H), 6.93 (m, 1H), 7.02 (d, 2H, J=9.1 Hz), 7.17 (d, 2H, J=8.9 Hz), 7.34 (m, 2H), 7.44 (m, 1H), 7.57 (s, 1H), 8.05 (s, 1H); MS (ESI+): m\z 532.13.

(R)-2-{3-[4-(4-fluorophenoxy)methyl)-1H-1,2,3-triazol-1-yl]phenoxymethyl}-2,3-dihydro-2-methyl-6-nitroimidazo[2,1-b]oxazole (compound IA34, Table 3, FIG. 12)

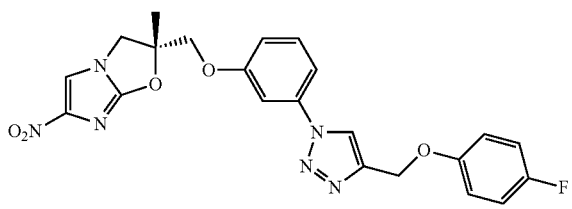 [SMILES: C[C@]1(COc2cccc(-n3cc(COc4ccc(F)cc4)nn3)c2)Cn2cc([N+](=O)[O-])nc2O1]

TLC (DCM: EtOAc 1:9): $R_f$=0.30; $^1$H NMR (400 MHz, CDCl$_3$): δ 1.81 (s, 3H), 4.08 (d, 1H, J=10.2 Hz), 4.18 (d, 1H, J=10.2 Hz), 4.34 (d, 1H, J=10.3 Hz), 4.51 (d, 1H, J=10.2 Hz), 5.25 (s, 2H), 6.90-7.03 (m, 5H), 7.33 (m, 2H), 7.43 (m, 1H), 7.57 (s, 1H), 8.04 (s, 1H); MS (ESI+): m\z 466.14.

(R)-2-{3-[4-(4-trifluoromethylphenoxy)methyl)-1H-1,2,3-triazol-1-yl]phenoxymethyl}-2,3-dihydro-2-methyl-6-nitroimidazo[2,1-b]oxazole (compound IA35, Table 3, FIG. 12)

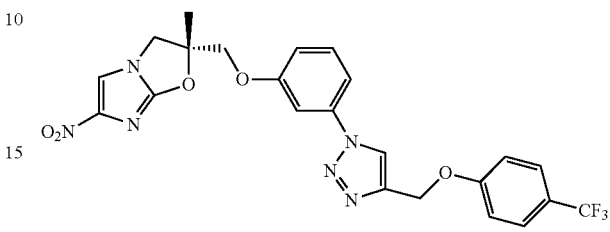

TLC (DCM: EtOAc 1:9): $R_f$=0.40; $^1$H NMR (400 MHz, CDCl$_3$): δ 1.82 (s, 3H), 4.09 (d, 1H, J=10.2 Hz), 4.19 (d, 1H, J=10.2 Hz), 4.36 (d, 1H, J=10.3 Hz), 4.53 (d, 1H, J=10.2 Hz), 5.29 (s, 2H), 6.93 (m, 1H), 7.02 (d, 2H, J=9.1 Hz), 7.17 (d, 2H, J=8.9 Hz), 7.34 (m, 2H), 7.44 (m, 1H), 7.85 (s; 1H), 8.15 (s, 1H); MS (ESI+): m\z 516.14.

(R)-2-{3-[4-(2-fluorophenoxy)methyl)-1H-1,2,3-triazol-1-yl]phenoxymethyl}-2,3-dihydro-2-methyl-6-nitroimidazo[2,1-b]oxazole (compound IA36, Table 3, FIG. 12)

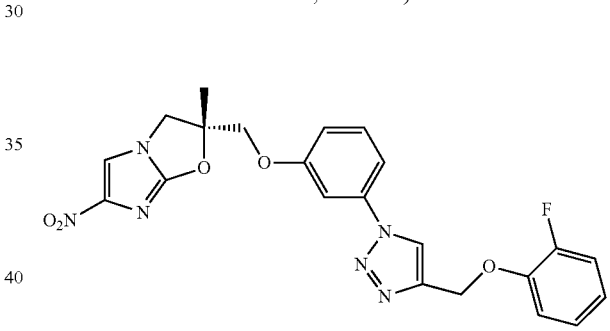

TLC (DCM: EtOAc 1:9): $R_f$=0.30; $^1$H NMR (400 MHz, CDCl$_3$): δ 1.82 (s, 3H), 4.09 (d, 1H, J=10.2 Hz), 4.19 (d, 1H, J=10.2 Hz), 4.36 (d, 1H, J=10.3 Hz), 4.53 (d, 1H, J=10.2 Hz), 5.29 (s, 2H), 6.93 (m, 1H), 7.05-7.15 (m, 3H), 7.22-7.27 (m, 4H), 7.59 (s, 1H), 8.05 (s, 1H); MS (ESI+): m\z 466.14.

(R)-2-{3-[4-(4-methylphenoxy)methyl)-1H-1,2,3-triazol-1-yl]phenoxymethyl}-2,3-dihydro-2-methyl-6-nitroimidazo[2,1-b]oxazole (compound IA37, Table 3, FIG. 12)

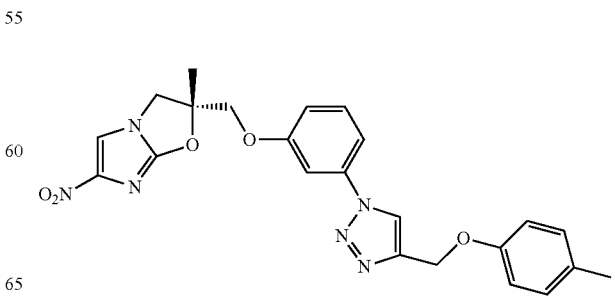

TLC (DCM: EtOAc 1:9): R$_f$=0.30; $^1$H NMR (400 MHz, CDCl$_3$): δ 1.82 (s, 3H), 2.12 (s, 3H), 4.07 (d, 1H, J=10.2 Hz), 4.16 (d, 1H, J=10.2 Hz), 4.34 (d, 1H, J=10.3 Hz), 4.51 (d, 1H, J=10.2 Hz), 5.25 (s, 2H), 6.93 (m, 1H), 7.05-7.15 (m, 3H), 7.22-7.27 (m, 4H), 7.60 (s, 1H), 8.05 (s, 1H); MS (ESI+): m\z 462.17.

(R)-2-{3-[4-(4-isopropylphenoxy)methyl)-1H-1,2,3-triazol-1-yl]phenoxymethyl}-2,3-dihydro-2-methyl-6-nitroimidazo[2,1-b]oxazole (compound IA38, Table 3, FIG. 12)

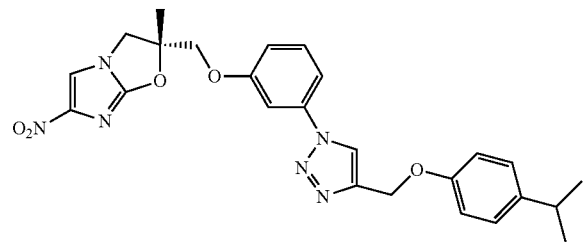 [SMILES: CC(C)c1ccc(OCc2cn(-c3cccc(OC[C@@]4(C)Cn5cc([N+](=O)[O-])nc5O4)c3)nn2)cc1]

TLC (DCM: EtOAc 1:9): R$_f$=0.40; $^1$H NMR (400 MHz, CDCl$_3$): δ 1.21 (d, 6H, J=8.82 Hz), 1.82 (s, 3H), 2.15 (s, 3H), 4.07 (d, 1H, J=10.2 Hz), 4.16 (d, 1H, J=10.2 Hz), 4.34 (d, 1H, J=10.3 Hz), 4.51 (d, 1H, J=10.2 Hz), 5.25 (s, 2H), 6.97 (m, 1H), 7.09-7.18 (m, 3H), 7.22-7.27 (m, 4H), 7.71 (s, 1H), 8.05 (s, 1H); MS (ESI+): m\z 462.17.

(R)-2-{2-[4-(4-trifluoromethoxyphenoxy)methyl)-1H-1,2,3-triazol-1-yl]phenoxymethyl}-2,3-dihydro-2-methyl-6-nitroimidazo[2,1-b]oxazole (compound IA39, Table 3, FIG. 12)

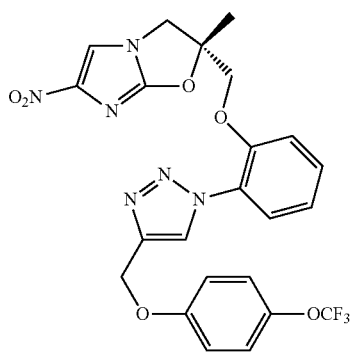 [SMILES: C[C@]1(COc2ccccc2-n2cc(COc3ccc(OC(F)(F)F)cc3)nn2)Cn2cc([N+](=O)[O-])nc2O1]

TLC (DCM: EtOAc 1:9): R$_f$=0.40; $^1$H NMR (400 MHz, CDCl$_3$): δ 1.67 (s, 3H), 3.87 (d, 1H, J=10.2 Hz), 4.09 (d, 1H, J=10.3 Hz), 4.34 (d, 1H, J=10.2 Hz), 4.38 (d, 1H, J=10.3 Hz), 5.16 (m, 2H), 7.03 (d, 2H, J=9.2 Hz), 7.09 (d, 1H, J=8.0 Hz), 7.18 (m, 3H), 7.45 (s, 1H), 7.49 (m, 2H), 7.73 (s, 1H), 8.05 (s, 1H); MS (ESI+): m\z 532.13.

(R)-2-{2-[4-(4-fluorophenoxy)methyl)-1H-1,2,3-triazol-1-yl]phenoxymethyl}-2,3-dihydro-2-methyl-6-nitroimidazo[2,1-b]oxazole (compound IA40, Table 3, FIG. 12)

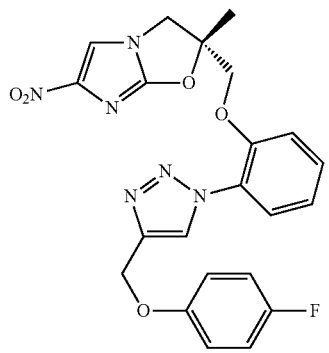 [SMILES: C[C@]1(COc2ccccc2-n2cc(COc3ccc(F)cc3)nn2)Cn2cc([N+](=O)[O-])nc2O1]

TLC (DCM: EtOAc 1:9): R$_f$=0.30; $^1$H NMR (400 MHz, CDCl$_3$): δ 1.67 (s, 3H), 3.88 (d, 1H, J=10.2 Hz), 4.09 (d, 1H, J=10.3 Hz), 4.36 (d, 1H, J=10.2 Hz), 4.39 (d, 1H, J=10.3 Hz), 5.19 (m, 2H), 7.03 (d, 2H, J=9.2 Hz), 7.09 (d, 1H, J=8.0 Hz), 7.18 (m, 3H), 7.47 (s, 1H), 7.51 (m, 2H), 7.73 (s, 1H), 8.06 (s, 1H); MS (ESI+): m\z 466.14.

(R)-2-{2-[4-(4-trifluoromethylphenoxy)methyl)-1H-1,2,3-triazol-1-yl]phenoxymethyl}-2,3-dihydro-2-methyl-6-nitroimidazo[2,1-b]oxazole (compound IA41, Table 3, FIG. 12)

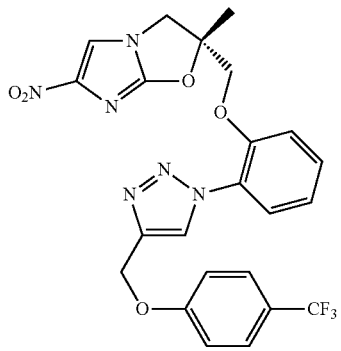 [SMILES: C[C@]1(COc2ccccc2-n2cc(COc3ccc(C(F)(F)F)cc3)nn2)Cn2cc([N+](=O)[O-])nc2O1]

TLC (DCM: EtOAc 1:9): R$_f$=0.40; $^1$H NMR (400 MHz, CDCl$_3$): δ 1.71 (s, 3H), 3.89 (d, 1H, J=10.2 Hz), 4.09 (d, 1H, J=10.3 Hz), 4.34 (d, 1H, J=10.2 Hz), 4.38 (d, 1H, J=10.3 Hz), 5.16 (m, 2H), 7.03 (d, 2H, J=9.2 Hz), 7.12 (d, 1H, J=8.0 Hz), 7.19 (m, 3H), 7.47 (s, 1H), 7.59 (m, 2H), 7.85 (s, 1H), 8.10 (s, 1H); MS (ESI+): m\z 516.43.

(R)-2-{2-[4-(2-fluorophenoxy)methyl)-1H-1,2,3-triazol-1-yl]phenoxymethyl}-2,3-dihydro-2-methyl-6-nitroimidazo[2,1-b]oxazole (compound IA42, Table 3, FIG. 12)

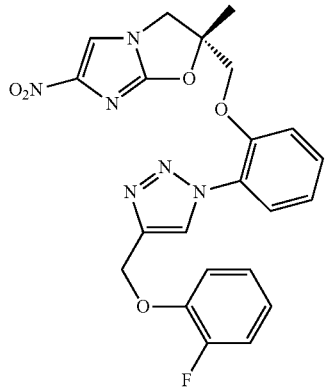 [SMILES: C[C@]1(COc2ccccc2-n2cc(COc3ccccc3F)nn2)Cn2cc([N+](=O)[O-])nc2O1]

TLC (DCM: EtOAc 1:9): R$_f$=0.30; $^1$H NMR (400 MHz, CDCl$_3$): δ 1.67 (s, 3H), 3.88 (d, 1H, J=10.2 Hz), 4.09 (d, 1H, J=10.3 Hz), 4.36 (d, 1H, J=10.2 Hz), 4.39 (d, 1H, J=10.3 Hz), 5.19 (m, 2H), 7.03 (m, 1H), 7.09 (d, 1H, J=8.0 Hz), 7.18 (m, 3H), 7.28 (m, 3H) 7.47 (s, 1H), 7.77 (s, 1H), 8.08 (s, 1H); MS (ESI+): m\z 466.14.

(R)-2-{4-[5-phenyl-1H-tetrazol-1-yl]phenoxymethyl}-2,3-dihydro-2-methyl-6-nitroimidazo[2,1-b]oxazole (compound IB1, Table 4, FIG. 14)

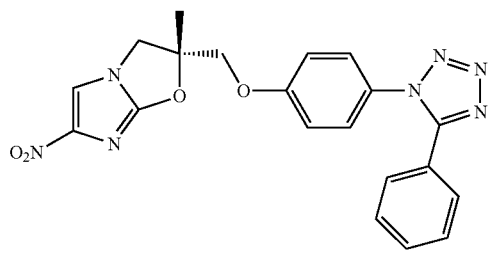 [SMILES: C[C@]1(COc2ccc(-n3nnnc3-c3ccccc3)cc2)Cn2cc([N+](=O)[O-])nc2O1]

TLC (DCM: EtOAc 1:9): R$_f$=0.30; $^1$H NMR (400 MHz, Acetone d$_6$): δ 1.83 (s, 3H), 4.39 (d, 1H, J=10.8 Hz), 4.50 (dd, 2H, J=21.1, 10.6 Hz), 4.69 (d, 1H, J=10.8 Hz), 6.95 (d, 2H, J=7.5 Hz), 7.41 (m, 1H), 7.45 (d, 2H, J=7.5 Hz), 7.51 (m, 2H), 7.79 (m, 2H), 9.08 (s, 1H); MS (ESI+): m\z 419.13.

(R)-2-{4-[5-(4-trifluoromethoxyphenyl)-1H-tetrazol-1-yl]phenoxymethyl}-2,3-dihydro-2-methyl-6-nitroimidazo[2,1-b]oxazole (compound IB2, Table 4, FIG. 14)

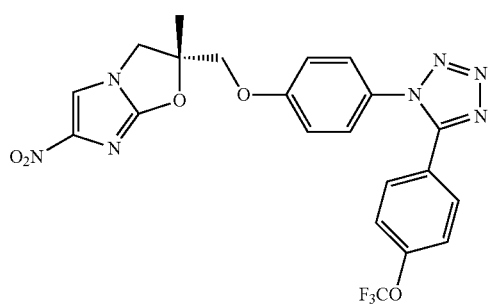 [SMILES: C[C@]1(COc2ccc(-n3nnnc3-c3ccc(OC(F)(F)F)cc3)cc2)Cn2cc([N+](=O)[O-])nc2O1]

TLC (DCM: EtOAc 1:9): R$_f$=0.40; $^1$H NMR (400 MHz, Acetone d$_6$): δ1.81 (s, 3H), 4.37 (d, 1H, J=10.8 Hz), 4.48 (dd, 2H, J=21.1, 10.6 Hz), 4.65 (d, 1H, J=10.8 Hz), 6.98 (d, 2H, J=7.8 Hz), 7.05 (d, 2H, J=8.12 Hz), 7.51 (d, 2H, J=7.8 Hz), 7.97 (d, 2H, J=8.12 Hz), 9.05 (s, 1H); MS (ESI+): m\z 503.12.

(R)-2-{4-[5-(4-methylphenyl)-1H-tetrazol-1-yl]phenoxymethyl}-2,3-dihydro-2-methyl-6-nitroimidazo[2,1-b]oxazole (compound IB3, Table 4, FIG. 14)

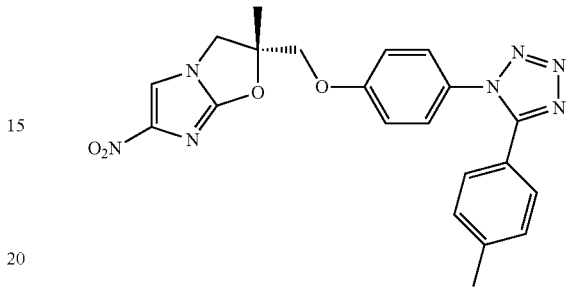

TLC (DCM: EtOAc 1:9): R$_f$=0.35; $^1$H NMR (400 MHz, Acetone d$_6$): δ1.83 (s, 3H), 2.30 (s, 3H), 4.39 (d, 1H, J=10.8 Hz), 4.49 (dd, 2H, J=21.1, 10.6 Hz), 4.66 (d, 1H, J=10.8 Hz), 6.99 (d, 2H, J=7.8 Hz), 7.29 (d, 2H, J=8.05 Hz), 7.51 (d, 2H, J=7.8 Hz), 9.07 (s, 1H); MS (ESI+): m\z 433.15.

(R)-2-{4-[5-(4-florophenyl)-1H-tetrazol-1-yl]phenoxymethyl}-2,3-dihydro-2-methyl-6-nitroimidazo[2,1-b]oxazole (compound IB4, Table 4, FIG. 14)

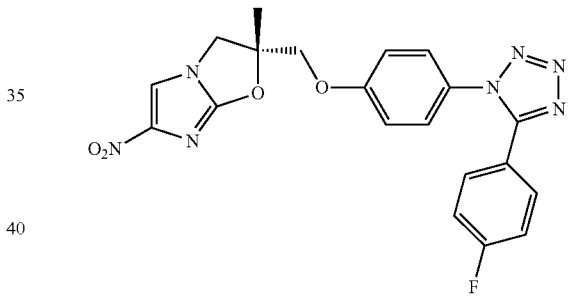

TLC (DCM: EtOAc 1:9): R$_f$=0.35; $^1$H NMR (400 MHz, Acetone d$_6$): δ1.83 (s, 3H), 4.39 (d, 1H, J=10.8 Hz), 4.48 (dd, 2H, J=21.1, 10.6 Hz), 4.65 (d, 1H, J=10.8 Hz), 6.98 (d, 2H, J=7.8 Hz), 7.05 (d, 2H, J=8.12 Hz), 7.51 (d, 2H, J=7.8 Hz), 7.97 (m, 2H), 9.05 (s, 1H); MS (ESI+): m\z 437.12.

(R)-2-{4-[5-(4-trifluoromethylphenyl)-1H-tetrazol-1-yl]phenoxymethyl}-2,3-dihydro-2-methyl-6-nitroimidazo[2,1-b]oxazole (compound IB5, Table 4, FIG. 14)

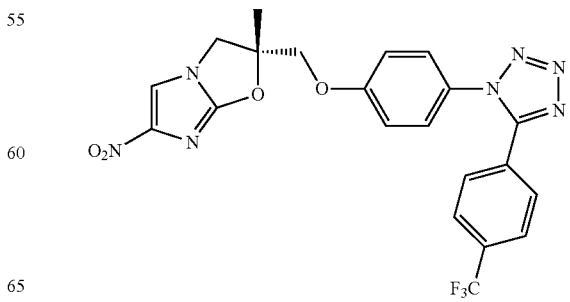

TLC (DCM: EtOAc 1:9): $R_f$=0.40; $^1$H NMR (400 MHz, Acetone $d_6$): δ1.81 (s, 3H), 4.37 (d, 1H, J=10.8 Hz), 4.48 (dd, 2H, J=21.1, 10.6 Hz), 4.65 (d, 1H, J=10.8 Hz), 6.99 (d, 2H, J=7.91 Hz), 7.53 (d, 2H, J=7.91 Hz), 7.68 (d, 2H, J=7.5 Hz), 8.37 (d, 2H, J=7.5 Hz), 9.05 (s, 1H); MS (ESI+): m\z 487.12.

(R)-2-{4-[5-(4-ethylphenyl)-1H-tetrazol-1-yl]phenoxymethyl}-2,3-dihydro-2-methyl-6-nitroimidazo[2,1-b]oxazole (compound IB6, Table 4, FIG. 14)

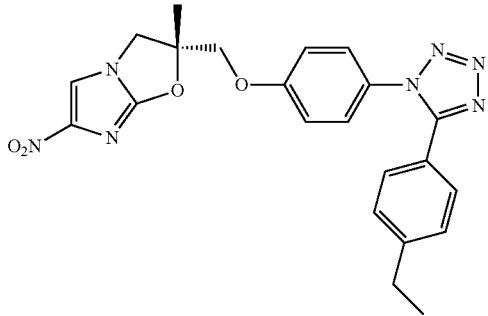 [SMILES: CCc1ccc(-c2nnnn2-c2ccc(OC[C@@]3(C)Cn4cc([N+](=O)[O-])nc4O3)cc2)cc1]

TLC (DCM: EtOAc 1:9): $R_f$=0.40; $^1$H NMR (400 MHz, Acetone $d_6$): δ1.21 (t, 3H, J=8.85 Hz), 1.83 (s, 3H), 2.28 (m, 2H), 4.39 (d, 1H, J=10.8 Hz), 4.49 (dd, 2H, J=21.1, 10.6 Hz), 4.66 (d, 1H, J=10.8 Hz), 6.99 (d, 2H, J=7.8 Hz), 7.29 (d, 2H, J=8.05 Hz), 7.51 (d, 2H, J=7.8 Hz), 9.07 (s, 1H); MS (ESI+): m\z 444.17.

(R)-2-{4-[5-(4-fluorophenoxy)-1H-tetrazol-1-yl]phenoxymethyl}-2,3-dihydro-2-methyl-6-nitroimidazo[2,1-b]oxazole (compound IB7, Table 4, FIG. 16)

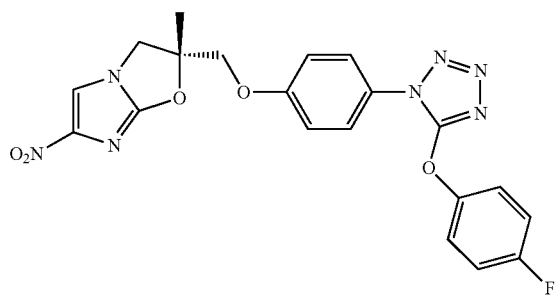 [SMILES: C[C@]1(COc2ccc(-n3nnnc3Oc3ccc(F)cc3)cc2)Cn2cc([N+](=O)[O-])nc2O1]

TLC (DCM: EtOAc 2:8): $R_f$=0.35; $^1$H NMR (400 MHz, Acetone $d_6$): δ 1.83 (s, 3H), 4.39 (d, 1H, J=10.8 Hz), 4.48 (dd, 2H, J=21.1, 10.6 Hz), 4.65 (d, 1H, J=10.8 Hz), 6.95 (d, 2H, J=7.18 Hz), 7.07 (d, 2H, J=7.82 Hz), 7.25 (d, 2H, J=7.82 Hz), 7.45 (d, 2H, J=7.18 Hz), 8.90 (s, 1H); MS (ESI+): m\z 453.12.

(R)-2-{4-[5-(4-trifluoromethylphenoxy)-1H-tetrazol-1-yl]phenoxymethyl}-2,3-dihydro-2-methyl-6-nitroimidazo[2,1-b]oxazole (compound IB8, Table 4, FIG. 16)

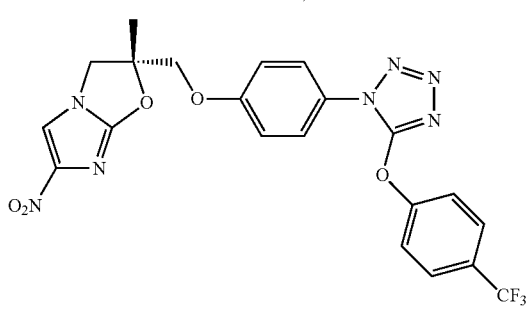 [SMILES: C[C@]1(COc2ccc(-n3nnnc3Oc3ccc(C(F)(F)F)cc3)cc2)Cn2cc([N+](=O)[O-])nc2O1]

TLC (DCM: EtOAc 2:8): $R_f$=0.40; $^1$H NMR (400 MHz, Acetone $d_6$): δ 1.85 (s, 3H), 4.39 (d, 1H, J=10.8 Hz), 4.48 (dd, 2H, J=21.1, 10.6 Hz), 4.65 (d, 1H, J=10.8 Hz), 6.90 (d, 2H, J=7.10 Hz), 7.14 (d, 2H, J=7.53 Hz), 7.45 (d, 2H, J=7.53 Hz), 7.48 (d, 2H, J=7.10 Hz), 8.90 (s, 1H); MS (ESI+): m\z 503.12.

(R)-2-{4-[5-(4-methylphenoxy)-1H-tetrazol-1-yl]phenoxymethyl}-2,3-dihydro-2-methyl-6-nitroimidazo[2,1-b]oxazole (compound IB9, Table 4, FIG. 16)

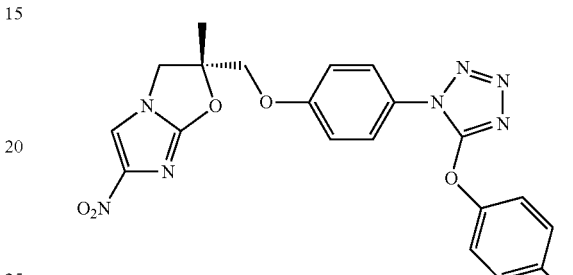

TLC (DCM: EtOAc 2:8): $R_f$=0.35; $^1$H NMR (400 MHz, Acetone $d_6$): δ 1.83 (s, 3H), 2.30 (s, 3H), 4.36 (d, 1H, J=10.8 Hz), 4.47 (dd, 2H, J=21.1, 10.6 Hz), 4.62 (d, 1H, J=10.8 Hz), 6.93 (d, 2H, J=7.10 Hz), 7.06 (d, 2H, J=7.35 Hz), 7.09 (d, 2H, J=7.35 Hz), 7.48 (d, 2H, J=7.10 Hz), 8.88 (s, 1H); MS (ESI+): m\z 449.14.

(R)-2-{4-[5-(4-trifluoromethoxyphenoxy)-1H-tetrazol-1-yl]phenoxymethyl}-2,3-dihydro-2-methyl-6-nitroimidazo[2,1-b]oxazole (compound IB10, Table 4, FIG. 16)

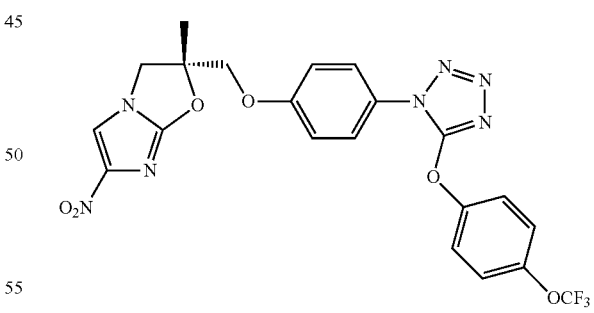

TLC (DCM: EtOAc 2:8): $R_f$=0.42; $^1$H NMR (400 MHz, Acetone $d_6$): δ 1.82 (s, 3H), 4.35 (d, 1H, J=10.8 Hz), 4.43 (dd, 2H, J=21.1, 10.6 Hz), 4.62 (d, 1H, J=10.8 Hz), 6.82 (d, 2H, J=7.65 Hz), 6.99 (d, 2H, J=7.10 Hz), 7.13 (d, 2H, J=7.65 Hz), 7.51 (d, 2H, J=7.10 Hz), 8.85 (s, 1H); MS (ESI+): m\z 519.11.

(R)-2-{4-[5-phenylisoxazol-3-yl]phenoxymethyl}-2,
3-dihydro-2-methyl-6nitroimidazo[2,1-b]oxazole
(compound IC1, Table 5, FIG. 18)

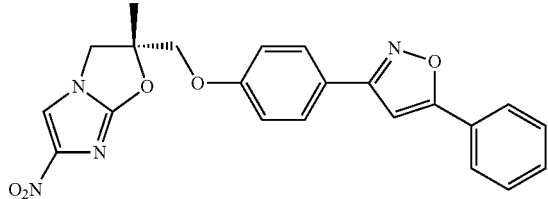 [SMILES: C[C@]1(COc2ccc(-c3cc(-c4ccccc4)on3)cc2)Cn2cc([N+](=O)[O-])nc2O1]

TLC (DCM: EtOAc 1:9): R$_f$=0.30; $^1$H NMR (400 MHz, Acetone d$_6$): δ1.82 (s, 3H), 4.07 (d, 1H, J=10.2 Hz), 4.16 (d, 1H, J=10.0 Hz), 4.31 (d, 1H, J=10.0 Hz), 4.52 (d, 1H, J=10.2 Hz), 6.78 (s, 1H), 6.95 (d, 2H, J=8.8 Hz), 7.46-7.51 (m, 3H), 7.58 (s, 1H), 7.83 (m, 4H); MS (ESI+): m\z 418.13

(R)-2-{4-[5-(2-fluorophenyl)isoxazol-3-yl]phenoxymethyl}-2,3-dihydro-2-methyl-6-nitroimidazo[2,14]oxazole (compound IC4, Table 5, FIG. 18)

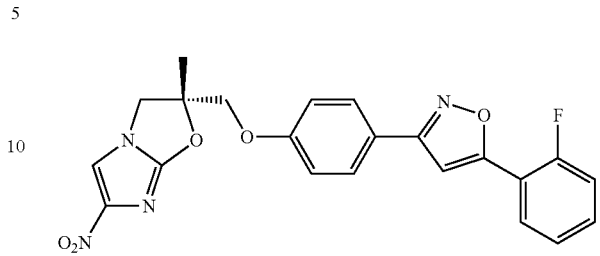

TLC (DCM: EtOAc 1:9): R$_f$=0.35; $^1$H NMR (400 MHz, Acetone d$_6$): δ1.80 (s, 3H), 4.32 (d, 1H, J=10.8 Hz), 4.40 (d, 1H, J=10.6 Hz), 4.45 (d, 1H, J=10.8 Hz), 4.62 (d, 1H, J=10.6 Hz), 7.05 (d, 2H, J=8.9 Hz), 7.19-7.29 (d, 2H, J=8.5 Hz), 7.86 (m, 3H), 7.83 (s, 1H), 7.98 (m, 1H); MS (ESI+): m\z 436.12.

(R)-2-{4-[5-(4-ethylphenyl)isoxazol-3-yl]phenoxymethyl}-2,3-dihydro-2-methyl-6-nitroimidazo[2,1-b]oxazole (compound IC2, Table 5, FIG. 18)

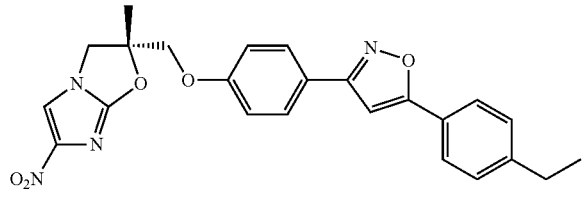 [SMILES: CCc1ccc(-c2cc(-c3ccc(OC[C@@]4(C)Cn5cc([N+](=O)[O-])nc5O4)cc3)no2)cc1]

TLC (DCM: EtOAc 1:9): R$_f$=0.30; $^1$H NMR (400 MHz, Acetone d$_6$): δ1.21 (m, 3H), 1.84 (s, 3H), 2.40 (m, 2H), 4.36 (d, 1H, J=10.8 Hz), 4.44 (d, 1H, J=10.6 Hz), 4.48 (d, 1H, J=10.8 Hz), 4.66 (d, 1H, J=10.6 Hz), 7.09 (d, 2H, J=8.9 Hz), 7.24 (s, 1H), 7.37 (d, 2H, J=8.5 Hz), 7.80 (d, 2H, J=8.5 Hz), 7.88 (d, 2H, J=8.9 Hz), 7.90 (s, 1H); MS (ESI+): m\z 446.46.

(R)-2-{4-[5-(4-trifluoromethylphenyl)isoxazol-3-yl]phenoxymethyl}-2,3-dihydro-2-methyl-6-nitroimidazo[2,1-b]oxazole (compound 105, Table 5, FIG. 18)

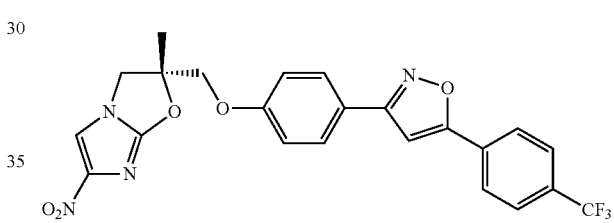

TLC (DCM: EtOAc 1:9): R$_f$=0.40; $^1$H NMR (400 MHz, Acetone d$_6$): δ1.89 (s, 3H), 4.38 (d, 1H, J=10.8 Hz), 4.47 (d, 1H, J=10.6 Hz), 4.49 (d, 1H, J=10.8 Hz), 4.68 (d, 1H, J=10.6 Hz), 7.09 (d, 2H, J=8.9 Hz), 7.26 (s, 1H), 7.39 (d, 2H, J=8.5 Hz), 7.83 (d, 2H, J=8.5 Hz), 7.89, (d, 2H, J=8.9 Hz), 7.92 (s, 1H); MS (ESI+): m\z 486.12.

(R)-2-{4-[5-(2,4-difluorophenyl)isoxazol-3-yl]phenoxymethyl}-2,3-dihydro-2-methyl-6-nitroimidazo[2,1-b]oxazole (compound IC3, Table 5, FIG. 18)

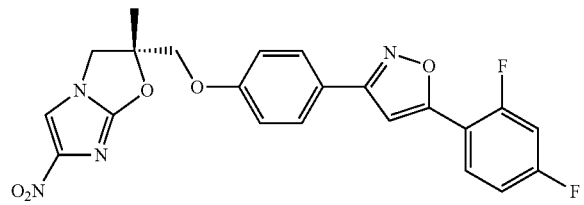 [SMILES: C[C@]1(COc2ccc(-c3cc(-c4ccc(F)cc4F)on3)cc2)Cn2cc([N+](=O)[O-])nc2O1]

TLC (DCM: EtOAc 1:9): R$_f$=0.40; $^1$H NMR (400 MHz, Acetone d$_6$): δ1.78 (s, 3H), 4.30 (d, 1H, J=10.8 Hz), 4.38 (d, 1H, J=10.6 Hz), 4.42 (d, 1H, J=10.8 Hz), 4.60 (d, 1H, J=10.6 Hz), 7.03 (d, 2H, J=8.9 Hz), 7.18 (m, 1H), 7.19-7.29 (d, 2H, J=8.5 Hz), 7.86 (d, 2H, J=4.7 Hz), 7.89 (s, 1H), 8.03 (m, 1H); MS (ESI+): m\z 454.14.

(R)-2-{4-[5-(4-methylphenyl)isoxazol-3-yl]phenoxymethyl}-2,3-dihydro-2-methyl-6-nitroimidazo[2,1-b]oxazole (compound 106, Table 5, FIG. 18)

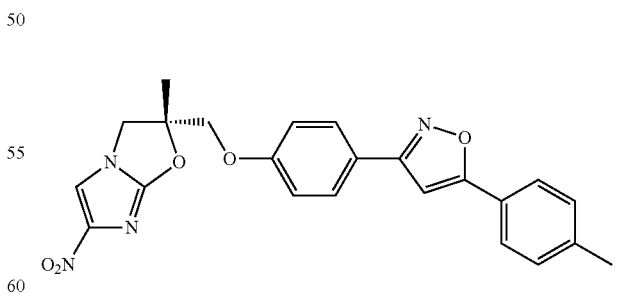

TLC (DCM: EtOAc 1:9): R$_f$=0.30; $^1$H NMR (400 MHz, Acetone d$_6$): δ1.84 (s, 3H), 2.40 (s, 2H), 4.36 (d, 1H, J=10.8 Hz), 4.44 (d, 1H, J=10.6 Hz), 4.48 (d, 1H, J=10.8 Hz), 4.66 (d, 1H, J=10.6 Hz), 7.09 (d, 2H, J=8.9 Hz), 7.24 (s, 1H), 7.37 (d, 2H, J=8.5 Hz), 7.80 (d, 2H, J=8.5 Hz), 7.88 (d, 2H, J=8.9 Hz), 7.90 (s, 1H); MS (ESI+): m\z 432.14.

(R)-2-{4-[5-(4-methoxyphenyl)isoxazol-3-yl]phenoxymethyl}-2,3-dihydro-2-methyl-6-nitroimidazo[2,1-b]oxazole (compound IC7, Table 5, FIG. 18)

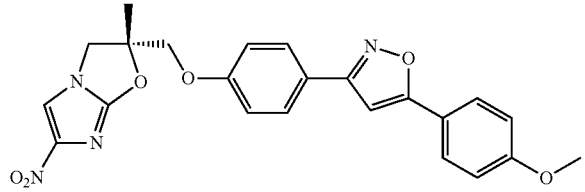

TLC (DCM: EtOAc 1:9): $R_f$=0.30; $^1$H NMR (400 MHz, Acetone $d_6$): δ 1.85 (s, 3H), 3.89 (s, 3H), 4.38 (d, 1H, J=10.8 Hz), 4.44 (d, 1H, J=10.6 Hz), 4.48 (d, 1H, J=10.8 Hz), 4.66 (d, 1H, J=10.6 Hz), 7.10 (m, 4H), 7.17 (s, 1H), 7.88 (m, 4H), 8.02 (s, 1H); MS (ESI+): m\z 448.14.

(R)-2-{4-[5-(3-fluorophenyl)isoxazol-3-yl]phenoxymethyl}-2,3-dihydro-2-methyl-6-nitroimidazo[2,1-b]oxazole (compound IC8, Table 5, FIG. 18)

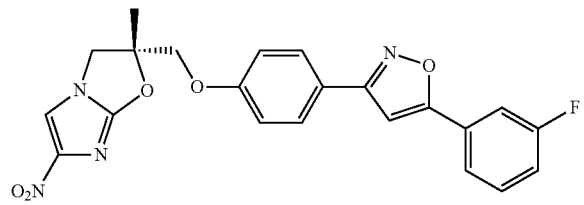 [SMILES: C[C@]1(COc2ccc(-c3cc(-c4cccc(F)c4)on3)cc2)Cn2cc([N+](=O)[O-])nc2O1]

TLC (DCM: EtOAc 1:9): $R_f$=0.35; $^1$H NMR (400 MHz, Acetone $d_6$): δ 1.80 (s, 3H), 4.32 (d, 1H, J=10.8 Hz), 4.40 (d, 1H, J=10.6 Hz), 4.45 (d, 1H, J=10.8 Hz), 4.62 (d, 1H, J=10.6 Hz), 7.05 (d, 2H, J=8.9 Hz), 7.17 (s, 1H), 7.19-7.29 (d, 2H, J=8.5 Hz), 7.86 (m, 2H), 7.83 (s, 1H), 7.98 (m, 2H); MS (ESI+): m\z 436.12.

(R)-2-{4-[5-(pyridin-2-yl)isoxazol-3-yl]phenoxymethyl}-2,3-dihydro-2-methyl-6-nitroimidazo[2,1-b]oxazole (compound IC9, Table 5, FIG. 18)

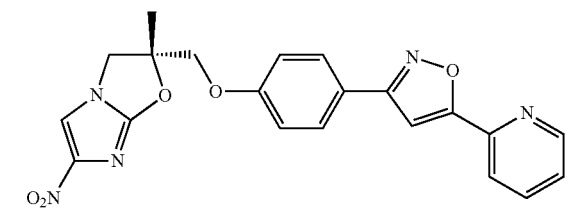

TLC (DCM: EtOAc 1:9): $R_f$=0.35; $^1$H NMR (400 MHz, Acetone $d_6$): δ 1.82 (s, 3H), 4.34 (d, 1H, J=10.8 Hz), 4.43 (d, 1H, J=10.6 Hz), 4.47 (d, 1H, J=10.8 Hz), 4.64 (d, 1H, J=10.6 Hz), 7.12 (d, 2H, J=8.9 Hz), 7.19 (s, 1H), 7.29 (d, 2H, J=8.5 Hz), 7.86 (m, 3H), 7.89 (s, 1H), 8.40 (m, 1H); MS (ESI+): m\z 419.12.

(R)-2-{4-[5-(4-trifluoromethoxyphenyl)isoxazol-3-yl]phenoxymethyl}-2,3-dihydro-2-methyl-6-nitroimidazo[2,1-b]oxazole (compound IC10, Table 5, FIG. 18)

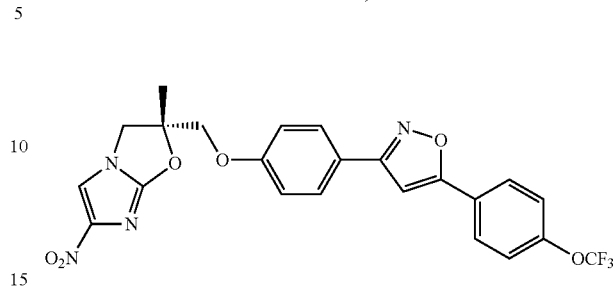

TLC (DCM: EtOAc 1:9): $R_f$=0.40; $^1$H NMR (400 MHz, Acetone $d_6$): δ1.83 (s, 3H), 4.33 (d, 1H, J=10.8 Hz), 4.42 (d, 1H, J=10.6 Hz), 4.44 (d, 1H, J=10.8 Hz), 4.64 (d, 1H, J=10.6 Hz), 7.05 (d, 2H, J=8.9 Hz), 7.22 (s, 1H), 7.32 (d, 2H, J=8.5 Hz), 7.80 (d, 2H, J=8.5 Hz), 7.85 (d, 2H, J=8.9 Hz), 7.90 (s, 1H); MS (ESI+): m\z 502.12.

(R)-2-{4-[5-pentylisoxazol-3-yl]phenoxymethyl}-2,3-dihydro-2-methyl-6-nitroimidazo[2,1-b]oxazole (compound IC11, Table 5 FIG. 18)

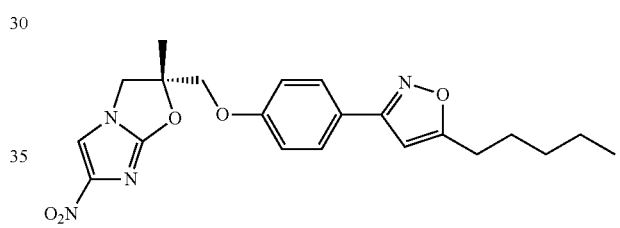

TLC (DCM: EtOAc 1:9): $R_f$=0.45; $^1$H NMR (400 MHz, Acetone $d_6$): δ0.91 (m, 3H), 1.15 (m, 2H), 1.21 (m, 4H), 1.89 (s, 3H), 2.25 (t, 2H), 4.39 (d, 1H, J=10.8 Hz), 4.50 (dd, 2H, J=21.1, 10.6 Hz), 4.69 (d, 1H, J=10.8 Hz), 6.95 (d, 2H, J=7.6 Hz), 7.05 (s, 1H), 7.25 (d, 2H, J=7.6 Hz), 7.85 (s, 1H); MS (ESI+): m\z 412.19.

(R)-2-{4-[5-heptylisoxazol-3-yl]phenoxymethyl}-2,3-dihydro-2-methyl-6-nitroimidazo[2,1-b]oxazole (compound IC12, Table 5, FIG. 18)

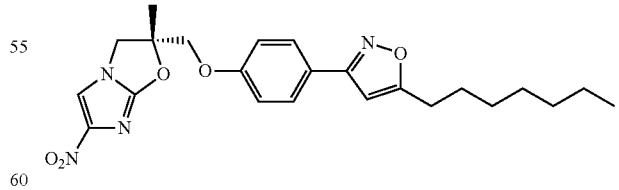

TLC (DCM: EtOAc 1:9): $R_f$=0.45; $^1$H NMR (400 MHz, Acetone $d_6$): δ0.91 (m, 3H), 1.15 (m, 2H), 1.21-1.24 (m, 8H), 1.89 (s, 3H), 2.25 (t, 2H), 4.39 (d, 1H, J=10.8 Hz), 4.50 (dd, 2H, J=21.1, 10.6 Hz), 4.69 (d, 1H, J=10.8 Hz), 6.96 (d, 2H, J=7.6 Hz), 7.07 (s, 1H), 7.26 (d, 2H, J=7.6 Hz), 7.83 (s, 1H); MS (ESI+): m\z 440.21.

(R)-2-{4-[5-(4-trifluoromethoxyphenoxymethyl)isoxazol-3-yl]phenoxymethyl}-2,3-dihydro-2-methyl-6-nitroimidazo[2,1-b]oxazole (compound IC13, Table 5, FIG. 20)

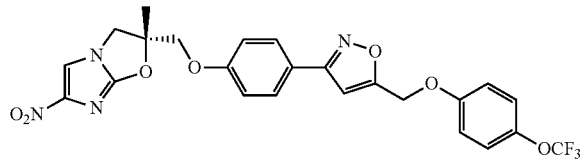 [SMILES: C[C@]1(COc2ccc(-c3cc(COc4ccc(OC(F)(F)F)cc4)on3)cc2)Cn2cc([N+](=O)[O-])nc2O1]

TLC (DCM: EtOAc 1:9): $R_f$=0.40; $^1$H NMR (400 MHz, CDCl$_3$): δ 1.81 (s, 3H), 4.06 (d, 1H, J=10.2 Hz), 4.14 (d, 1H, J=10.1 Hz), 4.29 (d, 1H, J=10.1 Hz), 4.51 (d, 1H, J=10.2 Hz), 5.18 (s, 2H), 6.60 (s, 1H), 6.92 (d, 2H, J=8.9 Hz), 6.98 (d, 2H, J=9.2 Hz), 7.18 (d, 2H, J=9.2 Hz), 7.56 (s, 1H), 7.74 (d, 2H, J=8.9 Hz); MS (ESI+): m\z 532.12.

(R)-2-{4-[5-(4-fluorophenoxymethyl)isoxazol-3-yl]phenoxymethyl}-2,3-dihydro-2-methyl-6-nitroimidazo[2,1-b]oxazole (compound IC14, Table 5, FIG. 20)

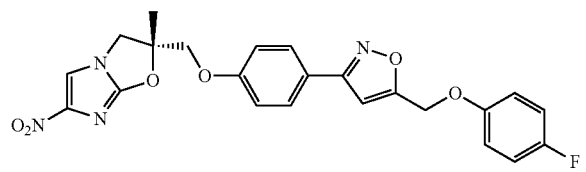 [SMILES: C[C@]1(COc2ccc(-c3cc(COc4ccc(F)cc4)on3)cc2)Cn2cc([N+](=O)[O-])nc2O1]

TLC (DCM: EtOAc 1:9): $R_f$=0.30; $^1$H NMR (400 MHz, CDCl$_3$): δ 1.81 (s, 3H), 4.06 (d, 1H, J=10.2 Hz), 4.14 (d, 1H, J=10.1 Hz), 4.29 (d, 1H, J=10.1 Hz), 4.51 (d, 1H, J=10.2 Hz), 5.16 (s, 2H), 6.58 (s, 1H), 6.90-6.95 (m, 4H), 7.01 (m, 2H), 7.57 (s, 1H), 7.74 (d, 2H, J=8.8 Hz); MS (ESI+): m\z 466.13.

(R)-2-{4-[5-(4-trifluoromethylphenoxymethyl)isoxazol-3-yl]phenoxymethyl}-2,3-dihydro-2-methyl-6-nitroimidazo[2,1-]oxazole (compound IC15, Table 5, FIG. 20)

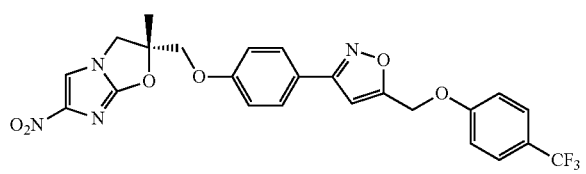 [SMILES: C[C@]1(COc2ccc(-c3cc(COc4ccc(C(F)(F)F)cc4)on3)cc2)Cn2cc([N+](=O)[O-])nc2O1]

TLC (DCM: EtOAc 1:9): $R_f$=0.40; $^1$H NMR (400 MHz, CDCl$_3$): δ 1.81 (s, 3H), 4.06 (d, 1H, J=10.2 Hz), 4.14 (d, 1H, J=10.1 Hz), 4.29 (d, 1H, J=10.1 Hz), 4.51 (d, 1H, J=10.2 Hz), 5.24 (s, 2H), 6.61 (s, 1H), 6.92 (d, 2H, J=8.9 Hz), 7.06 (d, 2H, J=8.6 Hz), 7.57 (s, 1H), 7.59 (d, 2H, J=8.6 Hz), 7.75 (d, 2H, J=8.9 Hz); MS (ESI+): m\z 516.13.

(R)-2-{4-[5-(2-fluorophenoxymethyl)isoxazol-3-yl]phenoxymethyl}-2,3-dihydro-2-methyl-6-nitroimidazo[2,1-b]oxazole (compound IC16, Table 5, FIG. 20)

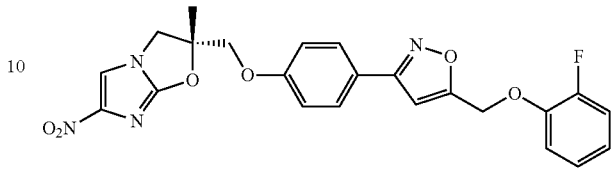

TLC (DCM: EtOAc 1:9): $R_f$=0.30; $^1$H NMR (400 MHz, CDCl$_3$): δ 1.81 (s, 3H), 4.06 (d, 1H, J=10.2 Hz), 4.14 (d, 1H, J=10.1 Hz), 4.29 (d, 1H, J=10.1 Hz), 4.51 (d, 1H, J=10.2 Hz), 5.26 (s, 2H), 6.63 (s, 1H), 6.92 (d, 2H, J=8.8 Hz), 6.98 (m, 1H), 7.02-7.09 (m, 2H), 7.12 (m, 1H), 7.57 (s, 1H), 7.75 (d, 2H, J=8.8 Hz); MS (ESI+): m\z 466.13.

(R)-2-{4-[5-(4-methylphenoxymethyl)isoxazol-3-yl]phenoxymethyl}-2,3-dihydro-2-methyl-6-nitroimidazo[2,1-b]oxazole (compound IC17, Table 5, FIG. 20)

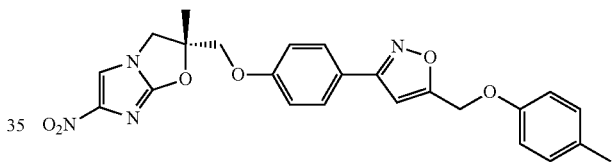

TLC (DCM: EtOAc 1:9): $R_f$=0.30; $^1$H NMR (400 MHz, CDCl$_3$): δ 1.83 (s, 3H), 2.32 (s, 3H), 4.08 (d, 1H, J=10.3 Hz), 4.15 (d, 1H, J=10.1 Hz), 4.31 (d, 1H, J=10.1 Hz), 4.53 (d, 1H, J=10.3 Hz), 5.19 (s, 2H), 6.60 (s, 1H), 6.92 (m, 4H), 7.13 (d, 2H, J=7.8 Hz), 7.59 (s, 1H), 7.76 (d, 2H, J=8.8 Hz); MS (ESI+): m\z 462.15.

(R)-2-{4-[5-(4-isopropylphenoxymethyl)isoxazol-3-yl]phenoxymethyl}-2,3-dihydro-2-methyl-6-nitroimidazo[2,1-b]oxazole (compound IC18, Table 5, FIG. 20)

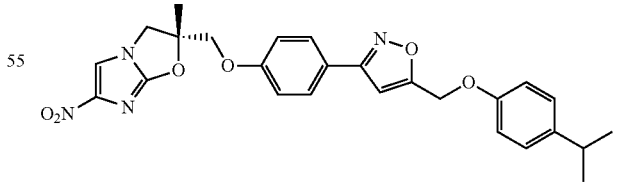

TLC (DCM: EtOAc 1:9): $R_f$=0.40; $^1$H NMR (400 MHz, CDCl$_3$): δ 1.25 (d, 6H, J=6.9 Hz), 1.83 (s, 3H), 2.89 (m, 1H), 4.09 (d, 1H, J=10.3 Hz), 4.15 (d, 1H, J=10.1 Hz), 4.30 (d, 1H, J=10.1 Hz), 4.53 (d, 1H, J=10.3 Hz), 5.18 (s, 2H), 6.61 (s, 1H), 6.93 (m, 4H), 7.19 (d, 2H, J=8.0 Hz), 7.58 (s, 1H), 7.75 (d, 2H, J=7.7 Hz); MS (ESI+): m\z 490.19.

(R)-2-{4-[5-(4-ethylphenoxymethyl)isoxazol-3-yl]phenoxymethyl}-2,3-dihydro-2-methyl-6-nitroimidazo[2,1-b]oxazole (compound IC19, Table 5, FIG. 20)

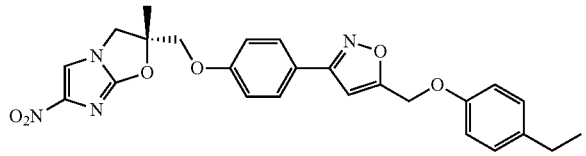 [SMILES: CCc1ccc(OCc2cc(-c3ccc(OC[C@@]4(C)Cn5cc([N+](=O)[O-])nc5O4)cc3)no2)cc1]

TLC (DCM: EtOAc 1:9): R$_f$=0.40; $^1$H NMR (400 MHz, CDCl$_3$): δ 1.23 (m, 3H), 1.83 (s, 3H), 2.85 (m, 2H), 4.09 (d, 1H, J=10.3 Hz), 4.15 (d, 1H, J=10.1 Hz), 4.30 (d, 1H, J=10.1 Hz), 4.53 (d, 1H, J=10.3 Hz), 5.18 (s, 2H), 6.61 (s, 1H), 6.93 (m, 4H), 7.19 (d, 2H, J=8.0 Hz), 7.58 (s, 1H), 7.75 (d, 2H, J=7.7 Hz); MS (ESI+): m\z 476.17.

(R)-2-{4-[5-(4-sec-butylphenoxymethyl)isoxazol-3-yl]phenoxymethyl}-2,3-dihydro-2-methyl-6-nitroimidazo[2,1-b]oxazole (compound IC20, Table 5, FIG. 20)

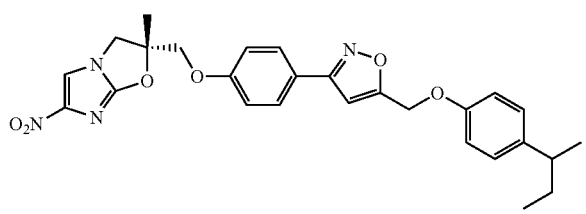 [SMILES: CCC(C)c1ccc(OCc2cc(-c3ccc(OC[C@@]4(C)Cn5cc([N+](=O)[O-])nc5O4)cc3)no2)cc1]

TLC (DCM: EtOAc 1:9): R$_f$=0.40; $^1$H NMR (400 MHz, CDCl$_3$): δ 1.11 (m, 3H), 1.22 (m, 3H), 1.28 (m, 2H), 1.82 (s, 3H), 2.89 (m, 1H), 4.09 (d, 1H, J=10.3 Hz), 4.15 (d, 1H, J=10.1 Hz), 4.30 (d, 1H, J=10.1 Hz), 4.53 (d, 1H, J=10.3 Hz), 5.18 (s, 2H), 6.61 (s, 1H), 6.93 (m, 4H), 7.19 (d, 2H, J=8.0 Hz), 7.58 (s, 1H), 7.75 (d, 2H, J=7.7 Hz); MS (ESI+): m\z 504.20.

(R)-2-{4-[5-(phenoxymethyl)isoxazol-3-yl]phenoxymethyl}-2,3-dihydro-2-methyl-6-nitroimidazo[2,1-b]oxazole (compound IC21, Table 5, FIG. 20)

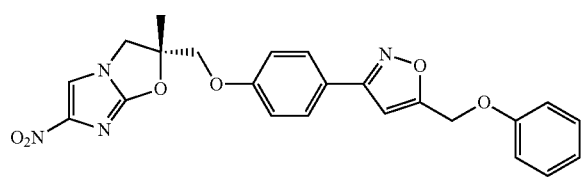 [SMILES: C[C@]1(COc2ccc(-c3cc(COc4ccccc4)on3)cc2)Cn2cc([N+](=O)[O-])nc2O1]

TLC (DCM: EtOAc 1:9): R$_f$=0.30; $^1$H NMR (400 MHz, CDCl$_3$): δ 1.81 (s, 3H), 4.06 (d, 1H, J=10.2 Hz), 4.14 (d, 1H, J=10.1 Hz), 4.29 (d, 1H, J=10.1 Hz), 4.51 (d, 1H, J=10.2 Hz), 5.26 (s, 2H), 6.78 (s, 1H), 6.95 (d, 2H, J=8.8 Hz), 7.51-7.46 (m, 3H), 7.58 (s, 1H), 7.83 (m, 4H); MS (ESI+): m\z 448.14.

(R)-2-{4-[5-(2,4-difluorophenoxymethyl)isoxazol-3-yl]phenoxymethyl}-2,3-dihydro-2-methyl-6-nitroimidazo[2,1-b]oxazole (compound IC22, Table 5, FIG. 20)

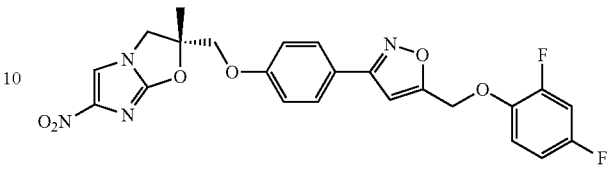

TLC (DCM: EtOAc 1:9): R$_f$=0.40; $^1$H NMR (400 MHz, CDCl$_3$): δ 1.81 (s, 3H), 4.06 (d, 1H, J=10.2 Hz), 4.14 (d, 1H, J=10.1 Hz), 4.29 (d, 1H, J=10.1 Hz), 4.51 (d, 1H, J=10.2 Hz), 5.26 (s, 2H), 6.63 (s, 1H), 6.92 (d, 2H, J=8.8 Hz), 7.02-7.09 (m, 2H), 7.57 (s, 1H), 7.75 (d, 2H, J=8.8 Hz), 7.89 (m, 1H); MS (ESI+): m\z 484.12.

(R)-1-(4-fluorophenyl)-3-{4-(2-methyl-6-nitro-2,3-dihydroimidazo[2,1-b]oxazol-2-yl)methoxyphenyl}urea (compound IIA1, Table 6, FIG. 22)

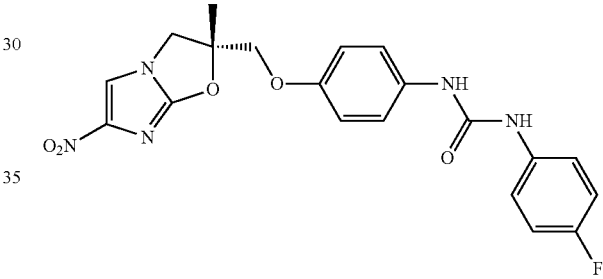

TLC (DCM: EtOAc 2:8): R$_f$=0.30; $^1$H NMR (400 MHz, Acetone d$_6$): δ1.80 (s, 3H), 4.32 (m, 3H), 4.62 (d, 1H, J=10.8 Hz), 6.87 (d, 2H, J=9.0 Hz), 7.23 (d, 2H, J=8.4 Hz), 7.44 (d, 2H, J=9.1 Hz), 7.68 (m, 2H), 7.90 (s, 1H), 8.11 (s, 1H), 8.34 (s, 1H); MS (ESI+): m\z 493.12.

(R)-1-(4-ethylphenyl)-3-{4-(2-methyl-6-nitro-2,3-dihydroimidazo[2,1-b]oxazol-2-yl)methoxyphenyl}urea (compound IIA2, Table 6, FIG. 22):

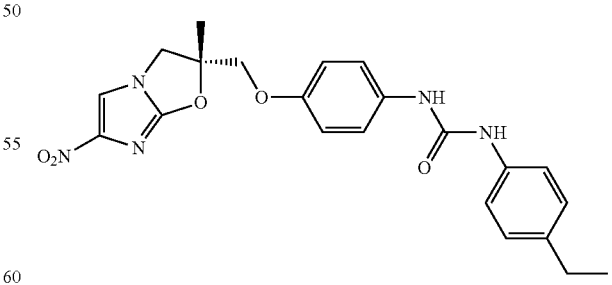

TLC (DCM: EtOAc 2:8): R$_f$=0.30; $^1$H NMR (400 MHz, Acetone d$_6$): δ 1.21 (t, 3H, J=8.85 Hz), 1.80 (s, 3H), 2.28 (m, 2H), 4.30 (m, 3H), 4.62 (d, 1H, J=10.8 Hz), 6.87 (d, 2H, J=9.0 Hz), 7.23 (d, 2H, J=8.4 Hz), 7.44 (d, 2H, J=9.1 Hz), 7.64 (d, 2H, J=9.1 Hz), 7.90 (s, 1H), 8.11 (s, 1H), 8.34 (s, 1H); MS (ESI+): m\z 437.17.

(R)-1-(4-trifluoromethylphenyl)-3-{4-(2-methyl-6-nitro-2,3-dihydroimidazo[2,1-b]oxazol-2-yl)methoxyphenyl}urea (compound IIA3, Table 6, FIG. 22)

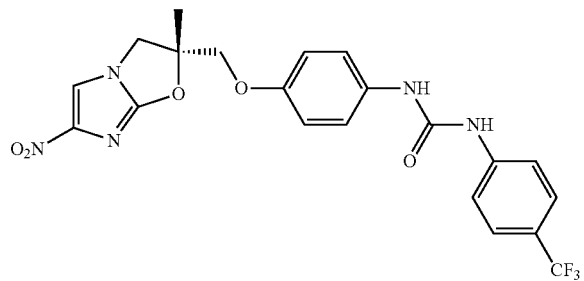

TLC (DCM: EtOAc 2:8): $R_f$=0.40; $^1$H NMR (400 MHz, Acetone $d_6$): δ 1.81 (s, 3H), 4.34 (m, 3H), 4.65 (d, 1H, J=10.8 Hz), 6.89 (d, 2H, J=9.0 Hz), 7.25 (d, 2H, J=8.4 Hz), 7.45 (d, 2H, J=9.1 Hz), 7.68 (d, 2H, J=9.1 Hz), 7.90 (s, 1H), 8.11 (s, 1H), 8.34 (s, 1H); MS (ESI+): m\z 477.13.

(R)-1-(4-methylphenyl)-3-{4-(2-methyl-6-nitro-2,3-dihydroimidazo[2,1-b]oxazol-2-yl)methoxyphenyl}urea (compound IIA4, Table 6, FIG. 22)

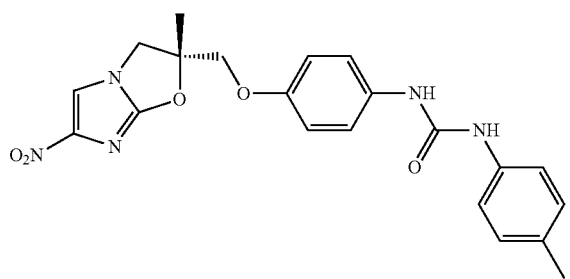

TLC (DCM: EtOAc 2:8): $R_f$=0.40; $^1$H NMR (400 MHz, Acetone $d_6$): δ1.81 (s, 3H), 2.38 (s, 3H), 4.32 (m, 3H), 4.62 (d, 1H, J=10.8 Hz), 6.85 (d, 2H, J=9.0 Hz), 7.25 (d, 2H, J=8.4 Hz), 7.47 (d, 2H, J=9.1 Hz), 7.65 (d, 2H, J=9.1 Hz), 7.90 (s, 1H), 8.10 (s, 1H), 8.32 (s, 1H); MS (ESI+): m\z 423.15.

(R)-1-(4-methoxyphenyl)-3-{4-(2-methyl-6-nitro-2,3-dihydroimidazo[2,1-b]oxazol-2-yl)methoxyphenyl}urea (compound IIA5, Table 6, FIG. 22)

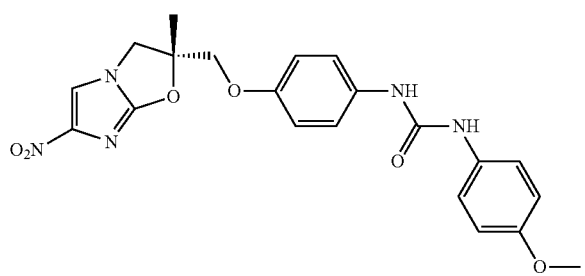

TLC (DCM: EtOAc 2:8): $R_f$=0.30; $^1$H NMR (400 MHz, Acetone $d_6$): δ1.82 (s, 3H), 3.76 (s, 3H), 4.33 (m, 3H), 4.62 (d, 1H, J=10.7 Hz), 6.86 (m, 4H), 7.44 (m, 4H), 7.91 (s, 1H), 8.03 (s, 2H); MS (ESI+): m\z 439.15.

(R)-1-(4-trifluoromethoxyphenyl)-3-{4-(2-methyl-6-nitro-2,3-dihydroimidazo[2,1-b]oxazol-2-yl)methoxyphenyl}urea (compound IIA6, Table 6, FIG. 22)

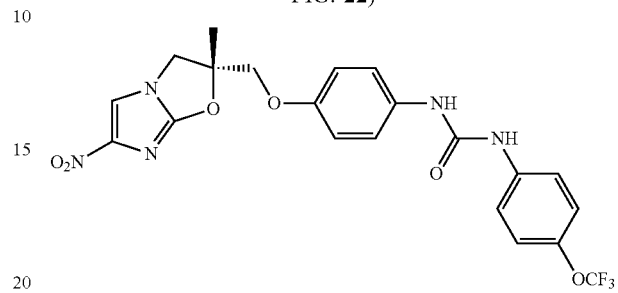

TLC (DCM: EtOAc 2:8): $R_f$=0.40; $^1$H NMR (400 MHz, Acetone $d_6$): δ1.80 (s, 3H), 4.32 (m, 3H), 4.62 (d, 1H, J=10.8 Hz), 6.87 (d, 2H, J=9.0 Hz), 7.23 (d, 2H, J=8.4 Hz), 7.44 (d, 2H, J=9.1 Hz), 7.64 (d, 2H, J=9.1 Hz), 7.90 (s, 1H), 8.11 (s, 1H), 8.34 (s, 1H); MS (ESI+): m\z 493.12.

(R)-1-(4-methoxyphenyl)-3-{4-(2-methyl-6-nitro-2,3-dihydroimidazo[2,1-b]oxazol-2-yl)methoxyphenyl}thiourea (compound IIA7, Table 6, FIG. 22)

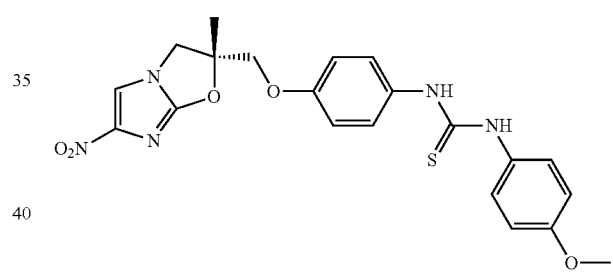

TLC (DCM: EtOAc 2:8): $R_f$=0.30; $^1$H NMR (400 MHz, Acetone $d_6$): δ 1.80 (s, 3H), 3.73 (s, 3H), 4.33 (m, 3H), 4.60 (d, 1H, J=10.7 Hz), 6.83 (m, 4H), 7.40 (m, 4H), 7.89 (s, 1H), 8.00 (s, 2H); MS (ESI+): m\z 455.13.

(R)-1-(4-trifluoromethoxyphenyl)-3-{4-(2-methyl-6-nitro-2,3-dihydroimidazo[2,1-b]oxazol-2-yl)methoxyphenyl}thiourea (compound IIA8, Table 6, FIG. 22)

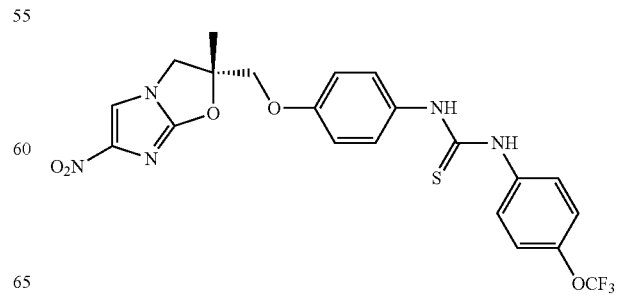

TLC (DCM: EtOAc 2:8): R$_f$=0.40; $^1$H NMR (400 MHz, Acetone d$_6$): δ 1.80 (s, 3H), 4.32 (m, 3H), 4.62 (d, 1H, J=10.8 Hz), 6.87 (d, 2H, J=9.0 Hz), 7.23 (d, 2H, J=8.4 Hz), 7.44 (d, 2H, J=9.1 Hz), 7.64 (d, 2H, J=9.1 Hz), 7.90 (s, 1H), 8.11 (s, 1H), 8.34 (s, 1H); MS (ESI+): m\z 509.10.

(R)-1-(4-fluorophenyl)-3-{4-(2-methyl-6-nitro-2,3-dihydroimidazo[2,1-b]oxazol-2-yl)methoxyphenyl}thiourea (compound IIA9, Table 6, FIG. 22)

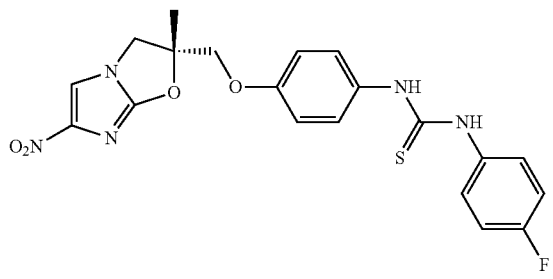

TLC (DCM: EtOAc 2:8): R$_f$=0.30; $^1$H NMR (400 MHz, Acetone d$_6$): δ1.80 (s, 3H), 4.30 (m, 3H), 4.60 (d, 1H, J=10.8 Hz), 6.85 (d, 2H, J=9.0 Hz), 7.22 (d, 2H, J=8.4 Hz), 7.42 (d, 2H, J=9.1 Hz), 7.65 (m, 2H), 7.90 (s, 1H), 8.10 (s, 1H), 8.32 (s, 1H); MS (ESI+): m\z 443.11.

(R)-1-(4-trifluoromethylphenyl)-3-{4-(2-methyl-6-nitro-2,3-dihydroimidazo[2,1-b]oxazol-2-yl)methoxyphenyl}thiourea (compound IIA10, Table 6, FIG. 22)

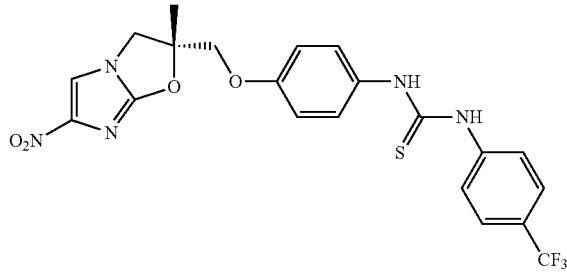 [SMILES: C[C@]1(COc2ccc(NC(=O)Nc3ccc(C(F)(F)F)cc3)cc2)Cn2cc([N+](=O)[O-])nc2O1]

TLC (DCM: EtOAc 2:8): R$_f$=0.40; $^1$H NMR (400 MHz, Acetone d$_6$): δ1.81 (s, 3H), 4.34 (m, 3H), 4.65 (d, 1H, J=10.8 Hz), 6.89 (d, 2H, J=9.0 Hz), 7.25 (d, 2H, J=8.4 Hz), 7.45 (d, 2H, J=9.1 Hz), 7.68 (d, 2H, J=9.1 Hz), 7.90 (s, 1H), 8.11 (s, 1H), 8.34 (s, 1H); MS (ESI+): m\z 493.10.

(R)-4-{(2-methyl-6-nitro-2,3-dihydroimidazo[2,1-b]oxazol-2-yl)methoxy}-N-(p-tolyl) benzenesulfonamide (compound IIB1, Table 7, FIG. 24)

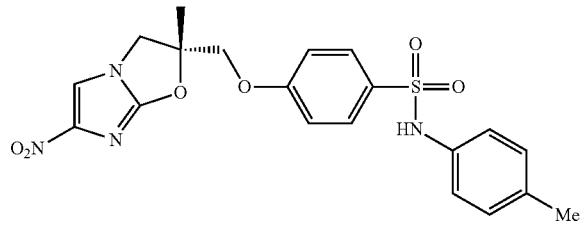 [SMILES: Cc1ccc(NS(=O)(=O)c2ccc(OC[C@@]3(C)Cn4cc([N+](=O)[O-])nc4O3)cc2)cc1]

TLC (DCM: EtOAc 2:8): R$_f$=0.30; $^1$H NMR (400 MHz, Acetone d$_6$): δ1.80 (s, 3H), 2.38 (s, 3H), 4.01 (brs, 1H), 4.32 (m, 3H), 4.62 (d, 1H, J=10.8 Hz), 6.98 (d, 2H, J=7.85 Hz), 7.02 (d, 2H, J=7.85 Hz), 7.12 (d, 2H, J=7.25 Hz), 7.64 (d, 2H, J=7.25 Hz), 7.90 (s, 1H); MS (ESI+): m\z 444.11.

(R)-4-{(2-methyl-6-nitro-2,3-dihydroimidazo[2,1-b]oxazol-2-yl)methoxy}-N-(4 trifluoro methoxyphenyl)benzenesulfonamide (compound IIB$_2$, Table 7, FIG. 24)

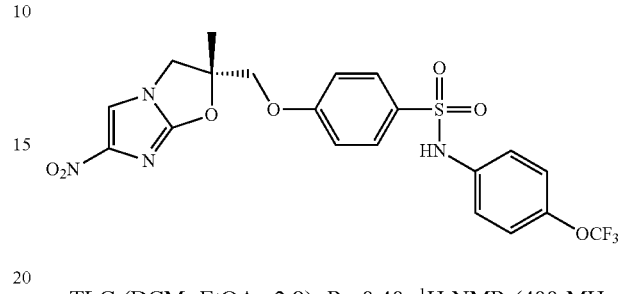

TLC (DCM: EtOAc 2:8): R$_f$=0.40; $^1$H NMR (400 MHz, Acetone d$_6$): δ 1.81 (s, 3H), 4.03 (brs, 1H), 4.33 (m, 3H), 4.64 (d, 1H, J=10.8 Hz), 6.94 (d, 2H, J=7.45 Hz), 7.12 (d, 2H, J=7.05 Hz), 7.64 (d, 2H, J=7.05 Hz), 7.89 (s, 1H); MS (ESI+): m\z 514.08.

(R)-4-{(2-methyl-6-nitro-2,3-dihydroimidazo[2,1-b]oxazol-2-yl)methoxy}-N-(4 trifluoro methylphenyl)benzenesulfonamide (compound IIB3, Table 7, FIG. 24)

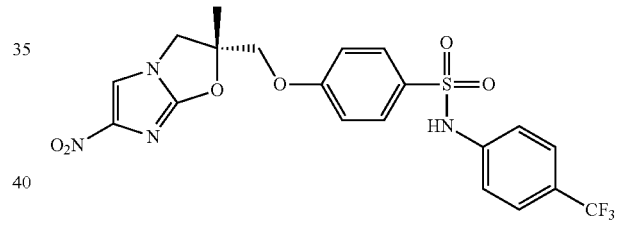

TLC (DCM: EtOAc 2:8): R$_f$=0.40; $^1$H NMR (400 MHz, Acetone d$_6$): δ 1.83 (s, 3H), 4.05 (brs, 1H), 4.35 (m, 3H), 4.65 (d, 1H, J=10.8 Hz), 6.98 (d, 2H, J=7.05 Hz), 7.12 (d, 2H, J=7.26 Hz), 7.30 (d, 2H, J=7.05 Hz), 7.64 (d, 2H, J=7.26 Hz), 7.91 (s, 1H); MS (ESI+): m\z 498.08.

(R)—N-methyl-4-{(2-methyl-6-nitro-2,3-dihydroimidazo[2,1-b]oxazol-2-yl)methoxy}-N-phenylbenzenesulfonamide (compound IIB4, Table 7, FIG. 24)

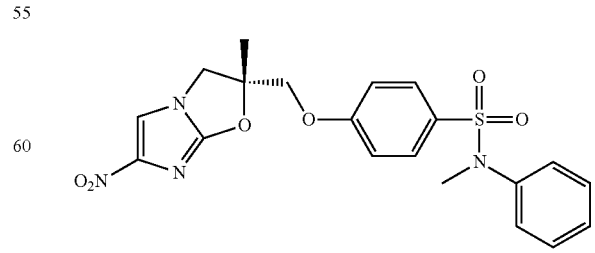

TLC (DCM: EtOAc 2:8): R$_f$=0.40; $^1$H NMR (400 MHz, Acetone d$_6$): δ 1.80 (s, 3H), 3.20 (s, 3H), 4.32 (m, 3H), 4.62

(d, 1H, J=10.8 Hz), 6.78-6.92 (m, 5H), 7.02 (d, 2H, J=7.25 Hz), 7.64 (d, 2H, J=7.25 Hz), 7.85 (s, 1H); MS (ESI+): m\z 444.11.

(R)—N-methyl-4-{(2-methyl-6-nitro-2,3-dihydrohnidazo[2,1-b]oxazol-2-yl)methoxy}-N-(p-tolyl)benzenesulfonamide (compound IIB5, Table 7, FIG. 24)

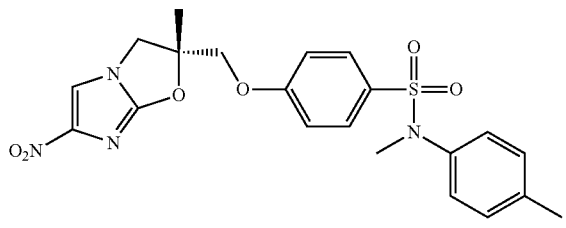 [SMILES: Cc1ccc(N(C)S(=O)(=O)c2ccc(OC[C@@]3(C)Cn4cc([N+](=O)[O-])nc4O3)cc2)cc1]

TLC (DCM: EtOAc 2:8): $R_f$=0.40; $^1$H NMR (400 MHz, Acetone d$_6$): δ 1.80 (s, 3H), 2.34 (s, 3H), 3.20 (s, 3H), 4.33 (m, 3H), 4.63 (d, 1H, J=10.8 Hz), 6.98 (d, 2H, J=7.85 Hz), 7.02 (d, 2H, J=7.85 Hz), 7.12 (d, 2H, J=7.25 Hz), 7.64 (d, 2H, J=7.25 Hz), 7.90 (s, 1H); MS (ESI+): m\z 458.13.

(R)—N-methyl-4-{(2-methyl-6-nitro-2,3-dihydroimidazo[2,1-b]oxazol-2-yl)methoxy}-N-(p-trifluoromethylphenyl)benzenesulfonamide (compound IIB6, Table 7, FIG. 24)

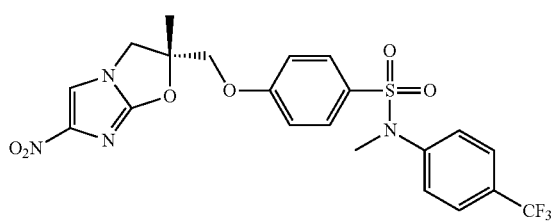

TLC (DCM: EtOAc 2:8): $R_f$=0.40; $^1$H NMR (400 MHz, Acetone d$_6$): δ 1.83 (s, 3.20 (s, 3H), 4.35 (m, 3H), 4.65 (d, 1H, J=10.8 Hz), 6.98 (d, 2H, J=7.05 Hz), 7.12 (d, 2H, J=7.26 Hz), 7.30 (d, 2H, J=7.05 Hz), 7.64 (d, 2H, J=7.26 Hz), 7.91 (s, 1H); MS (ESI+): m\z 512.10.

(R)-2-{4-(4-phenylpiperazin-1-yl)sulfonylphenoxymethyl}-2,3-dihydro-2-methyl-6-nitroimidazo[2,1-b]oxazole (compound IIC1, Table 8, FIG. 26)

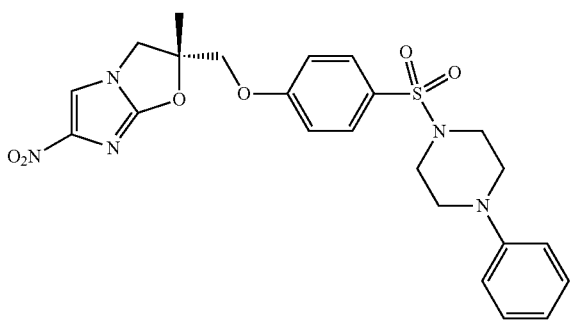 [SMILES: C[C@]1(COc2ccc(S(=O)(=O)N3CCN(c4ccccc4)CC3)cc2)Cn2cc([N+](=O)[O-])nc2O1]

TLC (DCM: EtOAc 2:8): $R_f$=0.30; $^1$H NMR (400 MHz, Acetone d$_6$): δ 1.81 (s, 3H), 3.19 (s, 8H), 4.32 (m, 3H), 4.62 (d, 1H, J=10.8 Hz), 7.01 (m, 2H), 7.05-7.24 (m, 3H), 7.12 (d, 2H, J=7.05 Hz), 7.64 (d, 2H, J=7.05 Hz), 7.89 (s, 1H); MS (ESI+): m\z 499.15.

(R)-2-{4-[4-(4-fluorophenylpiperazin-1-yl)sulfonylphenoxymethyl}-2,3-dihydro-2-methyl-6-nitroimidazo[2,1-b]oxazole (compound IIC2, Table 8, FIG. 26)

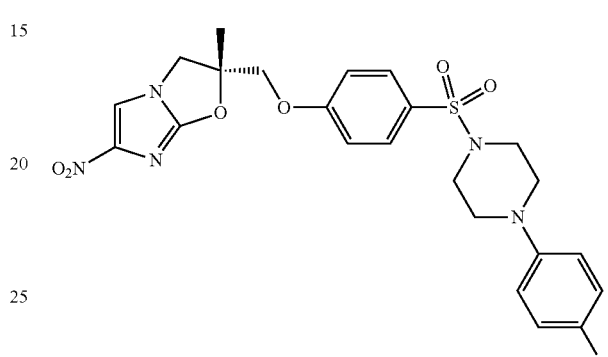

TLC (DCM: EtOAc 2:8): $R_f$=0.35; $^1$H NMR (400 MHz, Acetone d$_6$): δ 1.82 (s, 3H), 3.21 (s, 8H), 4.33 (m, 3H), 4.63 (d, 1H, J=10.8 Hz), 6.94 (d, 2H, J=7.15 Hz), 7.12 (d, 2H, J=7.05 Hz), 7.25 (m, 2H), 7.64 (d, 2H, J=7.05 Hz), 7.91 (s, 1H); MS (ESI+): m\z 517.14.

(R)-2-{4-[4-(3-chlorophenyl)piperazin-1-yl]sulfonylphenoxymethyl}-2,3-dihydro-2-methyl-6-nitroimidazo[2,1-b]oxazole (compound IIC3, Table 8, FIG. 26)

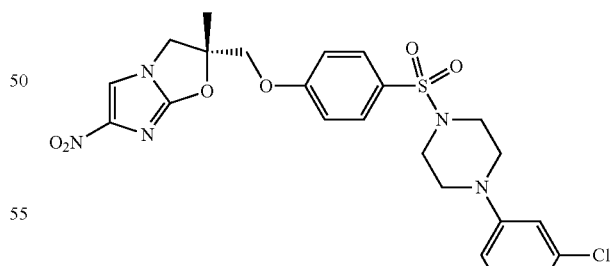

TLC (DCM: EtOAc 2:8): $R_f$=0.35; $^1$H NMR (400 MHz, Acetone d$_6$): δ1.81 (s, 3H), 3.20 (s, 8H), 4.31 (m, 3H), 4.62 (d, 1H, J=10.8 Hz), 6.94-7.12 (m, 3H), 7.21 (d, 2H, J=7.05 Hz), 7.35 (m, 1H), 7.64 (d, 2H, J=7.05 Hz), 7.90 (s, 1H); MS (ESI+): m\z 533.11.

(R)-2-{4-[4-(4-trifluoromethoxyphenylpiperazin-1-yl)sulfonylphenoxymethyl}-2,3-dihydro-2-methyl-6-nitroimidazo[2,1-b]oxazole (compound IIC4, Table 8, FIG. 26)

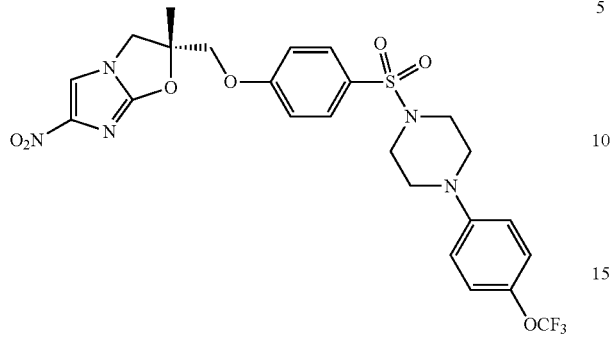

TLC (DCM: EtOAc 2:8): $R_f$=0.40; $^1$H NMR (400 MHz, Acetone $d_6$): δ1.81 (s, 3H), 3.19 (s, 8H), 4.31 (m, 3H), 4.62 (d, 1H, J=10.8 Hz), 6.94 (d, 2H, J=7.15 Hz), 7.01 (d, 2H, J=7.05 Hz), 7.25 (d, 2H, J=7.15 Hz), 7.64 (d, 2H, J=7.05 Hz), 7.89 (s, 1H); MS (ESI+): m\z 583.13.

(R)-ethyl-{4-[4-(2-methyl-6-nitro-2,3-dihydro imidazo[2,1-b]oxazol-2yl)methoxyphenyl]sulfonyl}piperazine-1-carboxylate (compound IIC5, Table 8, FIG. 26)

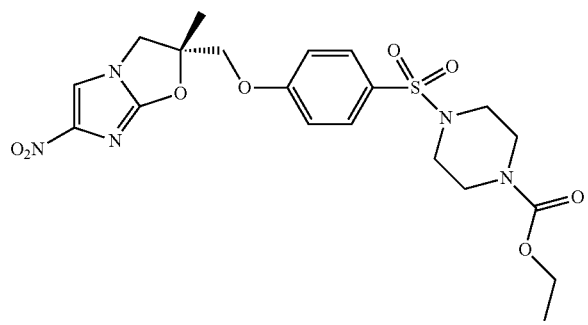 [SMILES: CCOC(=O)N1CCN(S(=O)(=O)c2ccc(OC[C@@]3(C)Cn4cc([N+](=O)[O-])nc4O3)cc2)CC1]

TLC (DCM: EtOAc 2:8): $R_f$=0.20; $^1$H NMR (400 MHz, Acetone $d_6$): δ1.29 (m, 3H), 1.80 (s, 3H), 3.25 (s, 8H), 4.13 (m, 2H), 4.31 (m, 3H), 4.62 (d, 1H, J=10.8 Hz), 7.12 (d, 2H, J=7.15 Hz), 7.64 (d, 2H, J=7.15 Hz), 7.95 (s, 1H); MS (ESI+): m\z 495.14.

(R)-{4-[4-(2-methyl-6-nitro-2,3-dihydrohnidazo[2,1-b]oxazol-2yl)methoxyphenyl]sulfonyl}piperazine-1-yl(phenyl)methanone (compound IIC6, Table 8, FIG. 26)

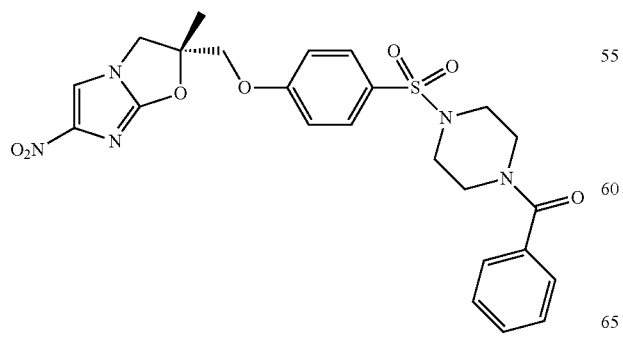

TLC (DCM: EtOAc 2:8): $R_f$=0.20; $^1$H NMR (400 MHz, Acetone $d_6$): δ1.81 (s, 3H), 3.19 (s, 8H), 4.31 (m, 3H), 4.62 (d, 1H, J=10.8 Hz), 6.94 (m, 3H), 7.01 (d, 2H, J=7.05 Hz), 7.30 (m, 2H), 7.64 (d, 2H, J=7.05 Hz), 7.91 (s, 1H); MS (ESI+): m\z 527.15.

(R)-2-{4-(piperidin-1-ylsulfonyl)phenoxymethyl}-2,3-dihydro-2-methyl-6-nitroimidazo[2,1-b]oxazole (compound IIC7, Table 8, FIG. 28)

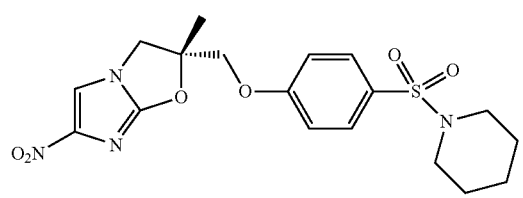 [SMILES: C[C@]1(COc2ccc(S(=O)(=O)N3CCCCC3)cc2)Cn2cc([N+](=O)[O-])nc2O1]

TLC (DCM: EtOAc 2:8): $R_f$=0.40; $^1$H NMR (400 MHz, Acetone $d_6$): δ 1.53 (m, 2H), 1.59 (m, 4H), 1.80 (s, 3H), 3.07 (m, 4H), 4.31 (m, 3H), 4.62 (d, 1H, J=10.8 Hz), 7.12 (d, 2H, J=7.15 Hz), 7.64 (d, 2H, J=7.15 Hz), 7.95 (s, 1H); MS (ESI+): m\z 422.13.

(R)-2-{4-[(4-phenylpiperidin-1-yl)sulfonyl]phenoxymethyl}-2,3-dihydro-2-methyl-6-nitroimidazo[2,1-b]oxazole (compound IIC8, Table 8, FIG. 26)

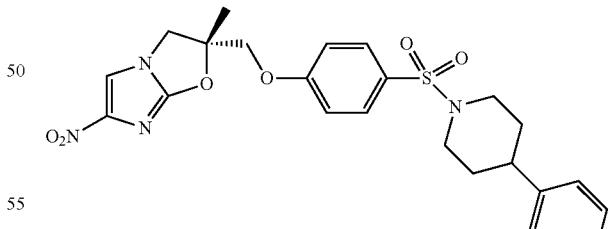

TLC (DCM: EtOAc 2:8): $R_f$=0.40; $^1$H NMR (400 MHz, Acetone $d_6$): δ1.59 (m, 4H), 1.80 (s, 3H), 2.59 (m, 1H), 3.17 (m, 4H), 4.31 (m, 3H), 4.62 (d, 1H, J=10.8 Hz), 6.95-7.05 (m, 5H), 7.12 (d, 2H, J=7.15 Hz), 7.64 (d, 2H, J=7.15 Hz), 7.93 (s, 1H); MS (ESI+): m\z 498.16.

65

(R)-2-{4-(pyrrolidin-1-ylsulfonyl)phenoxymethyl}-2,3-dihydro-2-methyl-6-nitroimidazo[2,1-b]oxazole (compound IIC9, Table 8, FIG. 26)

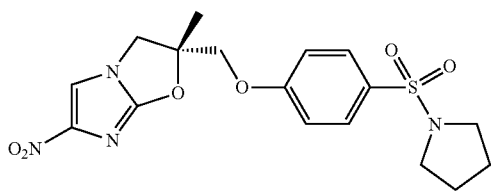 [SMILES: C[C@]1(COc2ccc(S(=O)(=O)N3CCCC3)cc2)Cn2cc([N+](=O)[O-])nc2O1]

TLC (DCM: EtOAc 2:8): $R_f$=0.40; $^1$H NMR (400 MHz, Acetone $d_6$): δ 1.92 (m, 4H), 1.80 (s, 3H), 3.07 (m, 4H), 4.31 (m, 3H), 4.62 (d, 1H, J=10.8 Hz), 7.12 (d, 2H, J=7.15 Hz), 7.64 (d, 2H, J=7.15 Hz), 7.95 (s, 1H); MS (ESI+): m\z 408.11.

66

(R)-2-{4-(morpholinsulfonyl)phenoxymethyl}-2,3-dihydro-2-methyl-6-nitroimidazo[2,1-b]oxazole (compound IIC10, Table 8, FIG. 26)

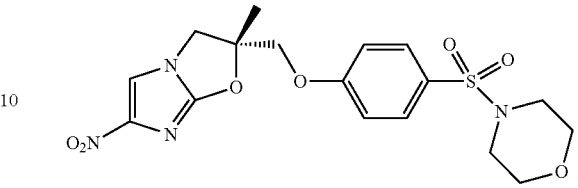

TLC (DCM: EtOAc 2:8): $R_f$=0.30; $^1$H NMR (400 MHz, Acetone $d_6$): δ 1.80 (s, 3H), 2.96 (m, 4H), 3.67 (m, 4H), 4.31 (m, 3H), 4.62 (d, 1H, J=10.8 Hz), 7.14 (d, 2H, J=7.15 Hz), 7.65 (d, 2H, J=7.15 Hz), 7.99 (s, 1H); MS (ESI+): m\z 424.11.

Table 1 shows the structure of representative compounds IA1-IA16 belonging to formula IA and synthesized as per scheme 5 provided in FIG. 8.

TABLE 1

| Entry | Code | Structure |
|---|---|---|
| 1 | IA1 | 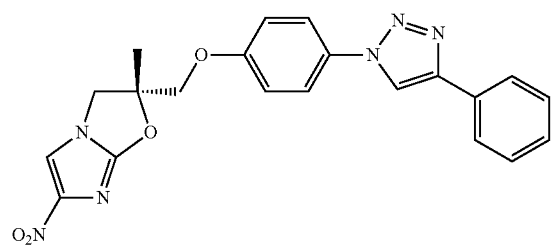 [SMILES: C[C@]1(COc2ccc(-n3cc(-c4ccccc4)nn3)cc2)Cn2cc([N+](=O)[O-])nc2O1] |
| 2 | IA2 | 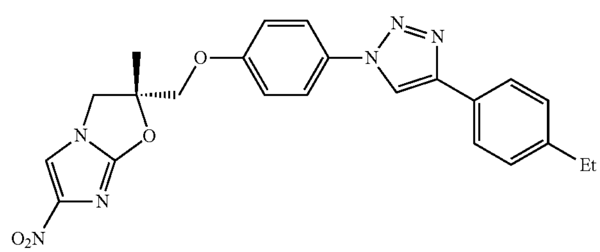 [SMILES: CCc1ccc(-c2cn(-c3ccc(OC[C@@]4(C)Cn5cc([N+](=O)[O-])nc5O4)cc3)nn2)cc1] |
| 3 | IA3 | 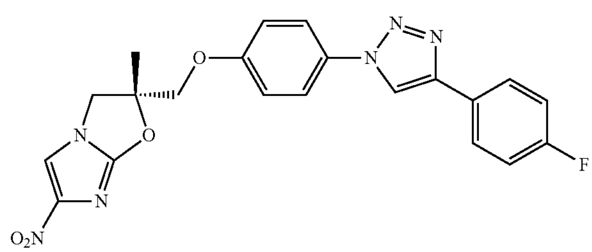 [SMILES: C[C@]1(COc2ccc(-n3cc(-c4ccc(F)cc4)nn3)cc2)Cn2cc([N+](=O)[O-])nc2O1] |
| 4 | IA4 | 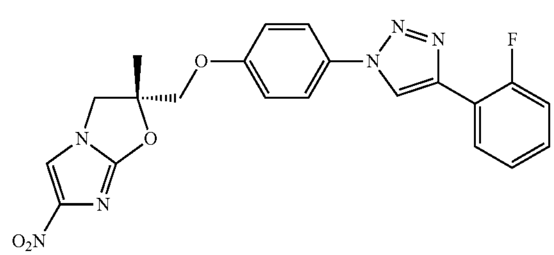 [SMILES: C[C@]1(COc2ccc(-n3cc(-c4ccccc4F)nn3)cc2)Cn2cc([N+](=O)[O-])nc2O1] |

TABLE 1-continued
| Entry | Code | Structure |
|---|---|---|
| 5 | IA5 | 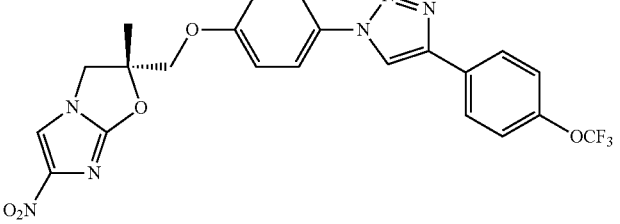 |
| 6 | IA6 | 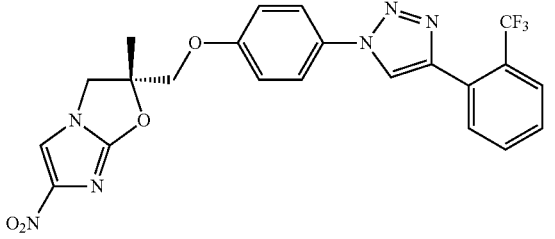 |
| 7 | IA7 | 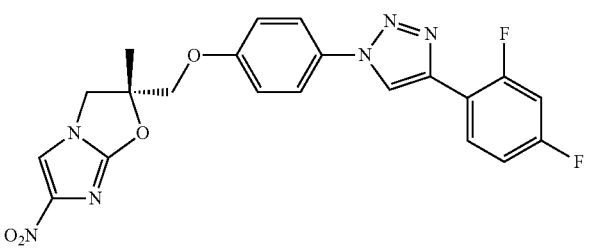 [SMILES: C[C@]1(COc2ccc(-n3cc(-c4ccc(F)cc4F)nn3)cc2)Cn2cc([N+](=O)[O-])nc2O1] |
| 8 | IA8 | 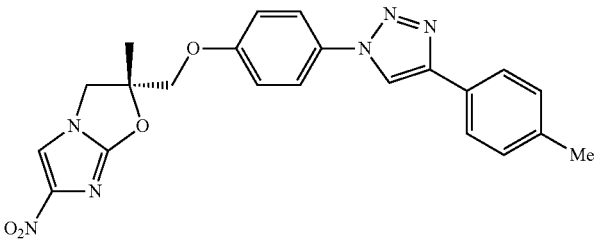 [SMILES: Cc1ccc(-c2cn(-c3ccc(OC[C@@]4(C)Cn5cc([N+](=O)[O-])nc5O4)cc3)nn2)cc1] |
| 9 | IA9 | 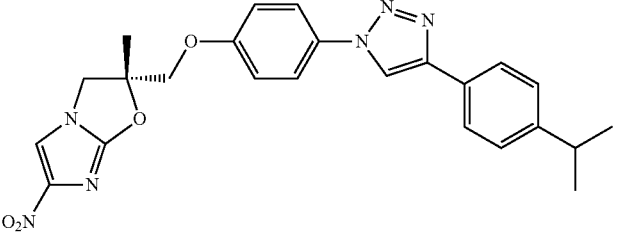 [SMILES: CC(C)c1ccc(-c2cn(-c3ccc(OC[C@@]4(C)Cn5cc([N+](=O)[O-])nc5O4)cc3)nn2)cc1] |
| 10 | IA10 | 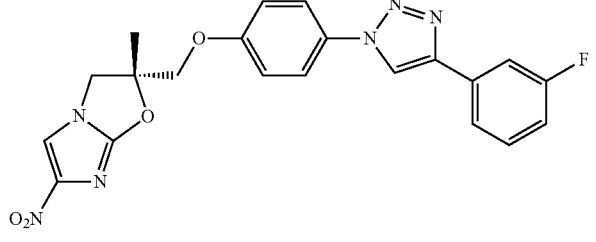 [SMILES: C[C@]1(COc2ccc(-n3cc(-c4cccc(F)c4)nn3)cc2)Cn2cc([N+](=O)[O-])nc2O1] |

TABLE 1-continued
| Entry | Code | Structure |
|---|---|---|
| 11 | IA11 | 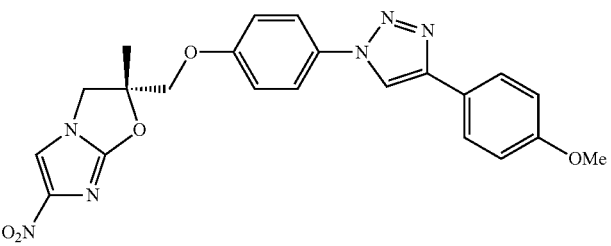 [SMILES: COc1ccc(-c2cn(-c3ccc(OC[C@@]4(C)Cn5cc([N+](=O)[O-])nc5O4)cc3)nn2)cc1] |
| 12 | IA12 | 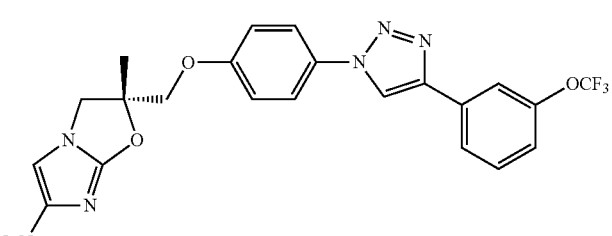 |
| 13 | IA13 | 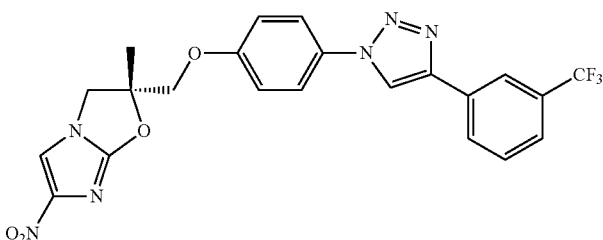 |
| 14 | IA14 | 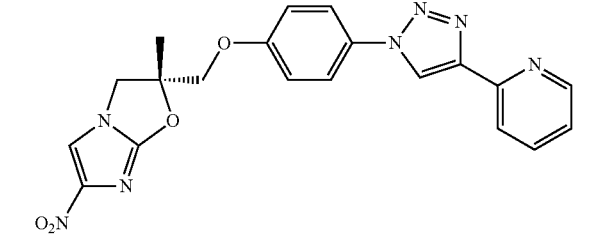 |
| 15 | IA15 | 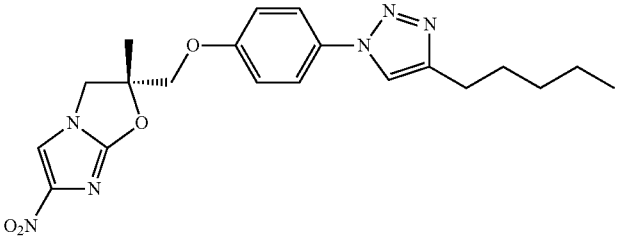 [SMILES: CCCCCc1cn(-c2ccc(OC[C@@]3(C)Cn4cc([N+](=O)[O-])nc4O3)cc2)nn1] |

TABLE 1-continued
| Entry | Code | Structure |
|---|---|---|
| 16 | IA16 | 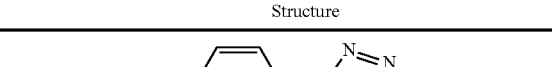 |
Table 2 shows the structure of representative compounds IA17-IA24 belonging to formula IA and synthesized as per scheme 5 provided in FIG. 8.
TABLE 2
| Entry | Code | Structure |
|---|---|---|
| 1 | IA17 | 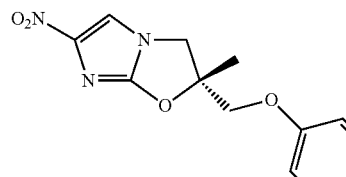 |
| 2 | IA18 | (structure shown) |
TABLE 2-continued
| Entry | Code | Structure |
|---|---|---|
| 3 | IA19 | (structure shown) |
| 4 | IA20 | (structure shown) |

TABLE 2-continued

| Entry | Code | Structure |
|---|---|---|
| 5 | IA21 | 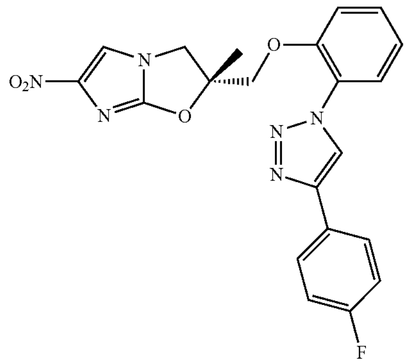 [SMILES: C[C@]1(COc2ccccc2-n2cc(-c3ccc(F)cc3)nn2)Cn2cc([N+](=O)[O-])nc2O1] |
| 6 | IA22 | 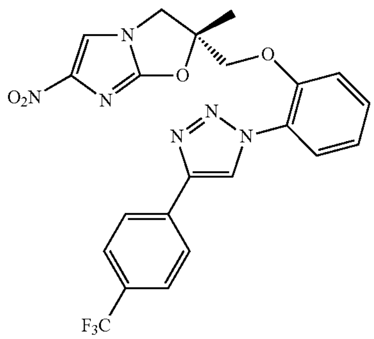 [SMILES: C[C@]1(COc2ccccc2-n2cc(-c3ccc(C(F)(F)F)cc3)nn2)Cn2cc([N+](=O)[O-])nc2O1] |
| 7 | IA23 | |

Table 3 shows the structure of representative compounds IA25-IA42 belonging to formula IA and synthesized as per scheme 9 provided in FIG. 12.

TABLE 3

| Entry | Code | Structure |
|---|---|---|
| 1 | IA25 | 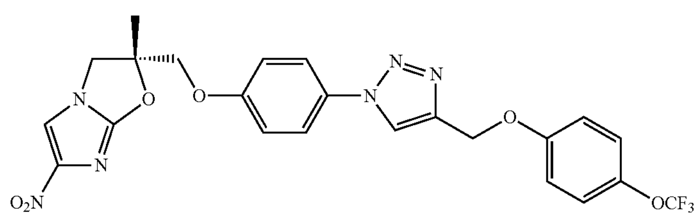 |
| 2 | IA26 | 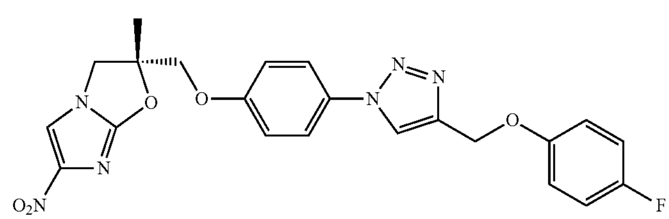 [SMILES: C[C@]1(COc2ccc(-n3cc(COc4ccc(F)cc4)nn3)cc2)Cn2cc([N+](=O)[O-])nc2O1] |
| 3 | IA27 | 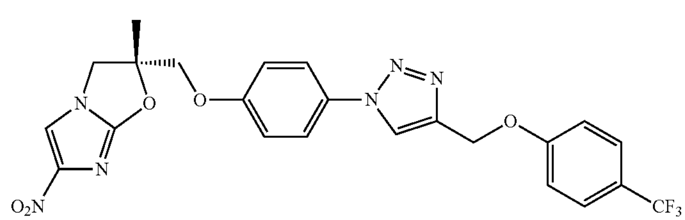 [SMILES: C[C@]1(COc2ccc(-n3cc(COc4ccc(C(F)(F)F)cc4)nn3)cc2)Cn2cc([N+](=O)[O-])nc2O1] |

TABLE 3-continued
| Entry | Code | Structure |
|---|---|---|
| 4 | IA28 | 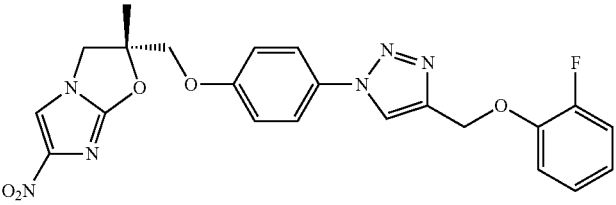 |
| 5 | IA29 | 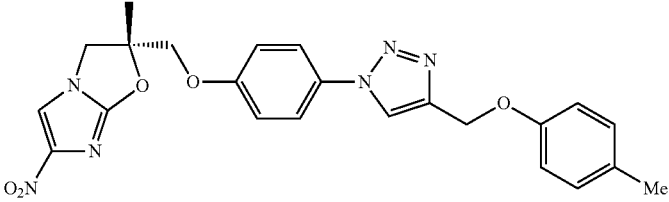 [SMILES: Cc1ccc(OCc2cn(-c3ccc(OC[C@@]4(C)Cn5cc([N+](=O)[O-])nc5O4)cc3)nn2)cc1] |
| 6 | IA30 | 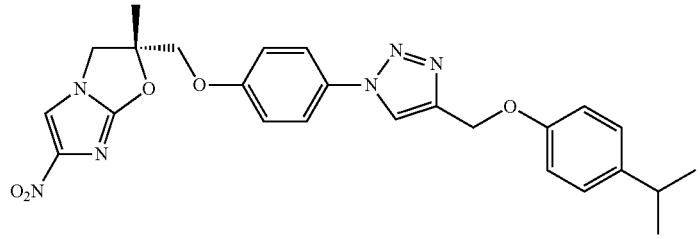 [SMILES: CC(C)c1ccc(OCc2cn(-c3ccc(OC[C@@]4(C)Cn5cc([N+](=O)[O-])nc5O4)cc3)nn2)cc1] |
| 7 | IA31 | 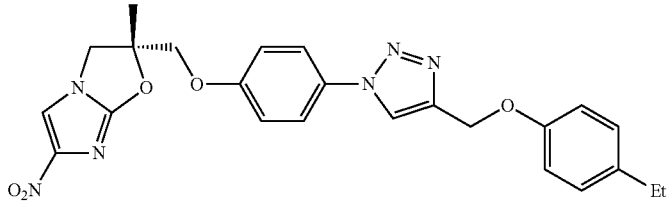 [SMILES: CCc1ccc(OCc2cn(-c3ccc(OC[C@@]4(C)Cn5cc([N+](=O)[O-])nc5O4)cc3)nn2)cc1] |
| 8 | IA32 | 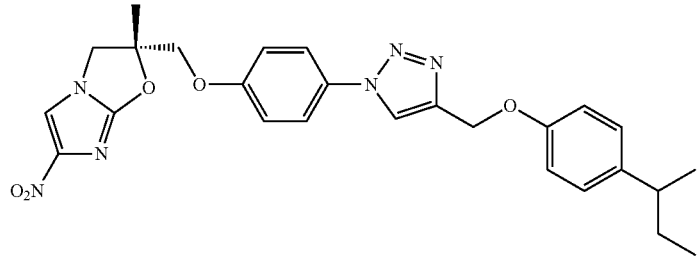 [SMILES: CCC(C)c1ccc(OCc2cn(-c3ccc(OC[C@@]4(C)Cn5cc([N+](=O)[O-])nc5O4)cc3)nn2)cc1] |
| 9 | IA33 | 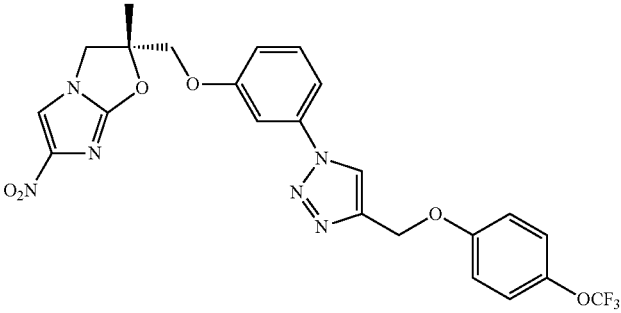 [SMILES: C[C@]1(COc2cccc(-n3cc(COc4ccc(OC(F)(F)F)cc4)nn3)c2)Cn2cc([N+](=O)[O-])nc2O1] |

TABLE 3-continued

| Entry | Code | Structure |
|---|---|---|
| 10 | IA34 | (structure) |
| 11 | IA35 | (structure) |
| 12 | IA36 | (structure) |
| 13 | IA37 | (structure) |
| 14 | IA38 | (structure) |

TABLE 3-continued
| Entry | Code | Structure |
|---|---|---|
| 15 | IA39 | 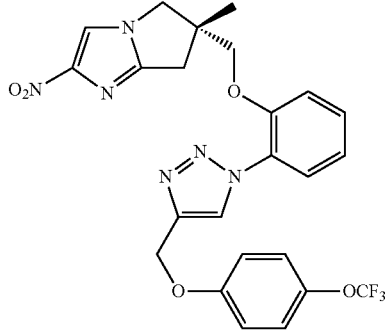 [SMILES: C[C@@]1(COc2ccccc2-n2cc(COc3ccc(OC(F)(F)F)cc3)nn2)Cc2nc([N+](=O)[O-])cn2C1] |
| 16 | IA40 | 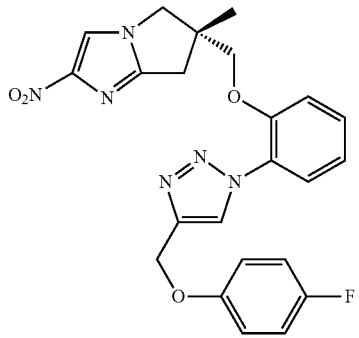 [SMILES: C[C@@]1(COc2ccccc2-n2cc(COc3ccc(F)cc3)nn2)Cc2nc([N+](=O)[O-])cn2C1] |
| 17 | IA41 | 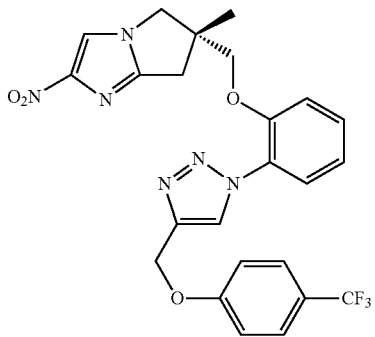 [SMILES: C[C@@]1(COc2ccccc2-n2cc(COc3ccc(C(F)(F)F)cc3)nn2)Cc2nc([N+](=O)[O-])cn2C1] |
| 18 | IA42 | 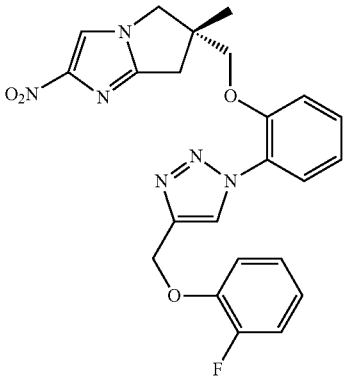 [SMILES: C[C@@]1(COc2ccccc2-n2cc(COc3ccccc3F)nn2)Cc2nc([N+](=O)[O-])cn2C1] |
Table 4 shows the structure of representative compounds IB1-IB10 belonging to formula IB and synthesized as per scheme 11 and scheme 13 provided in FIG. 14 and FIG. 16, respectively.

TABLE 4

| Entry | Code | Structure |
|---|---|---|
| 1 | IB1 | 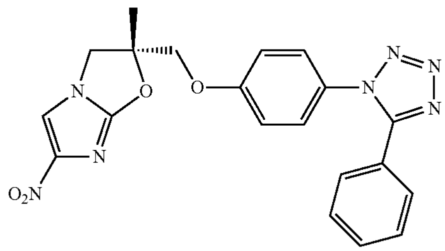 [SMILES: C[C@]1(COc2ccc(-n3nnnc3-c3ccccc3)cc2)Cn2cc([N+](=O)[O-])nc2O1] |
| 2 | IB2 | 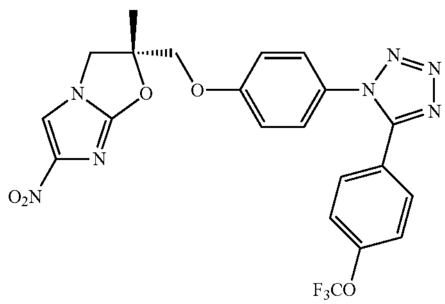 [SMILES: C[C@]1(COc2ccc(-n3nnnc3-c3ccc(OC(F)(F)F)cc3)cc2)Cn2cc([N+](=O)[O-])nc2O1] |
| 3 | IB3 | 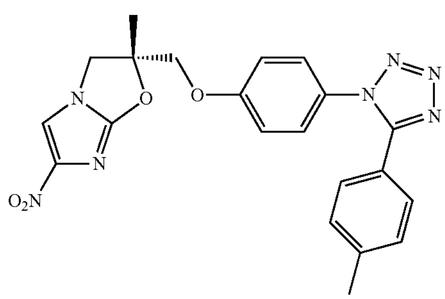 [SMILES: Cc1ccc(-c2nnnn2-c2ccc(OC[C@@]3(C)Cn4cc([N+](=O)[O-])nc4O3)cc2)cc1] |
| 4 | IB4 | 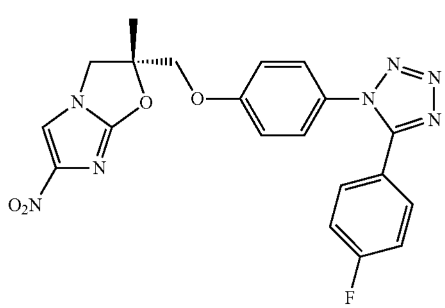 [SMILES: C[C@]1(COc2ccc(-n3nnnc3-c3ccc(F)cc3)cc2)Cn2cc([N+](=O)[O-])nc2O1] |
| 5 | IB5 | 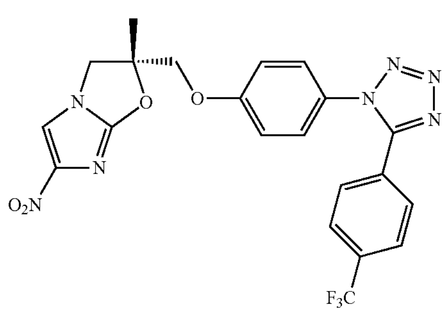 [SMILES: C[C@]1(COc2ccc(-n3nnnc3-c3ccc(C(F)(F)F)cc3)cc2)Cn2cc([N+](=O)[O-])nc2O1] |
| 6 | IB6 | |
| 7 | IB7 | |
| 8 | IB8 | |
| 9 | IB9 | |
| 10 | IB10 | |

Table 5 shows the structure of representative compounds IC1-IC22 belonging to formula IC and synthesized as per scheme 15 and scheme 17 provided in FIG. 18 and FIG. 20, respectively.

TABLE 5
| Entry | Code | Structure |
|---|---|---|
| 1 | IC1 | 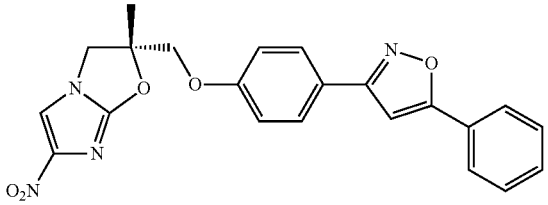 |
| 2 | IC2 | 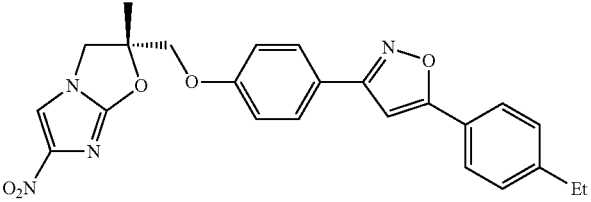 [SMILES: CCc1ccc(-c2cc(-c3ccc(OC[C@@]4(C)Cn5cc([N+](=O)[O-])nc5O4)cc3)no2)cc1] |
| 3 | IC3 | 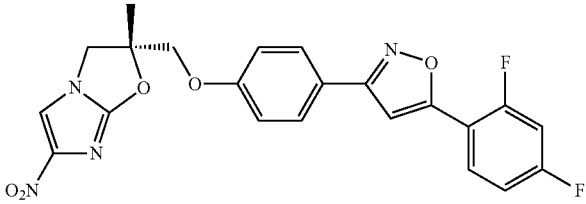 [SMILES: C[C@]1(COc2ccc(-c3cc(-c4ccc(F)cc4F)on3)cc2)Cn2cc([N+](=O)[O-])nc2O1] |
| 4 | IC4 | 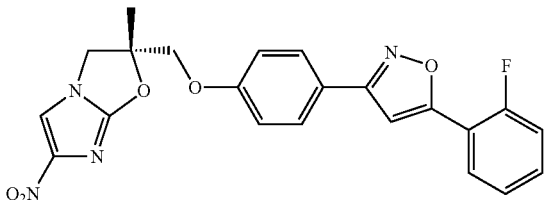 |
| 5 | IC5 | 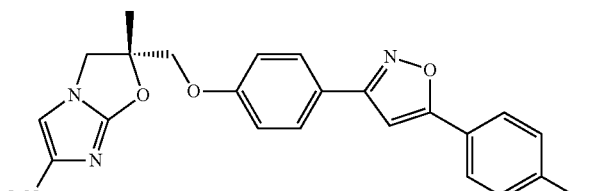 |
| 6 | IC6 | 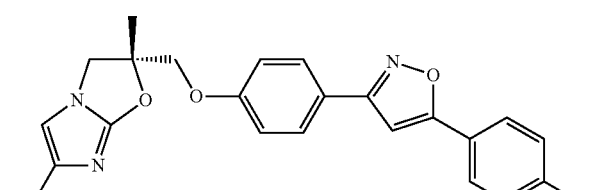 |
| 7 | IC7 | 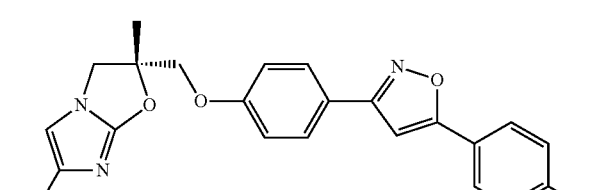 |

TABLE 5-continued

| Entry | Code | Structure |
|---|---|---|
| 8 | IC8 | 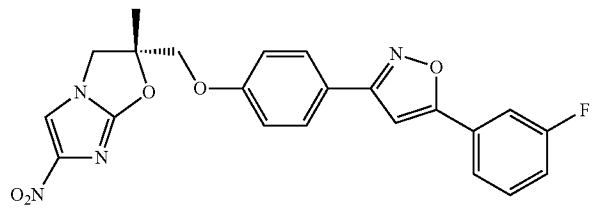 [SMILES: C[C@]1(COc2ccc(-c3cc(-c4cccc(F)c4)on3)cc2)Cn2cc([N+](=O)[O-])nc2O1] |
| 9 | IC9 | 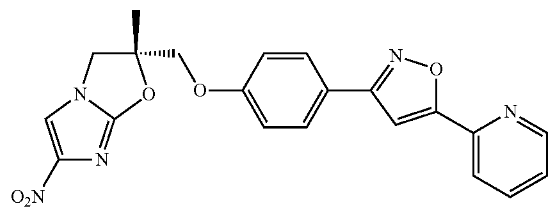 [SMILES: C[C@]1(COc2ccc(-c3cc(-c4ccccn4)on3)cc2)Cn2cc([N+](=O)[O-])nc2O1] |
| 10 | IC10 | 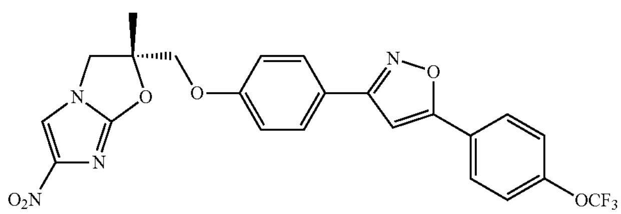 [SMILES: C[C@]1(COc2ccc(-c3cc(-c4ccc(OC(F)(F)F)cc4)on3)cc2)Cn2cc([N+](=O)[O-])nc2O1] |
| 11 | IC11 | 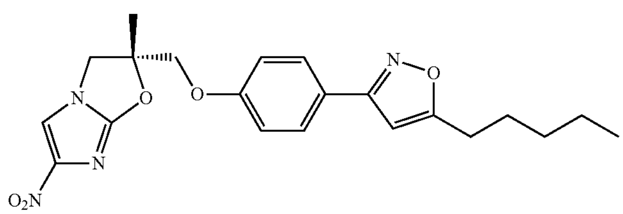 [SMILES: CCCCCc1cc(-c2ccc(OC[C@@]3(C)Cn4cc([N+](=O)[O-])nc4O3)cc2)no1] |
| 12 | IC12 | 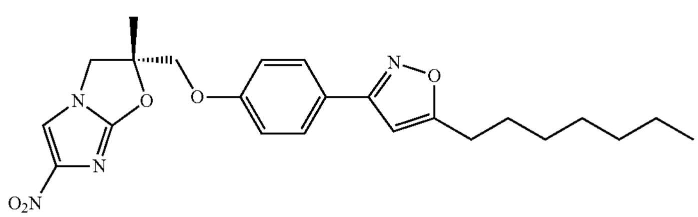 [SMILES: CCCCCCCc1cc(-c2ccc(OC[C@@]3(C)Cn4cc([N+](=O)[O-])nc4O3)cc2)no1] |
| 13 | IC13 | 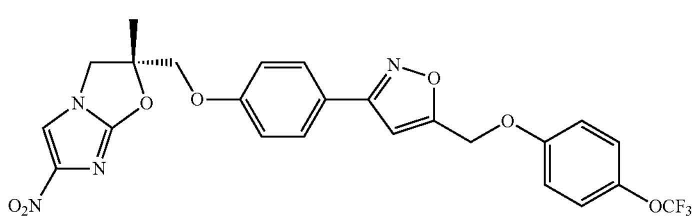 [SMILES: C[C@]1(COc2ccc(-c3cc(COc4ccc(OC(F)(F)F)cc4)on3)cc2)Cn2cc([N+](=O)[O-])nc2O1] |
| 14 | IC14 | 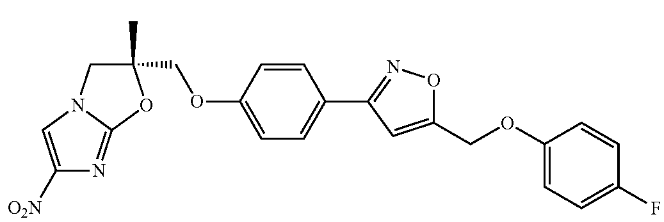 |

TABLE 5-continued

| Entry | Code | Structure |
|---|---|---|
| 15 | IC15 | 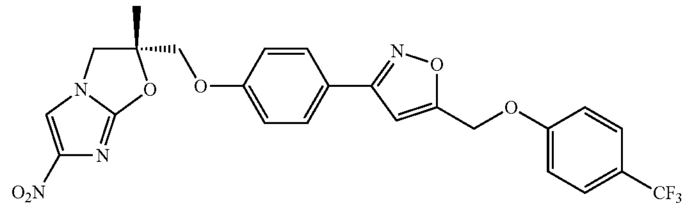 [SMILES: C[C@]1(COc2ccc(-c3cc(COc4ccc(C(F)(F)F)cc4)on3)cc2)Cn2cc([N+](=O)[O-])nc2O1] |
| 16 | IC16 | 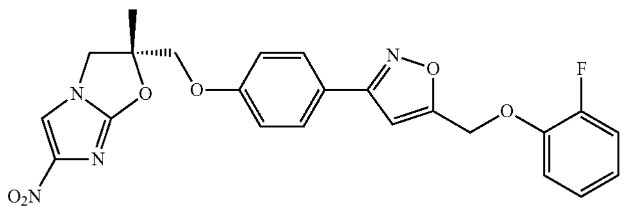 [SMILES: C[C@]1(COc2ccc(-c3cc(COc4ccccc4F)on3)cc2)Cn2cc([N+](=O)[O-])nc2O1] |
| 17 | IC17 | 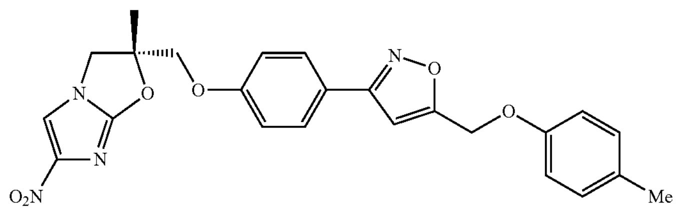 [SMILES: Cc1ccc(OCc2cc(-c3ccc(OC[C@@]4(C)Cn5cc([N+](=O)[O-])nc5O4)cc3)no2)cc1] |
| 18 | IC18 | 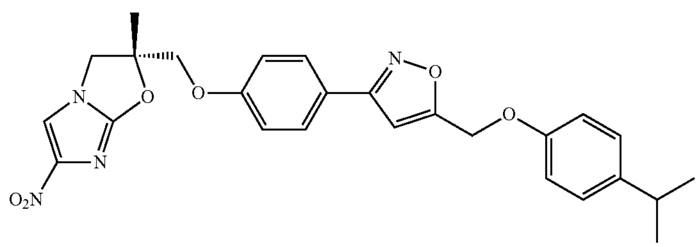 [SMILES: CC(C)c1ccc(OCc2cc(-c3ccc(OC[C@@]4(C)Cn5cc([N+](=O)[O-])nc5O4)cc3)no2)cc1] |
| 19 | IC19 | 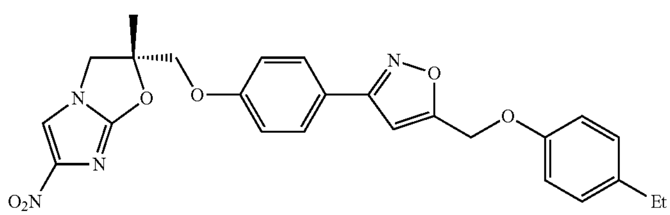 [SMILES: CCc1ccc(OCc2cc(-c3ccc(OC[C@@]4(C)Cn5cc([N+](=O)[O-])nc5O4)cc3)no2)cc1] |
| 20 | IC20 | 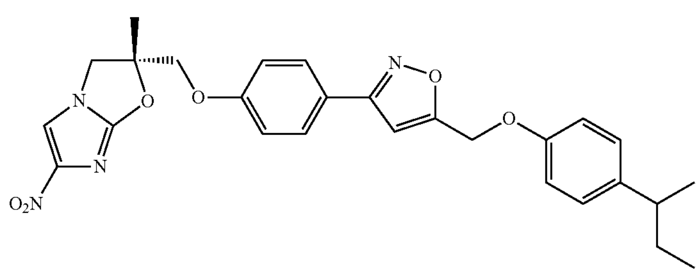 [SMILES: CCC(C)c1ccc(OCc2cc(-c3ccc(OC[C@@]4(C)Cn5cc([N+](=O)[O-])nc5O4)cc3)no2)cc1] |
| 21 | IC21 | 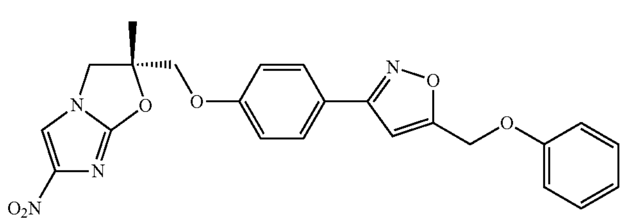 [SMILES: C[C@]1(COc2ccc(-c3cc(COc4ccccc4)on3)cc2)Cn2cc([N+](=O)[O-])nc2O1] |

TABLE 5-continued

| Entry | Code | Structure |
|---|---|---|
| 22 | IC22 | 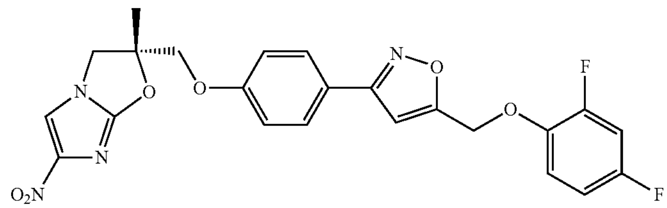 [SMILES: C[C@]1(COc2ccc(-c3cc(COc4ccc(F)cc4F)on3)cc2)Cn2cc([N+](=O)[O-])nc2O1] |

Table 6 shows the structure of representative compounds IIA1-IIA10 belonging to formula IIA and synthesized as per scheme 19 provided in FIG. 22.

TABLE 6

| Entries | Codes | Structures |
|---|---|---|
| 1 | IIA1 | 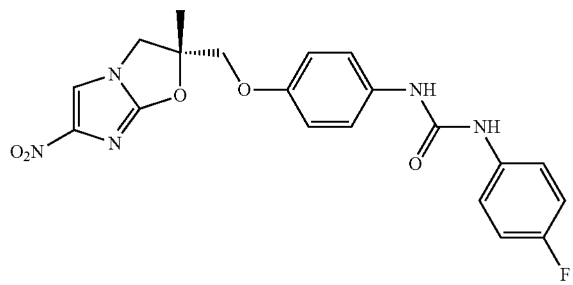 [SMILES: C[C@]1(COc2ccc(NC(=O)Nc3ccc(F)cc3)cc2)Cn2cc([N+](=O)[O-])nc2O1] |
| 2 | IIA2 | 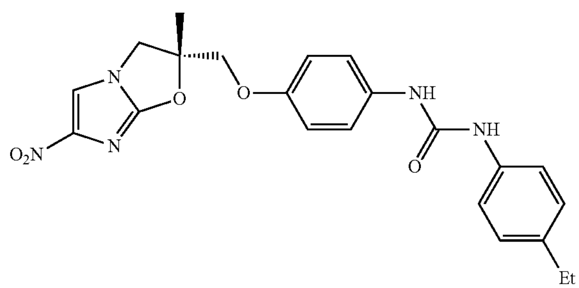 [SMILES: CCc1ccc(NC(=O)Nc2ccc(OC[C@@]3(C)Cn4cc([N+](=O)[O-])nc4O3)cc2)cc1] |
| 3 | IIA3 | 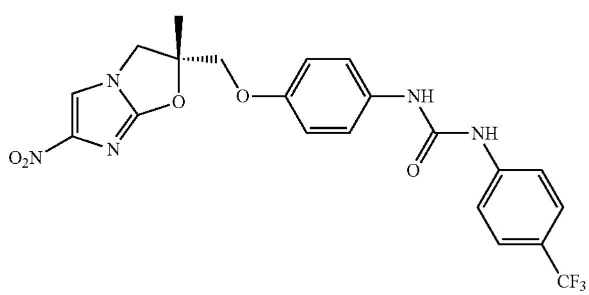 |
| 4 | IIA4 | 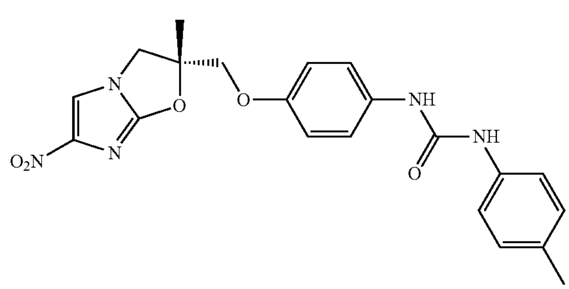 [SMILES: Cc1ccc(NC(=O)Nc2ccc(OC[C@@]3(C)Cn4cc([N+](=O)[O-])nc4O3)cc2)cc1] |

TABLE 6-continued
| Entries | Codes | Structures |
|---|---|---|
| 5 | IIA5 | 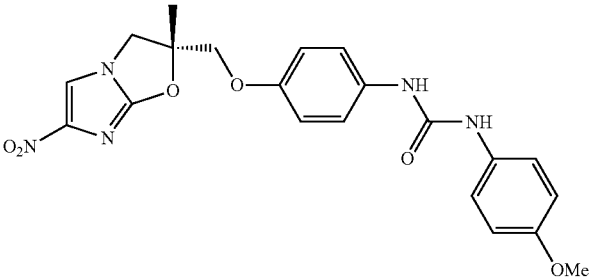 [SMILES: COc1ccc(NC(=O)Nc2ccc(OC[C@@]3(C)Cn4cc([N+](=O)[O-])nc4O3)cc2)cc1] |
| 6 | IIA6 | 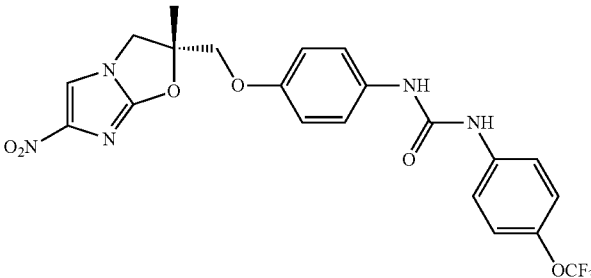 |
| 7 | IIA7 | 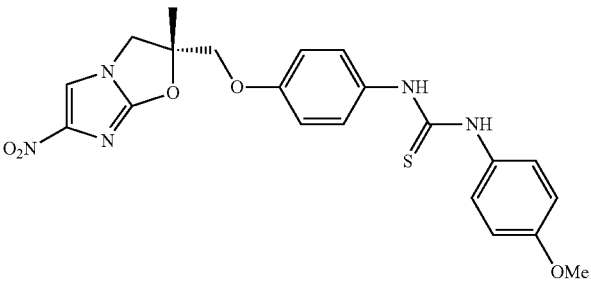 |
| 8 | IIA8 | 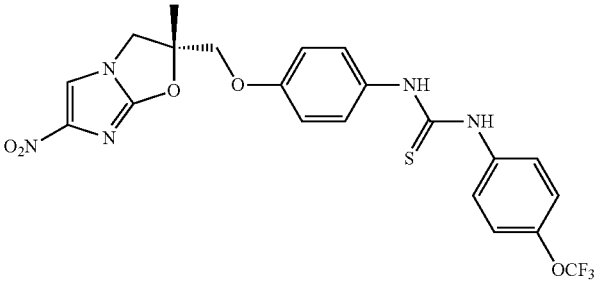 [SMILES: C[C@]1(COc2ccc(NC(=O)Nc3ccc(OC(F)(F)F)cc3)cc2)Cn2cc([N+](=O)[O-])nc2O1] |
| 9 | IIA9 | 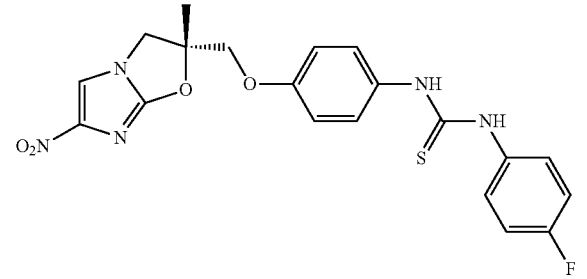 |

TABLE 6-continued

| Entries | Codes | Structures |
|---|---|---|
| 10 | IIA10 | *(structure shown)* |

Table 7 shows the structure of representative compounds IIB1-IIB6 belonging to formula IIB and synthesized as per scheme 21 provided in FIG. 24.

TABLE 7

| Entries | Codes | Structures |
|---|---|---|
| 1 | IIB1 | *(structure shown)* |
| 2 | IIB2 | *(structure shown)* |
| 3 | IIB3 | *(structure shown)* |
| 4 | IIB4 | *(structure shown)* |

TABLE 7-continued

| Entries | Codes | Structures |
|---|---|---|
| 5 | IIB5 | 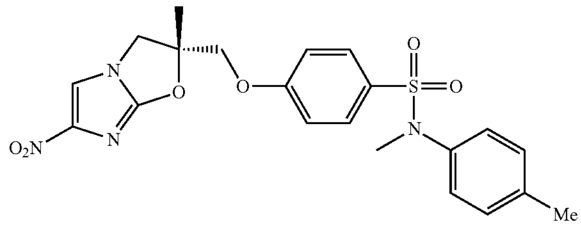 [SMILES: Cc1ccc(N(C)S(=O)(=O)c2ccc(OC[C@@]3(C)Cn4cc([N+](=O)[O-])nc4O3)cc2)cc1] |
| 6 | IIB6 | 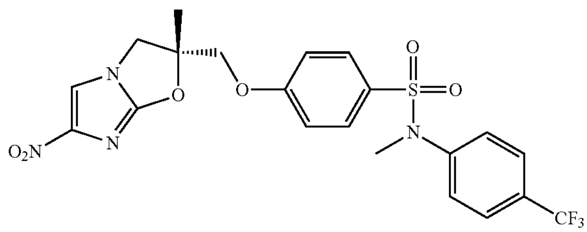 [SMILES: CN(c1ccc(C(F)(F)F)cc1)S(=O)(=O)c1ccc(OC[C@@]2(C)Cn3cc([N+](=O)[O-])nc3O2)cc1] |

Table 8 shows the structure of representative compounds IIC1-IIC10 belonging to formula IIC and synthesized as per scheme 23 provided in FIG. 26.

TABLE 8

| Entries | Codes | Structures |
|---|---|---|
| 1 | IIC1 | 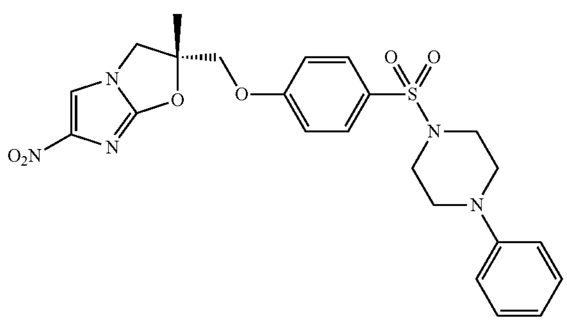 [SMILES: C[C@]1(COc2ccc(S(=O)(=O)N3CCN(c4ccccc4)CC3)cc2)Cn2cc([N+](=O)[O-])nc2O1] |
| 2 | IIC2 | 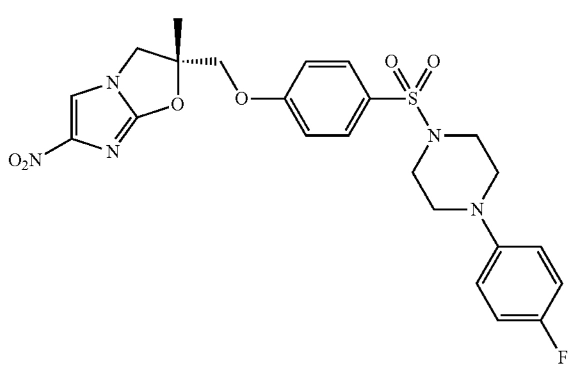 [SMILES: C[C@]1(COc2ccc(S(=O)(=O)N3CCN(c4ccc(F)cc4)CC3)cc2)Cn2cc([N+](=O)[O-])nc2O1] |

TABLE 8-continued
| Entries | Codes | Structures |
|---|---|---|
| 3 | IIC3 | 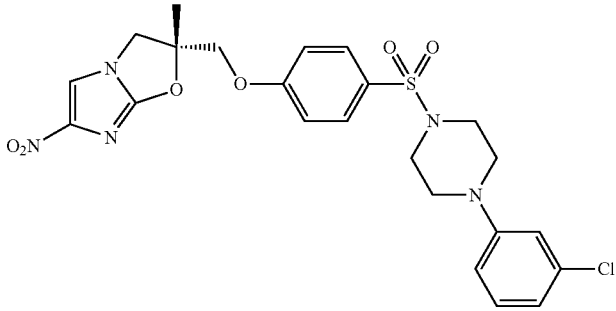 [SMILES: C[C@]1(COc2ccc(S(=O)(=O)N3CCN(c4cccc(Cl)c4)CC3)cc2)Cn2cc([N+](=O)[O-])nc2O1] |
| 4 | IIC4 | 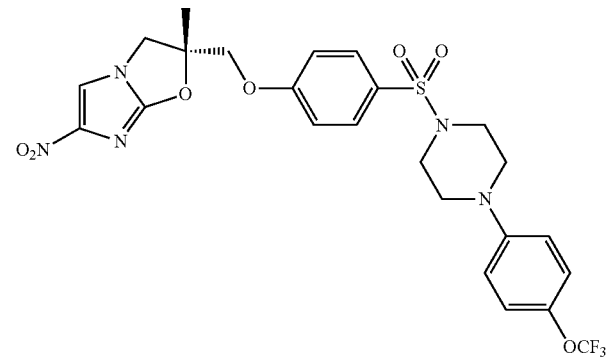 [SMILES: C[C@]1(COc2ccc(S(=O)(=O)N3CCN(c4ccc(OC(F)(F)F)cc4)CC3)cc2)Cn2cc([N+](=O)[O-])nc2O1] |
| 5 | IIC5 | 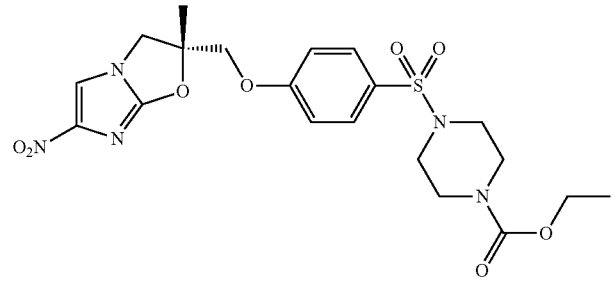 [SMILES: CCOC(=O)N1CCN(S(=O)(=O)c2ccc(OC[C@@]3(C)Cn4cc([N+](=O)[O-])nc4O3)cc2)CC1] |
| 6 | IIC6 | 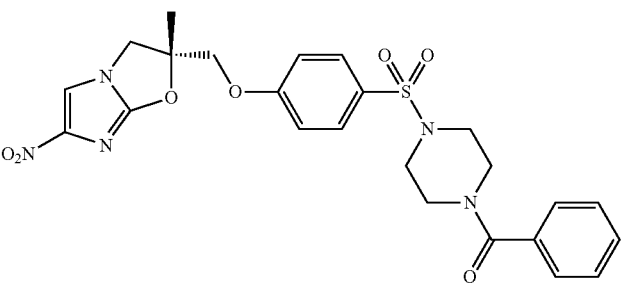 [SMILES: C[C@]1(COc2ccc(S(=O)(=O)N3CCN(C(=O)c4ccccc4)CC3)cc2)Cn2cc([N+](=O)[O-])nc2O1] |
| 7 | IIC7 | 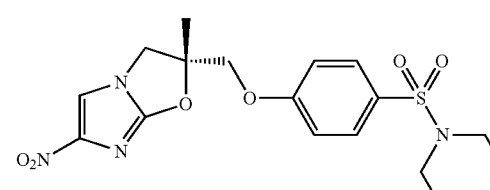 |

TABLE 8-continued

| Entries | Codes | Structures |
|---|---|---|
| 8 | IIC8 | 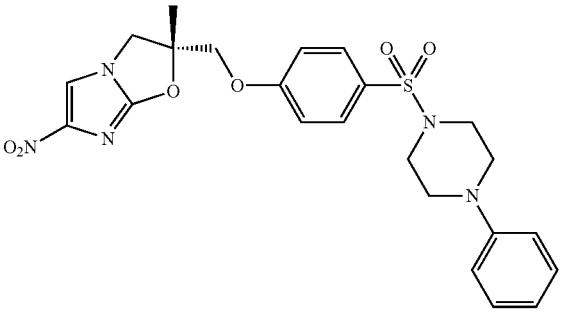 [SMILES: C[C@]1(COc2ccc(S(=O)(=O)N3CCN(c4ccccc4)CC3)cc2)Cn2cc([N+](=O)[O-])nc2O1] |
| 9 | IIC9 | 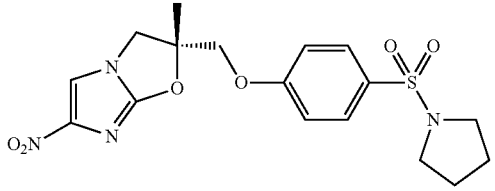 [SMILES: C[C@]1(COc2ccc(S(=O)(=O)N3CCCC3)cc2)Cn2cc([N+](=O)[O-])nc2O1] |
| 10 | IIC10 | 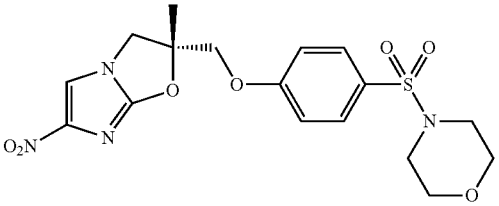 [SMILES: C[C@]1(COc2ccc(S(=O)(=O)N3CCOCC3)cc2)Cn2cc([N+](=O)[O-])nc2O1] |

Biological Evaluation

Example 11

Physiochemical Properties

The physiochemical properties (log $P_O$/w, log S, log Khsa) of the compounds IA1 to IIC10 were evaluated by using the schrodinger software. The detailed results were shown in Table 9.

Example 12

In Vitro Activity of Compounds 1A1 to IIC10 Against *M. tuberculosis* H37Rv and Two Clinical Isolates (MDR *M. tuberculosis* & XDR *M. tuberculosis*)

MIC Determination:

MIC was determined by broth dilution method against *M. tuberculosis* H37Rv (ATCC 27294; American Type Culture Collection, Manassas, Va.), *M. tuberculosis* MDR (resistant to isoniazid and rifampicin) and *M. tuberculosis* XDR (resistant to isoniazid, rifampicin, amikacin and moxifloxacin). The bacterial strains were grown for 10 to 15 days in Middlebrook 7H9 broth (Difco Laboratories, Detroit, Mich.) supplemented with 0.5% (v/v) glycerol, 0.25% (v/v) Tween 80 (Himedia, Mumbai India), and 10% ADC (albumin dextrose catalase; Becton Dickinson, Sparks, Md.) under shaking conditions at 37° C. in 5% $CO_2$ to facilitate exponential-phase growth of the organism. Bacterial suspension was prepared by suspending *M. tuberculosis* growth in normal saline containing 0.5% tween 80 and turbidity was adjusted to 1 McFarland standard which is equivalent to $1.5\times10^7$ CFU/ml. The 2-fold serial dilutions of compounds IA1 to IIC10 were prepared in Middle brook 7H9 (Difco laboratories) for *M. tuberculosis* in 100 □l per well in 96-well U bottom microtitre plates (Tarson, Mumbai, India). The above-mentioned bacterial suspension was further diluted in the growth media and 100 □l volume of this diluted inoculum was added to each well of the plate resulting in the final inoculum of $5\times10^5$ CFU/ml in the well and the final concentrations of compound IA1 to IIC10 ranged from 0.015 to 32 μg/ml. The plates were incubated at 37° C. for 3-weeks in 5% $CO_2$. The plates were read visually and the minimum concentration of the compound showing no turbidity was recorded as MIC.

Results:

Triazolyl containing 6-nitro-2,3-dihydroimidazo[2,1-b]-oxazole compounds IA1-IA42, were screened against both sensitive $H_{37}Rv$ as well as multi- and extensive-drug resistant strains of *M. tuberculosis*, wherein 12 compounds IA3, IA5, IA11, IA12, IA25, IA26, IA27, IA28, IA31, IA32, IA33 and IA34 showed MIC value of <1.0 μg/ml (results provided in Table 9). Two compounds IA25 and IA33 showed very potent MIC of 0.12 μg/ml against sensitive and resistant strains of *M. tuberculosis*. Tetrazolyl containing 6-nitro-2,3-dihydroimidazo[2,1-b]-oxazole compounds IB1-IB10 showed MIC of 1 to 4.0 μg/ml against $H_{37}Rv$, MDR and XDR *M. tuberculosis*. Isoxazolyl containing 6-nitro-2,3-dihydroimidazo[2,1-b]-oxazole compounds IC1-IC22 were also screened against both sensitive $H_{37}Rv$ as well as multi- and extensive-drug resistant strains of *M. tuberculosis*, wherein 11 compounds IC1, IC3, IC7, IC10, IC13, IC14, IC15, IC16, IC17, IC18 and IC22 showed potent MIC value of <1.0 μg/ml. Among these compounds, three compounds IC1, IC13 and IC14 showed MIC value of 0.06, 0.12 and 0.06 µg/ml respectively against H37Rv *M. Tuberculosis*. Uridyl containing 6-nitro-2,3-dihydro imidazo[2,1-b]-oxazole compounds IIA1-IIA10 were also synthesized and screened against sensitive $H_{37}Rv$ as well as multi- and extensive-drug resistant strains of *M. tuberculosis*, wherein 4 compounds IIA2, IIA3, IIA4 and IIA6 showed MIC value of <1.0 μg/ml against $H_{37}Rv$, MDR and XDR *M. tuberculosis*. *Sulphanamidyl containing* 6-nitro-2,3-dihydroimidazo [2,1-b]-oxazole compounds IIB1-IIB6 and IIC1-IIC10 were also synthesized and screened, wherein two compounds IIC8 and IIC10 showed MIC of 0.5 μg/ml against sensitive and resistant strains of *M. tuberculosis*. From these medicinal chemistry program, several new generation nitroimidazole based compounds were identified which possessed potent MIC against sensitive as well as resistant strain of *M. tuberculosis*

Example 13

Cytotoxicity Assay of Compounds IA1 to IIC10

Cell Culture:

The study was carried out using macrophage J774 cells line (ATCC-USA). Cells were grown in Rosewell Park Memorial Institute Medium (RPMI) containing 10% fetal calf serum (FCS) and supplemented with 75 mg/liter penicillin, 100 mg/liter streptomycin, 110 mg/liter Sodium pyruvate, 2.38 gm/liter HEPES, 0.05 mM 2 β-mercaptoethanol, and 2 gm/liter $NaHCO_3$, in a humidified atmosphere in 5% $CO_2$ at 37° C., and were sub-cultured at 1:4 ratio once a week.

Cell Treatment:

Cells were plated at a density of $3\times10^4$ cells/$cm^2$ and maintained in culture medium for 12 hours. Cells were seeded onto 96-well flat bottom plates and FCS was reduced to 5% for the experiment. Stock solutions of compounds IA1 to IIC10 were prepared fresh to avoid oxidation. Cells were incubated with the compounds (40 μg/ml) for 24 hrs.

Cytotoxicity Assays:

After the completion of incubation, the medium was removed and cell viability was evaluated by assaying for the ability of functional mitochondria to catalyze the reduction of 3-(4,5-dimethylthiazol-2-yl)-2,5-diphenyltetrazolium bromide (MTT) to form formazan salt by mitochondrial dehydrogenases, and determined by Elisa reader at 450 nm (Multiskan Spectrum; Thermo Electron Corporation, USA). Percentage cytotoxicity was calculated with respect to the untreated cells.

Results:

Compounds IA1 to IIC10 were not toxic up to 40 μg/ml concentration and the cytotoxicity assay results are shown in Table 9.

Table 9 shows the physico-chemical properties, Anti-tuberculosis activity and cytotoxicity of representative compound shown in tables 1 to 8.

TABLE 9

| | | | | | MIC (μg/ml) | | | Cytotox- | Selec- |
|---|---|---|---|---|---|---|---|---|---|
| S. No | Compound | logPo/w | logS | logKhsa | M. tb H37Rv | M. tb MDR | M. tb XDR | icity (μg/ml) | tivity Index |
| 1. | IA1 | 3.878 | −6.155 | 0.493 | 4 | 4 | 4 | >40 | >10 |
| 2. | IA2 | 4.177 | −6.023 | 0.621 | 2 | 4 | 4 | >40 | >10 |
| 3. | IA3 | 4.103 | −6.43 | 0.537 | 0.25 | 0.25 | 0.25 | >40 | >10 |
| 4. | IA4 | 4.076 | −6.338 | 0.531 | 1 | 2 | 2 | >40 | ND |
| 5. | IA5 | 4.715 | −7.186 | 0.71 | 0.5 | 0.5 | 0.5 | >40 | >10 |
| 6. | IA6 | 4.624 | −6.743 | 0.678 | 1.0 | 1.0 | 1.0 | >40 | >10 |
| 7. | IA7 | 4.186 | −6.494 | 0.522 | 2 | 2 | 2 | >40 | ND |
| 8. | IA8 | 4.189 | −6.667 | 0.665 | 1 | 1 | 1 | >40 | ND |
| 9. | IA9 | 4.728 | −7.192 | 0.879 | 1 | 1 | 1 | >40 | ND |
| 10. | IA10 | 4.117 | −6.531 | 0.539 | 2 | 2 | 2 | >40 | ND |
| 11. | IA11 | 3.921 | −6.201 | 0.465 | 0.25 | 0.25 | 0.25 | >40 | >10 |
| 12. | IA12 | 4.899 | −7.385 | 0.736 | 0.5 | 0.5 | 0.5 | >40 | >10 |
| 13. | IA13 | 4.721 | −7.201 | 0.712 | 2 | 2 | 2 | >40 | >10 |
| 14. | IA14 | 3.156 | −5.559 | 0.196 | 2 | 2 | 2 | >40 | >10 |
| 15. | IA15 | 4.008 | −6.099 | 0.487 | 32 | 32 | 32 | >40 | >10 |
| 16. | IA16 | 4.686 | −6.741 | 0.713 | 4 | 4 | 4 | >40 | ND |
| 17. | IA17 | 4.1 | −6.417 | 0.536 | 2 | 2 | 2 | >40 | ND |
| 18. | IA18 | 4.89 | −7.649 | 0.779 | 2 | 2 | 2 | >40 | ND |
| 19. | IA19 | 4.901 | −7.39 | 0.737 | 4 | 4 | 4 | >40 | ND |
| 20. | IA20 | 4.314 | −6.703 | 0.577 | 4 | 4 | 4 | >40 | ND |
| 21. | IA21 | 3.918 | −4.257 | 0.239 | 1 | 1 | 1 | >40 | ND |
| 22. | IA22 | 4.757 | −6.862 | 0.654 | 4 | 4 | 4 | >40 | ND |
| 23. | IA23 | 5.02 | −7.417 | 0.753 | 4 | 4 | 4 | >40 | ND |
| 24. | IA24 | 4.085 | −4.461 | 0.27 | 1.0 | 1.0 | 1.0 | >40 | >10 |
| 25. | IA25 | 5.239 | −7.628 | 0.732 | 0.12 | 0.12 | 0.12 | >40 | >10 |
| 26. | IA26 | 4.365 | −6.692 | 0.489 | 0.5 | 0.5 | 0.5 | >40 | >10 |
| 27. | IA27 | 5.05 | −7.479 | 0.68 | 0.25 | 0.25 | 0.25 | >40 | >10 |
| 28. | IA28 | 3.666 | −3.153 | −0.027 | 0.12 | 0.12 | 0.12 | >40 | >10 |
| 29. | IA29 | 4.287 | −6.48 | 0.553 | 32 | 32 | 32 | >40 | >10 |
| 30. | IA30 | 4.993 | −7.473 | 0.834 | 32 | 32 | 32 | >40 | >10 |
| 31. | IA31 | 4.654 | −6.889 | 0.68 | 0.25 | 0.25 | 0.25 | >40 | >10 |
| 32. | IA32 | 5.334 | −7.727 | 0.946 | 0.12 | 0.12 | 0.12 | >40 | >10 |
| 33. | IA33 | 5.25 | −7.791 | 0.741 | 0.12 | 0.12 | 0.12 | >40 | >10 |
| 34. | IA34 | 3.85 | −3.45 | 0.003 | 0.12 | 0.12 | 0.12 | >40 | >10 |
| 35. | IA35 | 4.597 | −4.661 | 0.284 | 2 | 2 | 2 | >40 | ND |
| 36. | IA36 | 3.88 | −3.548 | 0.014 | 2 | 2 | 2 | >40 | ND |
| 37. | IA37 | 4 | −4.242 | 0.228 | 4 | 4 | 4 | >40 | ND |
| 38. | IA38 | 4.972 | −7.524 | 0.835 | 4 | 4 | 4 | >40 | ND |
| 39. | IA39 | 4.835 | −5.319 | 0.375 | 1.0 | 1.0 | 1.0 | >40 | >10 |

TABLE 9-continued

| S. No | Compound | logPo/w | logS | logKhsa | MIC (µg/ml) M. tb H37Rv | MIC (µg/ml) M. tb MDR | MIC (µg/ml) M. tb XDR | Cytotoxicity (µg/ml) | Selectivity Index |
|---|---|---|---|---|---|---|---|---|---|
| 40. | IA40 | 3.893 | −4.655 | 0.251 | 4.0 | 4.0 | 4.0 | >40 | >10 |
| 41. | IA41 | 4.955 | −5.495 | 0.403 | 2 | 2 | 2 | >40 | >10 |
| 42. | IA42 | 4.327 | −5.864 | 0.396 | 2 | 2 | 2 | >40 | >10 |
| 43. | IB1 | 2.807 | −5.114 | 0.146 | 2 | 2 | 2 | >40 | ND |
| 44. | IB2 | 3.812 | −6.208 | 0.383 | 2 | 2 | 2 | >40 | ND |
| 45. | IB3 | 2.971 | −5.282 | 0.257 | 4 | 4 | 4 | >40 | ND |
| 46. | IB4 | 3.036 | −5.42 | 0.191 | 4 | 4 | 4 | >40 | ND |
| 47. | IB5 | 3.645 | −6.147 | 0.364 | 1 | 1 | 1 | >40 | ND |
| 48. | IB6 | 3.486 | −6.037 | 0.444 | 2 | 2 | 2 | >40 | ND |
| 49. | IB7 | 3.19 | −5.545 | 0.11 | 2 | 2 | 2 | >40 | ND |
| 50. | IB8 | 3.817 | −6.394 | 0.289 | 4 | 4 | 4 | >40 | ND |
| 51. | IB9 | 3.272 | −5.749 | 0.237 | 4 | 4 | 4 | >40 | ND |
| 52. | IB10 | 3.932 | −6.222 | 0.296 | 1 | 1 | 1 | >40 | ND |
| 53. | IC1 | 3.89 | −5.041 | 0.435 | 0.06 | 0.12 | 0.12 | >40 | >10 |
| 54. | IC2 | 4.862 | −7.334 | 0.923 | 2 | 2 | 2 | >40 | >10 |
| 55. | IC3 | 4.621 | −6.96 | 0.706 | 0.25 | 0.25 | 0.25 | >40 | >10 |
| 56. | IC4 | 4.395 | −6.685 | 0.661 | 2 | 2 | 2 | >40 | >10 |
| 57. | IC5 | 5.187 | −7.898 | 0.907 | 1.0 | 1.0 | 1.0 | >40 | >10 |
| 58. | IC6 | 4.511 | −7.027 | 0.799 | 1.0 | 1.0 | 1.0 | >40 | >10 |
| 59. | IC7 | 4.228 | −6.461 | 0.596 | 0.5 | 1.0 | 1.0 | >40 | >10 |
| 60. | IC8 | 4.425 | −6.793 | 0.671 | 2 | 2 | 2 | >40 | ND |
| 61. | IC9 | 3.455 | −5.814 | 0.326 | 2 | 2 | 2 | >40 | ND |
| 62. | IC10 | 5.336 | −7.864 | 0.923 | 0.5 | 0.5 | 0.5 | >40 | >10 |
| 63. | IC11 | 4.377 | −6.588 | 0.651 | 32 | 32 | 32 | >40 | >10 |
| 64. | IC12 | 5.101 | −7.442 | 0.905 | 2 | 2 | 2 | >40 | >10 |
| 65. | IC13 | 5.552 | −8.029 | 0.871 | 0.12 | 0.12 | 0.12 | >40 | >10 |
| 66. | IC14 | 4.52 | −6.515 | 0.558 | 0.06 | 0.12 | 0.12 | >40 | >10 |
| 67. | IC15 | 5.288 | −7.631 | 0.795 | 0.25 | 0.5 | 0.5 | >40 | >10 |
| 68. | IC16 | 4.397 | −5.588 | 0.441 | 0.5 | 0.5 | 0.5 | >40 | >10 |
| 69. | IC17 | 4.768 | −7.19 | 0.749 | 0.5 | 0.5 | 0.5 | >40 | >10 |
| 70. | IC18 | 5.311 | −7.74 | 0.966 | 0.25 | 0.25 | 0.25 | >40 | >10 |
| 71. | IC19 | 4.946 | −7.198 | 0.813 | 2 | 2 | 2 | >40 | ND |
| 72. | IC20 | 5.65 | −7.989 | 1.078 | 2 | 2 | 2 | >40 | ND |
| 73. | IC21 | 4.152 | −5.241 | 0.391 | 4 | 4 | 4 | >40 | ND |
| 74. | IC22 | 4.732 | −6.672 | 0.578 | 0.12 | 0.12 | 0.12 | >40 | >10 |
| 75. | IIA1 | 3.213 | −6.09 | 0.241 | 2 | 2 | 2 | >40 | >10 |
| 76. | IIA2 | 3.621 | −6.632 | 0.458 | 0.5 | 0.5 | 0.5 | >40 | >10 |
| 77. | IIA3 | 3.942 | −7.115 | 0.447 | 0.12 | 0.12 | 0.12 | >40 | >10 |
| 78. | IIA4 | 3.286 | −6.296 | 0.354 | 0.06 | 0.06 | 0.06 | >40 | >10 |
| 79. | IIA5 | 3.05 | −5.868 | 0.205 | 1.0 | 1.0 | 1.0 | >40 | >10 |
| 80. | IIA6 | 4.107 | −7.19 | 0.463 | 0.5 | 0.5 | 0.5 | >40 | >10 |
| 81. | IIA7 | 4.064 | −6.742 | 0.511 | 2 | 2 | 2 | >40 | ND |
| 82. | IIA8 | 4.948 | −7.646 | 0.712 | 2 | 2 | 2 | >40 | ND |
| 83. | IIA9 | 4.18 | −6.784 | 0.54 | 4 | 4 | 4 | >40 | ND |
| 84. | IIA10 | 4.932 | −7.902 | 0.748 | 4 | 4 | 4 | >40 | ND |
| 85. | IIB1 | 2.612 | −5.191 | 0.101 | 2 | 2 | 2 | >40 | ND |
| 86. | IIB2 | 3.445 | −6.106 | 0.212 | 2 | 2 | 2 | >40 | ND |
| 87. | IIB3 | 3.274 | −6.027 | 0.195 | 2 | 2 | 2 | >40 | ND |
| 88. | IIB4 | 2.116 | −2.889 | −0.418 | 4 | 4 | 4 | >40 | ND |
| 89. | IIB5 | 2.825 | −4.754 | −0.09 | 4 | 4 | 4 | >40 | ND |
| 90. | IIB6 | 3.497 | −5.606 | 0.016 | 1 | 1 | 1 | >40 | ND |
| 91. | IIC1 | 2.974 | −5.094 | −0.037 | 1 | 1 | 1 | >40 | ND |
| 92. | IIC2 | 3.396 | −5.809 | 0.03 | 2 | 2 | 2 | >40 | ND |
| 93. | IIC3 | 3.66 | −6.199 | 0.111 | 8.0 | 8.0 | 8.0 | >40 | >10 |
| 94. | IIC4 | 4.16 | −6.499 | 0.222 | 2 | 2 | 2 | >40 | >10 |
| 95. | IIC5 | 1.911 | −4.717 | −0.45 | 2.0 | 2.0 | 2.0 | >40 | >10 |
| 96. | IIC6 | 2.179 | −4.335 | −0.472 | 2.0 | 2.0 | 2.0 | >40 | >10 |
| 97. | IIC7 | 1.825 | −3.619 | −0.419 | 1.0 | 1.0 | 1.0 | >40 | >10 |
| 98. | IIC8 | 3.552 | −5.818 | 0.252 | 0.5 | 0.5 | 0.5 | >40 | >10 |
| 99. | IIC9 | 1.471 | −3.158 | −0.565 | 1.0 | 1.0 | 1.0 | >40 | >10 |
| 100. | IIC10 | 0.698 | −2.153 | −1.007 | 0.5 | 0.5 | 0.5 | >40 | >10 |

ND: not determined
MDR = *M. tuberculosis* resistant to isoniazid and rifampicin
XDR = *M. tuberculosis* resistant to isoniazid, rifampicin, amikacin and moxifloxacin

Example 14

In Vivo Pharmacokinetics

Compounds were administered orally to mice (Balb/c mice) at a dose of 5 mg/kg as a suspension in 0.5% CMC and Tween 80. Samples were derived from plasma at different time points i.e. 0.16 h, 0.5 h, 1 h, 2 h, 4 h, 6 h, 8 h and 24 h, which were then analysed by LC-MS/MS to generate the required pharmacokinetic parameters.

Result:

Four compounds IA25, IA33, IC13 and IC14 were studied for the pharmacokinetic properties along with OPC-67683 (clinical candidate of Otsuka). Two compounds IA25

($C_{max}$ 1023 nM and AUC 13960.67 nM*hr), IC13 ($C_{max}$ 2533.81 nM and AUC 33679 nM*hr) showed improved pharmacokinetic properties compared to OPC-67683 ($C_{max}$ 668 nM and AUC 9322.33 nM*hr). The detailed pharmacokinetic properties for the four compounds are shown in Table 11.

served as drug control. 100 microliters of 1:10 diluted of 1 Mc Farland inoculum was added to each well of the plate. Plates were then incubated at 37° C. for 14 days. MIC of drug alone and in presence of compound and vice versa was observed visually. The level of synergy was determined by calculating the fractional inhibitory concentration (FIC)

TABLE 11

| S. No | PK-parameters | OPC-67683 | IA25 | IA33 | IC13 | IC14 |
|---|---|---|---|---|---|---|
| 1 | $C_{MAX}$ (nM) | 668.01 | 1023.90 | 594.88 | 2533.81 | 352.65 |
| 2 | $T_{max}$ (hr) | 2.00 | 2.00 | 2.00 | 2.00 | 2.00 |
| 3 | AUC (nM*hr) | 9322.33 | 13960.67 | 3952.00 | 33679.00 | 1554.67 |
| 4 | Ka (hr) | 1.09 | 1.71 | 0.478 | 1.21 | 1.056 |
| 5 | $t_{1/2}$absorption (hr) | 0.64 | 0.41 | 1.448 | 0.57 | 0.656 |
| 6 | $CL_B$ (L/kg/hr) | 0.0043 | 0.007 | 0.072 | 0.0033 | 0.202 |
| 7 | Vdarea(L/kg) | 0.76 | 0.36 | 0.25 | 0.13 | 1.54 |

Example 15

Combination Studies

The efficacy of compounds IA25 and IIA3 (conc range 4 μg/ml to 0.007 μg/ml) in combination with currently used anti-TB drugs such as rifampicin, isoniazid and ethambutol (each drug tested at conc range 4 μg/ml to 0.007 mg/ml), wherein the ratio of drugs was ranging between 0.1% to 50%, was determined in vitro using checkerboard method. The checkerboard procedure was performed based on the MIC values by the broth microdilution method. The checkerboard method was performed in 96 well U bottom microtitre plates. 100 microliters of 4× concentration of drug was added to first column of the plate. 50 microliters from first column was transferred to second column and was serially diluted in horizontal manner upto column 10 of the plate. Seven dilutions of 4× concentration of compound were prepared in eppendorfs and fifty microliters of each concentration was added vertically starting from eleventh column of row eight to row second of the plate. First row of the plate index based on the following formula: FIC of drug A=MIC of drug A in combination/MIC of drug A alone; FIC of drug B=MIC of drug B in combination/MIC of drug B alone; and FIC index=FIC of drug A+FIC of drug B. Results of FIC index were interpreted as follows: ≤0.5: synergy, >0.5 to 0.75: partial synergy, >0.75 to 1.0: additive effect, >1.0 to 4.0: indifference, and >4.0: antagonism. The FIC index value for each concentration of two-drug combination was calculated and the minimum value was adopted.

Result:

The efficacy of compound IA25 in combination with known anti tuberculosis drugs has shown additive effect with rifampicin, synergistic effect with isoniazid and additive effect with ehambutol. Similarly compound IIA3 in combination with known anti tuberculosis drugs has shown synergistic effect with rifampicin, additive effect with isoniazid and additive effect with ehambutol and the detailed results of combination studies given in Table 10.

TABLE 10

| S. No | Combinations | MIC | FIC (MIC combination/ MIC alone) | FIC Index (FIC A + FIC B) | Observations |
|---|---|---|---|---|---|
| 1. | MIC of Rifampicin alone | 0.12 | FIC A = 0.25 | 0.5 | Synergistic |
|  | MIC of Rifampicin with IIA3 | 0.06 |  |  |  |
|  | MIC of IIA3 | 0.5 | FIC B = 0.25 |  |  |
|  | MIC of IIA3 with Rifampicin | 0.12 |  |  |  |
| 2. | MIC of INH alone | 0.25 | FIC A = 0.5 | 0.75 | Additive |
|  | MIC of INH with IIA3 | 0.12 |  |  |  |
|  | MIC of IIA3 | 0.5 | FIC B = 0.25 |  |  |
|  | MIC of IIA3 with INH | 0.12 |  |  |  |
| 3. | MIC of Ethambutol alone | 1.0 | FIC A = 0.5 | 0.75 | Additive |
|  | MIC of Ehambutol with IIA3 | 0.5 |  |  |  |
|  | MIC of IIA3 | 0.5 | FIC B = 0.25 |  |  |
|  | MIC of IIA3 with Ehambutol | 0.12 |  |  |  |
| 4. | MIC of Rifampicin alone | 0.12 | FIC A = 0.25 | 0.75 | Additive |
|  | MIC of Rifamipicin with IA25 | 0.03 |  |  |  |
|  | MIC of IA25 | 0.12 | FIC B = 0.5 |  |  |
|  | MIC of IA25 with Rifampicin | 0.06 |  |  |  |
| 5. | MIC of INH alone | 0.25 | FIC A = 0.25 | 0.5 | Synergistic |
|  | MIC of INH with IA25 | 0.06 |  |  |  |
|  | MIC of IA25 | 0.12 | FIC B = 0.25 |  |  |
|  | MIC of IA25 with INH | 0.03 |  |  |  |
| 6. | MIC of Ethambutol alone | 1.0 | FIC A = 0.25 | 0.75 | Additive |
|  | MIC of Ehambutol with IA25 | 0.25 |  |  |  |
|  | MIC of IA25 | 0.12 | FIC B = 0.5 |  |  |
|  | MIC of IA25 with Ehambutol | 0.06 |  |  |  |

IIA3 & IA25 has shown synergistic or additive activity with rifampicin, INH and ethambutol.

Advantage of the Invention

Compounds of formula I and II of general formula 1 have shown potent MIC against H37Rv TB as well MDR-TB and XDR-TB.

Compounds of the general formula 1 exhibit promising pharmaco-kinetics properties with acceptable $C_{max}$ and AUC.

Compounds of the formula I and II of general formula 1 shows synergistic as well as additive affect in combination studies with other first line anti-TB agents such as isoniazid, rifampicine and ethambutol.

We claim:

1. A compound of formula 1 or pharmaceutically acceptable salts thereof

Formula 1

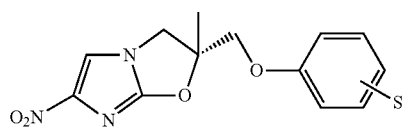

wherein
substituent 'S' is selected from the group consisting of formula Ia, Ib, Ic, IIa, IIb and IIc;

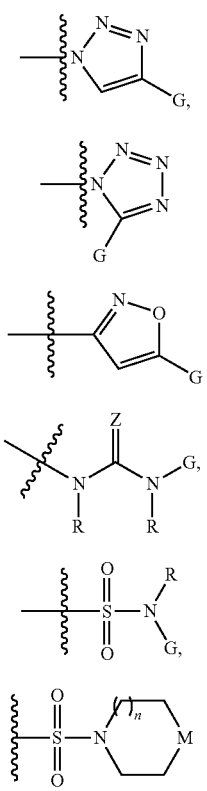

wherein,
'G' is selected from the group consisting of H, $CH_2OR_1$, $OR_1$ and $R_1$;
'Z' is selected from the group consisting of O, S and $NR_2$;
'n' is any number from 0 to 2;
'M' is selected from the group consisting of O, S, $NR_2$ and $CR_3R_4$;
R, $R_1$ and $R_2$ are each independently selected from the group consisting of H, alkyl, substituted alkyl, aryl, substituted aryl, phenyl, substituted phenyl, heterocyclic and substituted heterocyclic group selected from the group consisting of pyridyl, triazolyl, triazinyl, pyrimidinyl, pyridazinyl, oxazolyl, furanyl, benzofuranyl, thiophenyl, pyrrolyl, imidazoyl, thiazoyl, quinolinyl, isoquinolinyl, benzooxazolyl and benzothiazolyl; and
$R_3$ and $R_4$ are each independently selected from the group consisting of H, alkyl, substituted alkyl, alkoxyl, substituted alkoxyl, phenyl, substituted phenyl, phenoxyl, substituted phenoxyl, heterocyclic and substituted heterocyclic group selected from the group consisting of pyridyl, triazolyl, triazinyl, pyrimidinyl, pyridazinyl, oxazolyl, furanyl, thiophenyl, pyrrolyl, imidazoyl and thiazoyl.

2. The compound of formula 1 as claimed in claim 1 selected from the group consisting of compound of formula I and formula II,

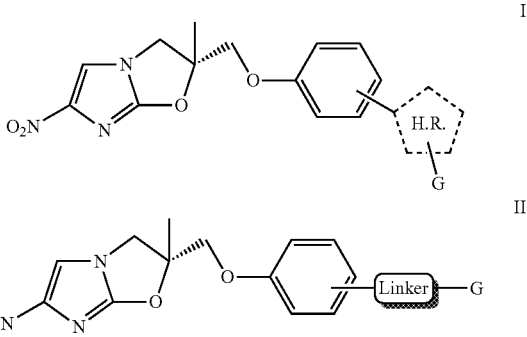

wherein

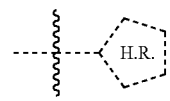

is selected from the group consisting of formula Ia, Ib and Ic;

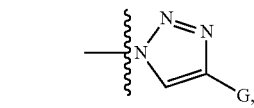

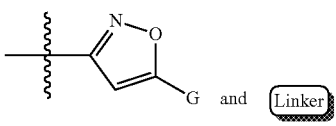

is selected from the group consisting of formula IIa, IIb and IIc;

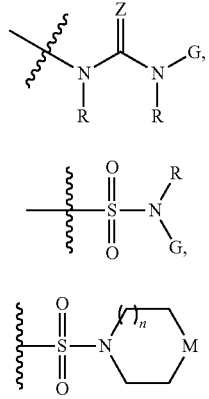

wherein,
G' is selected from the group consisting of H, CH$_2$OR$_1$, OR$_1$ and R$_1$;
'Z' is selected from the group consisting of O, S and NR$_2$;
'n' is any number from 0 to 2;
'M' is selected from the group consisting of O, S, NR$_2$ and CR$_3$R$_4$;
R, R$_1$ and R$_2$ are each independently selected from the group consisting of H, alkyl, substituted alkyl, aryl, substituted aryl, phenyl, substituted phenyl, heterocyclic and substituted heterocyclic group selected from the group consisting of pyridyl, triazolyl, triazinyl, pyrimidinyl, pyridazinyl, oxazolyl, furanyl, benzofuranyl, thiophenyl, pyrrolyl, imidazoyl, thiazoyl, quinolinyl, isoquinolinyl, benzooxazolyl and benzothiazolyl; and
R$_3$ and R$_4$ are each independently selected from the group consisting of H, alkyl, substituted alkyl, alkoxyl, substituted alkoxyl, phenyl, substituted phenyl, phenoxyl, substituted phenoxyl, heterocyclic and substituted heterocyclic group selected from the group consisting of pyridyl, triazolyl, triazinyl, pyrimidinyl, pyridazinyl, oxazolyl, furanyl, thiophenyl, pyrrolyl, imidazoyl and thiazoyl.

3. The compound of formula 1 as claimed in claim 2, wherein compound of formula I is present and selected from the group consisting of compound of formula IA, IB and IC,

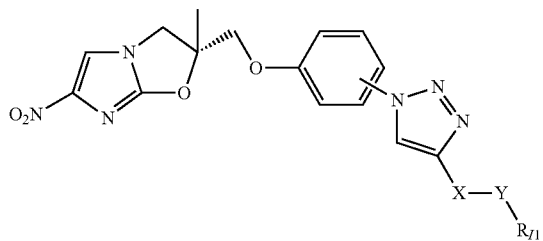

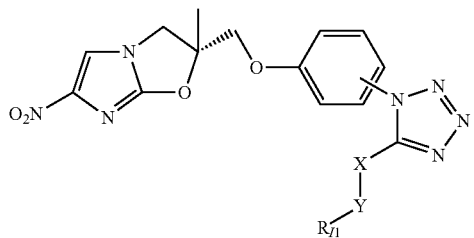

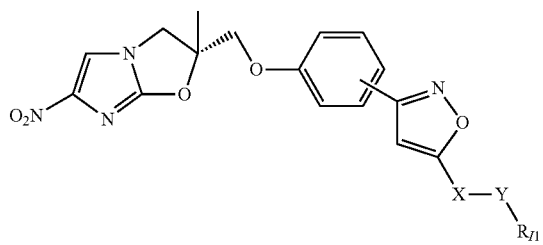

wherein
'X' is CH$_2$ or a direct bond;
'Y' is selected from the group consisting of O, S, and NR$_{I2}$, or a direct bond;
R$_{I1}$ is selected from the group consisting of H, alkyl, aryl, substituted alkyl, substituted aryl, heterocyclic, substituted heterocyclic group selected from the group consisting of pyridyl, triazolyl, triazinyl, pyrimidinyl, pyridazinyl, oxazolyl, furanyl, benzofuranyl, thiophenyl, pyrrolyl, imidazoyl, thiazoyl, quinolinyl, isoquinolinyl, benzooxazolyl, and benzothiazolyl; and substituted aryl is selected from the group consisting of F, Cl, Br, I, NR$_{I3}$R$_{I4}$, CF$_3$, OCF$_3$, OR$_{I5}$, NO$_2$, CHR$_{I6}$R$_{I7}$, alkyl group having C1 to C14, COOR$_{I8}$, CHO, and COR$_{I9}$;
R$_{I2}$, R$_{I3}$, R$_{I4}$, R$_{I5}$, R$_{I8}$ and R$_{I9}$ are each independently selected from the group consisting of H, alkyl, alkoxyl, substituted alkoxyl, phenyl, substituted phenyl, phenoxyl, substituted phenoxyl, heterocyclic and substituted heterocyclic group selected from the group consisting of pyridyl, triazolyl, triazinyl, pyrimidinyl, pyridazinyl, oxazolyl, furanyl, thiophenyl, pyrrolyl, imidazoyl and thiazoyl; and
R$_{I6}$ and R$_{I7}$ are each independently selected from the group consisting of H, alkyl, phenyl, substituted phenyl, heterocyclic and substituted heterocyclic group selected from the group consisting of pyridyl, triazolyl, triazinyl, pyrimidinyl, pyridazinyl, oxazolyl, furanyl, thiophenyl, pyrrolyl, imidazoyl and thiazoyl.

4. The compound of formula 1 as claimed in claim 2, wherein the compound of formula II is present and selected from the group consisting of compound of formula IIA, IIB and IIC,

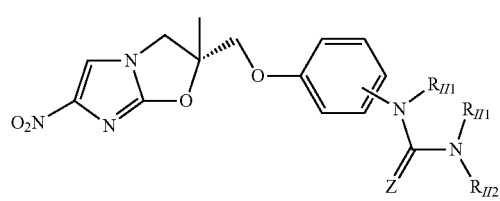

-continued

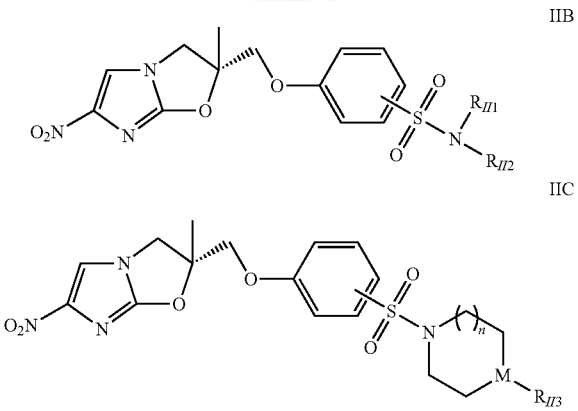

IIB

IIC wherein
- 'Z' is selected from the group consisting of 0, S, and $NR_{II4}$;
- 'n' is any number from 0 to 2;
- 'M' is selected from the group consisting O, S, CH and N;
- $R_{II1}$, $R_{II2}$, $R_{II3}$ and $R_{II4}$ are each independently selected from the group consisting of H, alkyl, aryl, substituted alkyl, substituted aryl, heterocyclic and substituted heterocyclic group selected from the group consisting of pyridyl, triazolyl, triazinyl, pyrimidinyl, pyridazinyl, oxazolyl, furanyl, benzofuranyl, thiophenyl, pyrrolyl, imidazoyl, thiazoyl, quinolinyl, isoquinolinyl, benzooxazolyl, and benzothiazolyl; and substituted aryl is selected from the group consisting of F, Cl, Br, I, $NR_{II5}R_{II6}$, $CF_3$, $OCF_3$, $OR_{II7}$, $NO_2$, $CHR_{II8}R_{II9}$, alkyl group having C1 to C14, $COOR_{II10}$, CHO, and $COR_{II11}$;
- $R_{II5}$, $R_{II6}$, $R_{II7}$, $R_{II10}$ and $R_{II11}$ are each independently selected from the group consisting of H, alkyl phenyl, substituted phenyl, heterocyclic and substituted heterocyclic group selected from the group consisting of pyridyl, triazolyl, triazinyl, pyrimidinyl, pyridazinyl, oxazolyl, furanyl, thiophenyl, pyrrolyl, imidazoyl and thiazoyl; and
- $R_{II8}$ and $R_{II9}$ are each independently selected from the group consisting of H, alkyl alkoxy, substituted alkoxy, phenyl, substituted phenyl, phenoxy, substituted phenoxy, heterocyclic and substituted heterocyclic group selected from the group consisting of pyridyl, triazolyl, triazinyl, pyrimidinyl, pyridazinyl, oxazolyl, furanyl, thiophenyl, pyrrolyl, imidazoyl and thiazoyl.

5. The compound of formula 1 as claimed in claim 1 selected from the group consisting of:
(R)-2-{4-(4-phenyl-1H-1,2,3-triazol-1-yl)phenoxy)methyl}-2,3-dihydro-2-methyl-6-nitroimidazo[2,1-b]oxazole (compound IA1),
(R)-2-{4-[4-(4-ethylphenyl)-1H-1,2,3-triazol-1-yl]phenoxymethyl}-2,3-dihydro-2-methyl-6-nitroimidazo[2,1-b]oxazole (compound IA2),
(R)-2-{4-[4-(4-fluorophenyl)-1H-1,2,3-triazol-1-yl]phenoxymethyl}-2,3-dihydro-2-methyl-6-nitroimidazo[2,1-b]oxazole (compound IA3),
(R)-2-{4-[4-(2-fluorophenyl)-1H-1,2,3-triazol-1-yl]phenoxymethyl}-2,3-dihydro-2-methyl-6-nitroimidazo[2,1-b]oxazole (compound IA4),
(R)-2-{4-[4-(4-trifluoromethoxyphenyl)-1H-1,2,3-triazol-1-yl]phenoxymethyl}-2,3-dihydro-2-methyl-6-nitroimidazo[2,1-b]oxazole (compound IA5),
(R)-2-{4-[4-(2-trifluoromethylphenyl)-1H-1,2,3-triazol-1-yl]phenoxymethyl}-2,3-dihydro-2-methyl-6-nitroimidazo[2,1-b]oxazole (compound IA6),
(R)-2-{4-[4-(2,4-difluorophenyl)-1H-1,2,3-triazol-1-yl]phenoxymethyl}-2,3-dihydro-2-methyl-6-nitroimidazo[2,1-b]oxazole (compound IA7),
(R)-2-{4-[4-(4-methylphenyl)-1H-1,2,3-triazol-1-yl]phenoxymethyl}-2,3-dihydro-2-methyl-6-nitroimidazo[2,1-b]oxazole (compound IA8),
(R)-2-{4-[4-(4-isopropylphenyl)-1H-1,2,3-triazol-1-yl]phenoxymethyl}-2,3-dihydro-2-methyl-6-nitroimidazo[2,1-b]oxazole (compound IA9),
(R)-2-{4-[4-(3-fluorophenyl)-1H-1,2,3-triazol-1-yl]phenoxymethyl}-2,3-dihydro-2-methyl-6-nitroimidazo[2,1-b]oxazole (compound IA10),
(R)-2-{4-[4-(4-methoxyphenyl)-1H-1,2,3-triazol-1-yl]phenoxymethyl}-2,3-dihydro-2-methyl-6-nitroimidazo[2,1-b]oxazole (compound IA11),
(R)-2-{4-[4-(3-trifluoromethoxyphenyl)-1H-1,2,3-triazol-1-yl]phenoxymethyl}-2,3-dihydro-2-methyl-6-nitroimidazo[2,1-b]oxazole (compound IA12),
(R)-2-{4-[4-(3-trifluoromethylphenyl)-1H-1,2,3-triazol-1-yl]phenoxymethyl}-2,3-dihydro-2-methyl-6-nitroimidazo[2,1-b]oxazole (compound IA13),
(R)-2-{4-[4-(4-pyridin-2-yl)-1H-1,2,3-triazol-1-yl]phenoxymethyl}-2,3-dihydro-2-methyl-6-nitroimidazo[2,1-b]oxazole (compound IA14),
(R)-2-{4-[4-pentyl-1H-1,2,3-triazol-1-yl]phenoxymethyl}-2,3-dihydro-2-methyl-6-nitroimidazo[2,1-b]oxazole (compound IA15),
(R)-2-{4-[4-heptyl-1H-1,2,3-triazol-1-yl]phenoxymethyl}-2,3-dihydro-2-methyl-6-nitroimidazo[2,1-b]oxazole (compound IA16),
(R)-2-{3-[4-(4-fluorophenyl)-1H-1,2,3-triazol-1-yl]phenoxymethyl}-2,3-dihydro-2-methyl-6-nitroimidazo[2,1-b]oxazole (compound IA17),
(R)-2-{3-[4-(4-trifluoromethylphenyl)-1H-1,2,3-triazol-1-yl]phenoxymethyl}-2,3-dihydro-2-methyl-6-nitroimidazo[2,1-b]oxazole (compound IA18),
(R)-2-{3-[4-(4-trifluoromethoxyphenyl)-1H-1,2,3-triazol-1-yl]phenoxymethyl}-2,3-dihydro-2-methyl-6-nitroimidazo[2,1-b]oxazole (compound IA19),
(R)-2-{3-[4-(2,4-difluorophenyl)-1H-1,2,3-triazol-1-yl]phenoxymethyl}-2,3-dihydro-2-methyl-6-nitroimidazo[2,1-b]oxazole (compound IA20),
(R)-2-{2-[4-(4-fluorophenyl)-1H-1,2,3-triazol-1-yl]phenoxymethyl}-2,3-dihydro-2-methyl-6-nitroimidazo[2,1-b]oxazole (compound IA21),
(R)-2-{2-[4-(4-trifluoromethylphenyl)-1H-1,2,3-triazol-1-yl]phenoxymethyl}-2,3-dihydro-2-methyl-6-nitroimidazo[2,1-b]oxazole (compound IA22),
(R)-2-{2-[4-(4-trifluoromethoxyphenyl)-1H-1,2,3-triazol-1-yl]phenoxymethyl}-2,3-dihydro-2-methyl-6-nitroimidazo[2,1-b]oxazole (compound IA23),
(R)-2-{2-[4-(2,4-difluorophenyl)-1H-1,2,3-triazol-1-yl]phenoxymethyl}-2,3-dihydro-2-methyl-6-nitroimidazo[2,1-b]oxazole (compound IA24),
(R)-2-{4-[4-(4-trifluoromethoxyphenoxy)methyl)-1H-1,2,3-triazol-1-yl]phenoxymethyl}-2,3-dihydro-2-methyl-6-nitroimidazo[2,1-b]oxazole (compound IA25),
(R)-2-{4-[4-(4-fluorophenoxy)methyl)-1H-1,2,3-triazol-1-yl]phenoxymethyl}-2,3-dihydro-2-methyl-6-nitroimidazo[2,1-b]oxazole (compound IA26), (R)-2-{4-[4-(4-trifluoromethylphenoxy)methyl)-1H-1,2,3-triazol-1-yl]phenoxymethyl}-2,3-dihydro-2-methyl-6-nitroimidazo[2,1-b]oxazole (compound IA27),
(R)-2-{4-[4-(2-fluorophenoxy)methyl)-1H-1,2,3-triazol-1-yl]phenoxymethyl}-2,3-dihydro-2-methyl-6-nitroimidazo[2,1-b]oxazole (compound IA28),
(R)-2-{4-[4-(4-methylphenoxy)methyl)-1H-1,2,3-triazol-1-yl]phenoxymethyl}-2,3-dihydro-2-methyl-6-nitroimidazo[2,1-b]oxazole (compound IA29),
(R)-2-{4-[4-(4-isopropylphenoxy)methyl)-1H-1,2,3-triazol-1-yl]phenoxymethyl}-2,3-dihydro-2-methyl-6-nitroimidazo[2,1-b]oxazole (compound IA30),
(R)-2-{4-[4-(4-ethylphenoxy)methyl)-1H-1,2,3-triazol-1-yl]phenoxymethyl}-2,3-dihydro-2-methyl-6-nitroimidazo[2,1-b]oxazole (compound IA31),
(R)-2-{4-[4-(4-sec-butylphenoxy)methyl)-1H-1,2,3-triazol-1-yl]phenoxymethyl}-2,3-dihydro-2-methyl-6-nitroimidazo[2,1-b]oxazole (compound IA32),
(R)-2-{3-[4-(4-trifluoromethoxyphenoxy)methyl)-1H-1,2,3-triazol-1-yl]phenoxymethyl}-2,3-dihydro-2-methyl-6-nitroimidazo[2,1-b]oxazole (compound IA33),
(R)-2-{3-[4-(4-fluorophenoxy)methyl)-1H-1,2,3-triazol-1-yl]phenoxymethyl}-2,3-dihydro-2-methyl-6-nitroimidazo[2,1-b]oxazole (compound IA34),
(R)-2-{3-[4-(4-trifluoromethylphenoxy)methyl)-1H-1,2,3-triazol-1-yl]phenoxymethyl}-2,3-dihydro-2-methyl-6-nitroimidazo[2,1-b]oxazole (compound IA35),
(R)-2-{3-[4-(2-fluorophenoxy)methyl)-1H-1,2,3-triazol-1-yl]phenoxymethyl}-2,3-dihydro-2-methyl-6-nitroimidazo[2,1-b]oxazole (compound IA36),
(R)-2-{3-[4-(4-methylphenoxy)methyl)-1H-1,2,3-triazol-1-yl]phenoxymethyl}-2,3-dihydro-2-methyl-6-nitroimidazo[2,1-b]oxazole (compound IA37),
(R)-2-{3-[4-(4-isopropylphenoxy)methyl)-1H-1,2,3-triazol-1-yl]phenoxymethyl}-2,3-dihydro-2-methyl-6-nitroimidazo[2,1-b]oxazole (compound IA38),
(R)-2-{2-[4-(4-trifluoromethoxyphenoxy)methyl)-1H-1,2,3-triazol-1-yl]phenoxymethyl}-2,3-dihydro-2-methyl-6-nitroimidazo[2,1-b]oxazole (compound IA39),
(R)-2-{2-[4-(4-fluorophenoxy)methyl)-1H-1,2,3-triazol-1-yl]phenoxymethyl}-2,3-dihydro-2-methyl-6-nitroimidazo[2,1-b]oxazole (compound IA40),
(R)-2-{2-[4-(4-trifluoromethylphenoxy)methyl)-1H-1,2,3-triazol-1-yl]phenoxymethyl}-2,3-dihydro-2-methyl-6-nitroimidazo[2,1-b]oxazole (compound IA41),
(R)-2-{2-[4-(2-fluorophenoxy)methyl)-1H-1,2,3-triazol-1-yl]phenoxymethyl}-2,3-dihydro-2-methyl-6-nitroimidazo[2,1-b]oxazole (compound IA42),
(R)-2-{4-[5-phenyl-1H-tetrazol-1-yl]phenoxymethyl}-2,3-dihydro-2-methyl-6-nitroimidazo[2,1-b]oxazole (compound IB1),
(R)-2-{4-[5-(4-trifluoromethoxyphenyl)-1H-tetrazol-1-yl]phenoxymethyl}-2,3-dihydro-2-methyl-6-nitroimidazo[2,1-b]oxazole (compound IB2),
(R)-2-{4-[5-(4-methylphenyl)-1H-tetrazol-1-yl]phenoxymethyl}-2,3-dihydro-2-methyl-6-nitroimidazo[2,1-b]oxazole (compound IB3),
(R)-2-{4-[5-(4-fluorophenyl)-1H-tetrazol-1-yl]phenoxymethyl}-2,3-dihydro-2-methyl-6-nitroimidazo[2,1-b]oxazole (compound IB4),
(R)-2-{4-[5-(4-trifluoromethylphenyl)-1H-tetrazol-1-yl]phenoxymethyl}-2,3-dihydro-2-methyl-6-nitroimidazo[2,1-b]oxazole (compound IB5),
(R)-2-{4-[5-(4-ethylphenyl)-1H-tetrazol-1-yl]phenoxymethyl}-2,3-dihydro-2-methyl-6-nitroimidazo[2,1-b]oxazole (compound IB6),
(R)-2-{4-[5-(4-fluorophenoxy)-1H-tetrazol-1-yl]phenoxymethyl}-2,3-dihydro-2-methyl-6-nitroimidazo[2,1-b]oxazole (compound IB7),
(R)-2-{4-[5-(4-trifluoromethylphenoxy)-1H-tetrazol-1-yl]phenoxymethyl}-2,3-dihydro-2-methyl-6-nitroimidazo[2,1-b]oxazole (compound IB8),
(R)-2-{4-[5-(4-methylphenoxy)-1H-tetrazol-1-yl]phenoxymethyl}-2,3-dihydro-2-methyl-6-nitroimidazo[2,1-b]oxazole (compound D39),
(R)-2-{4-[5-(4-trifluoromethoxyphenoxy)-1H-tetrazol-1-yl]phenoxymethyl}-2,3-dihydro-2-methyl-6-nitroimidazo[2,1-b]oxazole (compound D310),
(R)-2-{4-[5-phenylisoxazol-3-yl]phenoxymethyl}-2,3-dihydro-2-methyl-6-nitroimidazo[2,1-b]oxazole (compound IC1),
(R)-2-{4-[5-(4-ethylphenyl)isoxazol-3-yl]phenoxymethyl}-2,3-dihydro-2-methyl-6-nitroimidazo[2,1-b]oxazole (compound IC2),
(R)-2-{4-[5-(2,4-difluorophenyl)isoxazol-3-yl]phenoxymethyl}-2,3-dihydro-2-methyl-6-nitroimidazo[2,1-b]oxazole (compound IC3),
(R)-2-{4-[5-(2-fluorophenyl)isoxazol-3-yl]phenoxymethyl}-2,3-dihydro-2-methyl-6-nitroimidazo[2,1-b]oxazole (compound IC4),
(R)-2-{4-[5-(4-trifluoromethylphenyl)isoxazol-3-yl]phenoxymethyl}-2,3-dihydro-2-methyl-6-nitroimidazo[2,1-b]oxazole (compound IC5),
(R)-2-{4-[5-(4-methylphenyl)isoxazol-3-yl]phenoxymethyl}-2,3-dihydro-2-methyl-6-nitroimidazo[2,1-b]oxazole (compound IC6),
(R)-2-{4-[5-(4-methoxyphenyl)isoxazol-3-yl]phenoxymethyl}-2,3-dihydro-2-methyl-6-nitroimidazo[2,1-b]oxazole (compound IC7),
(R)-2-{4-[5-(3-fluorophenyl)isoxazol-3-yl]phenoxymethyl}-2,3-dihydro-2-methyl-6-nitroimidazo[2,1-b]oxazole (compound IC8),
(R)-2-{4-[5-(pyridin-2-yl)isoxazol-3-yl]phenoxymethyl}-2,3-dihydro-2-methyl-6-nitroimidazo[2,1-b]oxazole (compound IC9),
(R)-2-{4-[5-(4-trifluoromethoxyphenyl)isoxazol-3-yl]phenoxymethyl}-2,3-dihydro-2-methyl-6-nitroimidazo[2,1-b]oxazole (compound IC10),
(R)-2-{4-[5-pentylisoxazol-3-yl]phenoxymethyl}-2,3-dihydro-2-methyl-6-nitroimidazo[2,1-b]oxazole (compound IC11),
(R)-2-{4-[5-heptylisoxazol-3-yl]phenoxymethyl}-2,3-dihydro-2-methyl-6-nitroimidazo[2,1-b]oxazole (compound IC12),
(R)-2-{4-[5-(4-trifluoromethoxyphenoxymethyl)isoxazol-3-yl]phenoxymethyl}-2,3-dihydro-2-methyl-6-nitroimidazo[2,1-b]oxazole (compound IC13),
(R)-2-{4-[5-(4-fluorophenoxymethyl)isoxazol-3-yl]phenoxymethyl}-2,3-dihydro-2-methyl-6-nitroimidazo[2,1-b]oxazole (compound IC14),
(R)-2-{4-[5-(4-trifluoromethylphenoxymethyl)isoxazol-3-yl]phenoxymethyl}-2,3-dihydro-2-methyl-6-nitroimidazo[2,1-b]oxazole (compound IC15),
(R)-2-{4-[5-(2-fluorophenoxymethyl)isoxazol-3-yl]phenoxymethyl}-2,3-dihydro-2-methyl-6-nitroimidazo[2,1-b]oxazole (compound IC16 5),
(R)-2-{4-[5-(4-methylphenoxymethyl)isoxazol-3-yl]phenoxymethyl}-2,3-dihydro-2-methyl-6-nitroimidazo[2,1-b]oxazole (compound IC17), (R)-2-{4-[5-(4-isopropylphenoxymethyl)isoxazol-3-yl]phenoxymethyl}-2,3-dihydro-2-methyl-6-nitroimidazo[2,1-b]oxazole (compound IC18), (R)-2-{4-[5-(4-ethylphenoxymethyl)isoxazol-3-yl]phenoxymethyl}-2,3-dihydro-2-methyl-6-nitroimidazo[2,1-b]oxazole (compound IC19), (R)-2-{4-[5-(4-sec-butylphenoxymethyl)isoxazol-3-yl]phenoxymethyl}-2,3-dihydro-2-methyl-6-nitroimidazo[2,1-b]oxazole (compound IC20), (R)-2-{4-[5-(phenoxymethyl)isoxazol-3-yl]phenoxymethyl}-2,3-dihydro-2-methyl-6-nitroimidazo[2,1-b]oxazole (compound IC21), (R)-2-{4-[5-(2,4-difluorophenoxymethyl)isoxazol-3-yl]phenoxymethyl}-2,3-dihydro-2-methyl-6-nitroimidazo[2,1-b]oxazole (compound IC22), (R)-1-(4-fluorophenyl)-3-{4-(2-methyl-6-nitro-2,3-dihydroimidazo[2,1-b]oxazol-2-yl)methoxyphenyl}urea (compound IIA1), (R)-1-(4-ethylphenyl)-3-{4-(2-methyl-6-nitro-2,3-dihydroimidazo[2,1-b]oxazol-2-yl)methoxyphenyl}urea (compound IIA2), (R)-1-(4-trifluoromethylphenyl)-3-{4-(2-methyl-6-nitro-2,3-dihydroimidazo[2,1-b]oxazol-2-yl)methoxyphenyl}urea (compound IIA3), (R)-1-(4-methylphenyl)-3-{4-(2-methyl-6-nitro-2,3-dihydroimidazo[2,1-b]oxazol-2-yl)methoxyphenyl}urea (compound IIA4), (R)-1-(4-methoxyphenyl)-3-{4-(2-methyl-6-nitro-2,3-dihydroimidazo[2,1-b]oxazol-2-yl)methoxyphenyl}urea (compound IIA5), (R)-1-(4-trifluoromethoxyphenyl)-3-{4-(2-methyl-6-nitro-2,3-dihydroimidazo[2,1-b]oxazol-2-yl)methoxyphenyl}urea (compound IIA6), (R)-1-(4-methoxyphenyl)-3-{4-(2-methyl-6-nitro-2,3-dihydroimidazo[2,1-b]oxazol-2-yl)methoxyphenyl}thiourea (compound IIA7), (R)-1-(4-trifluoromethoxyphenyl)-3-{4-(2-methyl-6-nitro-2,3-dihydroimidazo[2,1-b]oxazol-2-yl)methoxyphenyl}thiourea (compound IIA8), (R)-1-(4-fluorophenyl)-3-{4-(2-methyl-6-nitro-2,3-dihydroimidazo[2,1-b]oxazol-2-yl)methoxyphenyl}thiourea (compound IIA9), (R)-1-(4-trifluoromethylphenyl)-3-{4-(2-methyl-6-nitro-2,3-dihydroimidazo[2,1-b]oxazol-2-yl)methoxyphenyl}thiourea (compound IIA10), (R)-4-{(2-methyl-6-nitro-2,3-dihydroimidazo[2,1-b]oxazol-2-yl)methoxyl}-N-(p-tolyl)benzenesulfonamide (compound IIB1), (R)-4-{(2-methyl-6-nitro-2,3-dihydroimidazo[2,1-b]oxazol-2-yl)methoxyl}-N-(p-trifluoromethoxyphenyl)benzenesulfonamide (compound IIB2), (R)-4-{(2-methyl-6-nitro-2,3-dihydroimidazo[2,1-b]oxazol-2-yl)methoxyl}-N-(p-trifluoromethylphenyl)benzenesulfonamide (compound IIB3), (R)-N-methyl-4-{(2-methyl-6-nitro-2,3-dihydroimidazo[2,1-b]oxazol-2-yl)methoxyl}-N-phenylbenzenesulfonamide (compound IIB4), (R)-N-methyl-4-{(2-methyl-6-nitro-2,3-dihydroimidazo[2,1-b]oxazol-2-yl)methoxyl}-N-(p-tolyl)benzenesulfonamide (compound IIB5), (R)-N-methyl-4-{(2-methyl-6-nitro-2,3-dihydroimidazo[2,1-b]oxazol-2-yl)methoxyl}-N-(p-trifluoromethylphenyl)benzenesulfonamide (compound IIB6), (R)-2-{4-(4-phenylpiperazin-1-yl)sulfonylphenoxymethyl}-2,3-dihydro-2-methyl-6-nitroimidazo[2,1-b]oxazole (compound IIC1), (R)-2-{4-[4-(4-fluorophenyl)piperazin-1-yl]sulfonylphenoxymethyl}-2,3-dihydro-2-methyl-6-nitroimidazo[2,1-b]oxazole (compound IIC2), (R)-2-{4-[4-(3-chlorophenyl)piperazin-1-yl]sulfonylphenoxymethyl}-2,3-dihydro-2-methyl-6-nitroimidazo[2,1-b]oxazole (compound IIC3), (R)-2-{4-[4-(4-trifluoromethoxyphenyl)piperazin-1-yl]sulfonylphenoxymethyl}-2,3-dihydro-2-methyl-6-nitroimidazo[2,1-b]oxazole (compound IIC4), (R)-ethyl-{4-[4-(2-methyl-6-nitro-2,3-dihydroimidazo[2,1-b]oxazol-2yl)methoxyphenyl]sulfonyl}piperazine-1-carboxylate (compound IIC5), (R)-{4-[4-(2-methyl-6-nitro-2,3-dihydroimidazo[2,1-b]oxazol-2yl)methoxyphenyl]sulfonyl}piperazine-1-yl(phenyl)methanone (compound IIC6), (R)-2-{4-(piperidin-1-ylsulfonyl)phenoxymethyl}-2,3-dihydro-2-methyl-6-nitroimidazo[2,1-b]oxazole (compound IIC7), (R)-2-{4-[(4-phenylpiperidin-1-yl)sulfonyl]phenoxymethyl}-2,3-dihydro-2-methyl-6-nitroimidazo[2,1-b]oxazole (compound IIC8), (R)-2-{4-(pyrrolidin-1-ylsulfonyl)phenoxymethyl}-2,3-dihydro-2-methyl-6-nitroimidazo[2,1-b]oxazole (compound IIC9), and (R)-2-{4-(morpholinsulfonyl)phenoxymethyl}-2,3-dihydro-2-methyl-6-nitroimidazo[2,1-b]oxazole (compound IIC10).

6. The compounds of formula 1 as claimed in claim 1, wherein the pharmaceutically acceptable salts are salts of an acid selected from the group consisting of hydrochloric acid, sulphuric acid, phosphoric acid, acetic acid, citric acid, oxalic acid, malonic acid, salicylic acid, malic acid, fumaric acid, succinic acid, ascorbic acid, maleic acid, methanesulfonic acid and isoethonic acids or salts of a base selected from the group consisting of potassium carbonate, sodium hydroxide, potassium hydroxide, ammonia, triethylamine and triethanolamine.

* * * * *